(12) United States Patent
Hazan et al.

(10) Patent No.: US 10,307,449 B2
(45) Date of Patent: *Jun. 4, 2019

(54) COMPOSITIONS OF POLYMERIC MYRCENE

(71) Applicant: REGENERA PHARMA LTD., Rehovot (IL)

(72) Inventors: Zadik Hazan, Zichron Yaakov (IL); Shimon Amselem, Rehovot (IL)

(73) Assignee: REGENERA PHARMA LTD., Rehovot (IL)

( * ) Notice: Subject to any disclaimer, the term of this patent is extended or adjusted under 35 U.S.C. 154(b) by 53 days.

This patent is subject to a terminal disclaimer.

(21) Appl. No.: 15/486,964

(22) Filed: Apr. 13, 2017

(65) Prior Publication Data

US 2017/0252387 A1 Sep. 7, 2017

Related U.S. Application Data

(63) Continuation of application No. 14/226,293, filed on Mar. 26, 2014, now Pat. No. 9,655,938, which is a continuation of application No. 13/254,380, filed as application No. PCT/IL2010/000184 on Mar. 4, 2010, now Pat. No. 8,722,105.

(60) Provisional application No. 61/157,216, filed on Mar. 4, 2009.

(51) Int. Cl.
*A61K 36/00* (2006.01)
*A61K 36/22* (2006.01)

(52) U.S. Cl.
CPC .................... *A61K 36/22* (2013.01)

(58) Field of Classification Search
None
See application file for complete search history.

(56) References Cited

U.S. PATENT DOCUMENTS

| | | |
|---|---|---|
| 4,374,957 A | 2/1983 | Quirk |
| 4,564,718 A | 1/1986 | Still |
| 4,713,243 A | 12/1987 | Schiraldi |
| 5,506,406 A | 4/1996 | Kapp |
| 5,637,290 A | 6/1997 | Sodis |
| 5,759,569 A | 6/1998 | Hird |
| 5,948,430 A | 9/1999 | Zerbe |
| 6,074,688 A | 6/2000 | Pletcher |
| 6,177,096 B1 | 1/2001 | Zerbe |
| 6,284,264 B1 | 9/2001 | Zerbe |
| 6,319,541 B1 | 11/2001 | Pletcher |
| 6,592,887 B2 | 7/2003 | Zerbe |
| 6,623,728 B2 | 9/2003 | Harichian |
| 6,709,671 B2 | 3/2004 | Zerbe |
| 6,811,769 B2 | 11/2004 | Watanabe |
| 7,048,943 B2 | 5/2006 | Barenholz |
| 7,056,491 B2 | 6/2006 | Gould |
| 7,214,750 B2 | 5/2007 | McDonald |
| 7,232,872 B2 | 6/2007 | Shaffer |
| 7,294,651 B2 | 11/2007 | Syverson |
| 7,417,103 B2 | 8/2008 | Hou |
| 2005/0163876 A1 | 7/2005 | Belloni Regazzo |
| 2005/0238740 A1 | 10/2005 | Fotinos |
| 2007/0148187 A1 | 6/2007 | Scivoletto |
| 2007/0179260 A1 | 8/2007 | Hou |
| 2008/0234380 A1 | 9/2008 | Shapiro |
| 2012/0003175 A1 | 1/2012 | Hazan |

FOREIGN PATENT DOCUMENTS

| | | | |
|---|---|---|---|
| EP | 1520585 | 4/2005 | |
| EP | 1721914 | 11/2006 | |
| EP | 2008661 | 12/2008 | |
| EP | 1501527 | 9/2009 | |
| EP | 1781235 | 12/2013 | |
| GR | 1003541 | 3/2001 | |
| GR | 1003868 | 4/2002 | |
| JP | 63179908 | 7/1988 | |
| JP | 10130254 | 5/1998 | |
| JP | 10130254 A * | 5/1998 | |
| WO | 89/12454 | 12/1989 | |
| WO | 01/21212 | 3/2001 | |
| WO | 03/092712 | 11/2003 | |
| WO | 2005053812 | 6/2005 | |
| WO | 2005/112967 | 12/2005 | |
| WO | WO 2005112967 A2 * | 12/2005 | ............. A61K 36/22 |
| WO | 2006/003659 | 1/2006 | |
| WO | 2006/053249 | 5/2006 | |
| WO | 2007/014334 | 2/2007 | |

OTHER PUBLICATIONS

Berg et al, Cis-1,4-poly-beta-myrcene; the structure of the polymeric fraction of mastic resin (*Pistacia lentiscus* L.) elucidated. Tetrahedron letters: the international organ for the rapid publication of preliminary communications in organic chemistry, Apr. 23, 1998. vol. 39, No. 17. p. 2645-2648.*
Abu Ali Ibn-e-Sina; Al-Qaanoon-fil-Tibb, vol. II (11th century AD), Institute of History of Medicine and Medical Research, Jamia Hamdard, New Delhi-62, 1987 AD p. 386. Formulation ID: AH1/665E; Formulation name: Mazoogh Barae Tanqiya-e-Raas.
Agnivesa; Caraka Samhita—Edited & translated by P.V Sharma, vol. I: Chaukhamba Orientalia, Varanasi, 6th edn, 2000 (time of origin 1000 BC—4th century), p. 217. Formulation ID: BP/1744B, formulation name: Ghanaguna. Retrieved on Apr. 28, 2014.
Al-Habbal et al., (1984) A double-blind controlled clinical trial of mastic and placebo in the treatment of duodenal ulcer. Clin Exp Pharmacol Physiol 11(5):541-544.
Al-Said et al., (1986) Evaluation of mastic, a crude drug obtained from Pistacia lentiscus for gastric and duodenal anti-ulcer activity. J Ethnopharmacol 15(3):271-278.

(Continued)

*Primary Examiner* — Qiuwen Mi
(74) *Attorney, Agent, or Firm* — Rothwell, Figg, Ernst & Manbeck, P.C.

(57) ABSTRACT

Compositions and formulations comprising polymeric myrcene. More particularly, the invention relates to compositions comprising an isolated fraction of polymeric myrcene in a hydrophobic carrier and formulations which maintain the biological activity of the active polymer.

21 Claims, 25 Drawing Sheets

(56) References Cited

OTHER PUBLICATIONS

Barra et al., (2007) Characterization of the volatile constituents in the essential oil of *Pistacia lentiscus* L. from different origins and its antifungal and antioxidant activity. J Agric Food Chem 55(17):7093-7098.
Bebb et al., (2003) Mastic gum has no effect on Helicobacter pylori load in vivo. J Antimicrob Chemother 52(3):522-523.
Bhagat Bhagavanadasa; Rasarajamahaudadhi (part-1), Khemraj Srikrishnadas, Srrivyankateshwar press. Mumbai, Edition, May—2008, p. 86. Formulation ID: PD/159, formulation name: Kabuli Haritki Ka Murabba. Retrieved on Apr. 28, 2014.
Bharata Bhaisajya Ratnakara—Compiled by Naginadasa Chaganalala Saha, translated by Gopinath Gupta. vol. IV: B. Jain Publishers, New Delhi, 2nd Edn. Reprint, Aug. 1999 (This book contains back references from 1000 B.C. to 20th century), p. 308. Formulation ID: RS/840, formulation name: Yastayadilepah. Retrieved on Apr. 28, 2014.
Brookmeyer et al., (2007) Forecasting the global burden of Alzheimer's disease. Alzheimers Dement 3(3): 186-91.
Caru Cikitsa—Complied by Vaidya Gopinathaji Gupt, Published by Unjha Pharmacy, Gujarat, 4th edition 1950 p. 76. Formulation ID: NG/224; Formulation name: Habbe Ayaraz.
Cawse et al., (1986) Polymers from renewable sources. III. Hydroxy-terminated myrcene polymers. J Appl Polym Sci 31(7):1963-1975.
Dimas et al., (2009) A mastic gum extract induces suppression of growth of human colorectal tumor xenografts in immunodeficient mice. In Vivo 23(1): 63-8.
Dong Huiru et al., (editors) Complicated Substances Analysis Techniques, Chemistry Industry Press, 2004, pp. 177-178.
Farkas et al., (2004) Experimental cerebral hypoperfusion induces white matter injury and microglial activation in the rat brain. Acta Neuropathol 108(1):57-64.
Govinda Dasa; Bhaisajya Ratnavali—Edited by Rajeshvaradutta Shastri, Translated by Ambikaduttashastri: Chaukhamba Sanskrit Sansthan, Varanasi, Edn. 14th, 2001. [this book contains back references from 1000 B.C. to 18th century]. p. 828; formulation ID: AK/4263, formulation name: Surendramodakah.
Haass and Selkoe (2007) Soluble protein oligomers in neurodegeneration: lessons from the Alzheimer's amyloid beta-peptide. Nat Rev Mol Cell Biol 8(2): 101-12.
Hardy (2009) The amyloid hypothesis for Alzheimer's disease: a critical reappraisal. J Neurochem 110(4): 1129-34.
Keisari (1992) A colorimetric microtiter assay for the quantitation of cytokine activity on adherent cells in tissue culture. J Immunol Methods 146(2):155-161.
Khan et al., (2006) Prevention of cognitive impairments and neurodegeneration by Khamira Abresham Hakim Arshad Wala. J Ethnopharmacol 108(1):68-73.
Kimura and Ohno (2009) Impairments in remote memory stabilization precede hippocampal synaptic and cognitive failures in 5XFAD Alzheimer mouse model. Neurobiol Dis 33(2):229-235.
Loughlin et al., (2003) Monotherapy with mastic does not eradicate Helicobacter pylori infection from mice. J Antimicrob Chemother 51(2):367-371.
Magiatis et al., (2002) Evaluation of the wound healing, antioxidant and cytostatic properties of mastic and its element and relative applications. EPODOC Apr. 19, 2002.
Mansouri et al., (2005) The effect of *Pistacia vera* L. gum extract on oxidative damage during experimental cerebral ischemia-reperfusion in rats. Iranian Biomedical Journal, Pasteur Institute of Iran, Iran 9(4):181-185.
Marner et al., (1991) Triterpenoids from gum mastic, the resin ofPistacia lentiscus. Phytochemistry 30(11):3709-3712.
Marone et al., (2001) Bactericidal activity of Pistacia lentiscus mastic gum against Helicobacter pylori. J Chemother 13(6):611-614.
Melnikova (2007) Therapies for Alzheimer's disease. Nat Rev Drug Discov 6(5): 341-2.
Mohammad Akbar Arzani; Qaraabaadeen Qaadri (17th century AD), Ahmadi Publication, Delhi, 1968 AD, pp. 50-51. Formulation ID: MH5/289A, formulation name: Maajoon Falaasfa Deegar. Retrieved on Apr. 28, 2014.
Mohammad Azam Khan; Ikseer Azam, vol. I (19th century AD), Munshi Nawal Kishore, Lucknow, fourth edition p. 53. Formulation ID: NA5/387, formulation name: Sufoof-e-Mastagi. Retrieved on Sep. 3, 2013.
Mohammad Azam Khan; Ikseer Azam, vol. I (19th century AD), Munshi Nawal Kishore, Lucknow, fourth edition p. 187. Formulation ID: NA5/2485, formulation name: Safoof-e-Kundur. Retrieved on Sep. 3, 2013.
Mohammad Azam Khan; Muheet Azam, vol. IV (part II) (19th century AD), Matba Nizami, Kanpur, 1895 AD p. 92. Formulation ID: FA2/185R, formulation name: Roghan Samar-e-mastagi. Retrieved on Sep. 3, 2013.
Mohammad Azam Khan; Muheet-e-Azam vol. III (19th century AD), Matba Nizami, Kanpur, 1887 AD p. 169. Formulation ID: JA7/323B, formulation name: Nuskha Barae Muqawwi Shaar. Retrieved on Apr. 28, 2014.
Mohammad Kabiruddin; Bayaaz-e-Kabir, vol. II (Compiked), Daftar-al-Maseeh, Karol Bagh, New Delhi, 1938 AD pp. 154-155. Formulation ID: MA3/573, formulation name: Majoon-e-Bolas. Retrieved on Sep. 3, 2013.
Mohammad Najmul Gahni Khan; Khazaain-al-Advia, vol. III (20th century AD), Nadeem Yunus Printer/Sheikh Mohd Basheer & Sons, Lahore, 1926 AD, 9. 806. Formulation ID: JA6/769P; Formulation name: Zimaad-e-mastagi.
Mohammad Najmul Ghani Khan; Khazaain-al-Advia, vol. I (20th century AD), Nadeem Yunus Printer/Sheikh Mohd Basheer & Sons, Lahore, 1911 AD p. 746. Formulation ID: NA2/339N, formulation name: Dawa-e-bach Barae Taniqa-e-Dimagh. Retrieved on Sep. 3, 2013.
Mohammad Najmul Ghani Khan; Khazaain-al-Advia, vol. II (20th century AD), Nadeem Yunus Printer/Sheikh Mohd Basheer & Sons, Lahore, 1911 AD p. 918. Formulation ID: AN2/938D, formulation name: Dawa-e-Muqawwi-e-Aasaab. Retrieved on Sep. 3, 2013.
Mohammad Najmul Ghani Khan; Khazaain-al-Advia, vol. II (20th century AD), Nadeem Yunus Printer/Sheikh Mohd Basheer & Sons, Lahore, 1911 AD p. 455. Formulation ID: AN2/431D, formulation name: Raughan-e-habbul Mehlab. Retrieved on Sep. 3, 2013.
Mohammad Najmul Ghani Khan; Qaraabaadeen Najm-al-Ghani (20th century AD), Munshi Nawal Kishore, Lucknow, (second Edition) 1928 AD p. 694. Formulation ID: NA4/4510, formulation name: Majoon Baladur. Retrieved on Sep. 3, 2013.
Mohammad Najmul Ghani Khan; Qaraabaadeen Najm-al-Ghani (20th century AD), Munshi Nawal Kishore, Lucknow, (second edition) 1928 AD, p. 694. Formulation ID: NA4/4508, formulation name: Majoon-e-laboob. Retrieved on Apr. 28, 2014.
Mohammad Najmul Ghani Khan; Qaraabaadeen Najm-al-Ghani (20th century AD), Munshi Nawal Kishore, Lucknow, (second edition) 1924 AD, p. 717. Formulation ID: NA4/4624, formulation name: Majoon Deegar Qawi Tar. Retrieved on Apr. 28, 2014.
Newmark and Majumdar (1988) 13C-NMR spectra of cis-polymyrcene and cis-polyfarnesene. J Polymer Sci A Polym Chem 26(1):71-77.
Paraschos et al., (2007) In vitro and in vivo activities of Chios mastic gum extracts and constituents against Helicobacter pylori. Antimicrob Agents Chemother 51(2):551-559.
Rasatantrasarah Evam Siddhaprayogasamgrahah; part II; Krishan Gopal Ayurveda Bhawan; Edn 8th; 1990 (this book contains back references from 1000 B.C. century) p. 533. Formulation ID: RS21/679, formulation name: Mastiskabalavardhaka Cuma. Retrieved on Sep. 3, 2013.
Rasayoga Sagara—Compiled and Translated by Vaidya Pandita Hariprapanna Ji, vol. II: Krishnadas Academy, Varanasi, Ed., Reprint, 1998 (this book contains back references from 1000 B.C. to 20th century), p. 119. Formulation ID: VS/410, formulation name: Bhallatakapakah. Retrieved on Apr. 28, 2014.
Rasayoga Sagara—Compiled and translated by Vaidya Pandita Hariprapanna Ji, vol. II: Krishnadas Academy, Varanasi, Edb. Reprint, 1998 (this book contains back references from 1000 B.C.

(56) References Cited

OTHER PUBLICATIONS to 20th century), p. 631. Formulation ID: VS/2245, formulation name: Kamesvaramodakah (03). Retrieved on Feb. 18, 2014.
Siddhayogasamgraha—Compiled by Yadavji Trikamji Acharya, Sri Baidyanath Ayurved Bhawan, Allahabad, Edn. 1st 1978 p. 148. Formulation ID: RG10/229, formulation name: Dhatri Rasayana (nausdaru). Retrieved on Sep. 3, 2013.
Sodhala; Gadanigrahah ed, Ganga Sahaya Pandeya & Com. Indradeva Tripathi, Part -3 (Salakya-Pancakarma Khanda) Chaukhamba Sanskrit Sansthan (Varanasi), 3rd Edn. 1999, p. 27. Formulation ID: RG2/61, formulation name: Candadi Pralepa. Retrieved on Apr. 28, 2014.
Sodhala; Gadanigrahah ed, Ganga Sahaya Pandeya & Com.—Indradeva Tripathi, part-1 (Prayoga Khanda) Chaukhamba Sanskrit Sansthan, Varanasi, 3rd Edn., 1999 p. 392. Formulation ID: RS/992, formulation name: Rasayanaristah. Retrieved on Apr. 28, 2014.
Stenset et al., (2008) White matter lesion subtypes and cognitive deficits in patients with memory impairment. Dement Geriatr Cogn Disord 26(5):424-431.
Stern et al., (2003) Compositional variations in aged and heated Pistacia resin found in late bronze age Canaanite amphorae and bowls from amarne, Egypt. Archaeometry 45(3): 457-469.
Van Den Berg et al., (1998) Cis-1,4-poly-β-myrcene; the structure of the polymeric fraction of mastic resin (*Pistacia lentiscus* L.) elucidated. Tetrahedron Lett 39(17):2645-2648.
Vangasena; Vangasena—Commentator Shaligram Vaisya, Edited Shankar Lalji Jain; Khemraj Shrikrishna Das Prakashan, Bombay, Edn., 1996 p. 1031. Formulation ID: AK11/4412, formulation name: Varunyadi Gana. Retrieved on Apr. 28, 2014.
Watanabe et al., (2006) Cilostazol Protects Against Brain White Matter Damage and Cognitive Impairment in a Rat Model of Chronic Cerebral Hypoperfusion. Stroke 37(6):1539-1545.
Yousuf et al., (2005) Protective effect of Khamira Abresham Uood Mastagiwala against free radical induced damage in focal cerebral ischemia. J Ethnopharmacology 99(2):179-184.
Ziya Al-Din Abdullah Ibn Al-Baitar; Al-Jaam'e-li-Mufradaat-al-Advia-wal-Aghzia, vol. II (13th century AD), Matba Amra, Cairo, Egypt, 1874 AD pp. 174-175. Formulation ID: JA3/244, formulation name: Zaitoon. Retrieved on Jun. 10, 2014.
Database WPI Week 198835 Thomson Scientific, London, GB; AN 1988-246745.
Database EPODOC [online] European Patent Office, The Hague, NL; Apr. 19, 2002, Database accession No. GR1003868.
Aminuddaula Abul Farj Ibn Al-Quff Maseehi; Kitaab-al-U'mdah-fil-Jeraahat, Part II (13th century), p. 242. Formulation ID: MA2/646, formulation name: Roughan-e-Mastagi. Retrieved from Traditional Knowledge Digital Library (TKDL) on Feb. 27, 2018.
Aminuddaula Abul Farj Ibn Al-Quff Maseehi; Kitaab-al-U'mdah-fil-Jeraahat, Part II (13th century), pp. 248-249. Formulation ID: MA2/672, formulation name: Marham-e-Aswad. Retrieved from Traditional Knowledge Digital Library (TKDL) on Feb. 27, 2018.
Farkas et al., (2007) Permanent, bilateral common carotid artery occlusion in the rat: a model for chronic cerebral hypoperfusion-related neurodegenerative diseases. Brain Res Rev 54(1): 162-180.
Kandasamy Mudaliar, "Punuku Seelai", Athmarakshaamirtham, Pub: Ilakkana Achagam (1879), p. 640, Traditional knowledge Digital Library, Formulation ID. AM05/2509; 2 pages.

\* cited by examiner

```
NAME              J5K10.11.08
EXPNO                       1
PROCNO                      1
Date_                20081110
Time                     8.21
INSTRUM                 spect
PROBHD      5 mm Dual 13C/
PULPROG                    zg
TD                      32768
SOLVENT                 CDCl3
NS                          8
DS                          0
SWH               4194.631 Hz
FIDRES            0.128010 Hz
AQ               3.9059956 sec
RG                       71.8
DW                 119.200 usec
DE                   6.00 usec
TE                    297.2 K
D1              0.00100000 sec
TD0                         1

======== CHANNEL f1 ========
NUC1                       1H
P1                   9.00 usec
PL1                    -3.00 dB
SFO1            300.1319000 MHz
SI                      32768
SF              300.1300055 MHz
WDW                        EM
SSB                         0
LB                    0.00 Hz
GB                          0
PC                       0.50
```

Fig. 3, CONTINUED

```
NAME            J5K10.11.08
EXPNO                      2
PROCNO                     1
Date_               20081110
Time                    8.26
INSTRUM                spect
PROBHD    5 mm Dual 13C/
PULPROG                 zgdc
TD                     32768
SOLVENT                CDCl3
NS                      1808
DS                         0
SWH             19723.865 Hz
FIDRES           0.601925 Hz
AQ              0.8307188 sec
RG                  5792.6
DW                 25.350 usec
DE                  9.46 usec
TE                 297.2 K
D1             0.10000000 sec
d11            0.03000000 sec
TDO                        1
======== CHANNEL f1 ========
NUC1                     13C
P1                  3.00 usec
PL1                -5.00 dB
SFO1          75.4759867 MHz
======== CHANNEL f2 ========
CPDPRG2              waltz16
NUC2                      1H
PCPD2             100.00 usec
PL2                -6.00 dB
PL12               12.00 dB
SFO2         300.1312000 MHz
SI                     32768
SF            75.4677482 MHz
WDW                       EM
SSB                        0
LB                  5.00 Hz
GB                         0
PC                      1.00
```

Fig. 4, CONTINUED

```
NAME              J5K17.12.08
EXPNO                       2
PROCNO                      1
Date_                20081217
Time_                    9.06
INSTRUM                 spect
PROBHD     5 mm Dual 13C/
PULPROG                    zg
TD                      32768
SOLVENT                 CDCl3
NS                         24
DS                          0
SWH               4194.631 Hz
FIDRES            0.128010 Hz
AQ               3.9059956 sec
RG                       71.8
DW                 119.200 usec
DE                    6.00 usec
TE                    297.2 K
D1              0.00100000 sec
TDO                         1

======== CHANNEL f1 ========
NUC1                       1H
P1                    9.00 usec
PL1                  -3.00 dB
SFO1          300.1319000 MHz
SI                      32768
SF            300.1300075 MHz
WDW                        EM
SSB                         0
LB                    0.00 Hz
GB                          0
PC                       0.50
```

Fig. 6, CONTINUED

```
NAME          J5K17.12.08
EXPNO                   3
PROCNO                  1
Date_            20081217
Time                 9.11
INSTRUM             spect
PROBHD   5 mm Dual 13C/
PULPROG              zgdc
TD                  32768
SOLVENT             CDCl3
NS                    442
DS                      0
SWH          19723.865 Hz
FIDRES        0.601925 Hz
AQ           0.8307188 sec
RG               5792.6
DW              25.350 usec
DE               9.46 usec
TE              297.2 K
D1          0.10000000 sec
d11         0.03000000 sec
TD0                     1
======== CHANNEL f1 ========
NUC1                  13C
P1               3.00 usec
PL1             -5.00 dB
SFO1       75.4759867 MHz
======== CHANNEL f2 ========
CPDPRG2           waltz16
NUC2                   1H
PCPD2          100.00 usec
PL2             -6.00 dB
PL12            12.00 dB
SFO2      300.1312000 MHz
SI                  32768
SF         75.4677483 MHz
WDW                    EM
SSB                     0
LB               2.00 Hz
GB                      0
PC                   1.00
```

Fig. 7, CONTINUED

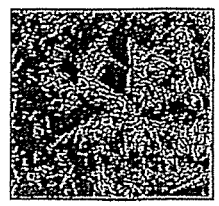 
Fig. 12A  Fig. 12B
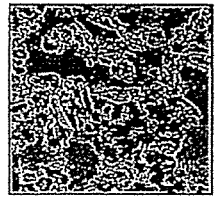 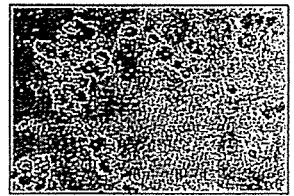
Fig. 12C  Fig. 12D

COMPOSITIONS OF POLYMERIC MYRCENE

CROSS REFERENCE TO RELATED APPLICATIONS

This application is a continuation of U.S. Ser. No. 14/226,293 filed Mar. 26, 2014, which is a continuation of U.S. patent application Ser. No. 13/254,380, filed Sep. 1, 2011, now U.S. Pat. No. 8,722,105, which is a 35 U.S.C. § 371 National Phase Entry Application from PCT/IL2010/000184, filed Mar. 4, 2010, and designating the United States, which claims the benefit of U.S. Patent Application No. 61/157,216 filed Mar. 4, 2009, all of which are incorporated herein in their entireties.

FIELD OF THE INVENTION

The invention relates to compositions isolated from mastic gum, and their therapeutic use. More particularly, the invention relates to compositions comprising an isolated fraction of polymeric myrcene and formulations which maintain the biological activity of the active polymer.

BACKGROUND OF THE INVENTION

The pursuit of new drug entities derived from plants and plant products for various therapeutic applications has its origins in antiquity and continues to the present. One such source is mastic, also known as gum mastic or mastic gum, which is a tree resin obtained as an exudate from *Pistacia lentiscus* L., a member of the family Anacardiaceae. Mastic was used in the ancient Mediterranean world for gastrointestinal disorders such as gastralgia, dyspepsia and peptic ulcer. Oral administration of mastic to human patients with duodenal ulcer and to experimental rats with induced gastric and duodenal ulcers has been disclosed to have therapeutic effects (Al-Habbal et al (1984) Clin Exp Pharmacop Physio 11(5):541-4; Said et al (1986) J Ethnopharmacol 15(3):271-8). While it has been disclosed that mastic has in vitro bactericidal effects against *Helicobacter pylori*, the etiologic agent causing peptide ulcer disease (Marone et al (2001) J Chemother 13:611-614), other reports disclose that mastic does not exert anti-bacterial activity upon administration to *H. pylori* positive human patients (Bebb et al (2003) J Antimicrob Chemother 52:522-23) or to experimentally infected mice (Loughlin et al (2003) J Antimicrob Chemother 51:367-371).

Greek Patent No. GR 1,003,541 discloses antimicrobial and antifungal action of the chios mastic oil extracted from the leaves, branches and fruit of *Pistacia lentiscus* var Chia.

Greek Patent No. GR 1,003,868 discloses use of a product derived from *Pistacia lentiscus* var. Chia as an antioxidant, as a wound healing inductor and as a cytostatic agent.

U.S. Patent Application Publication No 2005/0238740 discloses that certain fractions extracted from mastic resin exhibit anti-microbial and anti-cell proliferative activities. According to the disclosure, a first extract (termed "total fraction" or "whole extract") contains all the compounds of the mastic gum except the polymer resin; a second extract is an acid fraction containing all the triterpenic acids of the total fraction, and a third extract is a neutral fraction containing all the other terpenes of the total fraction. Additionally disclosed is an essential oil obtained by distillation which contains monoterpenes, inter alia, β-myrcene. The application discloses pharmaceutical formulations comprising any of the aforementioned total, acid or neutral fractions optionally combined with the essential oil, or synthetic equivalents thereof, or comprising isolated component products or synthetic equivalents thereof, as well as the use thereof in methods for treating microbial infections including *H. pylori, Propionibacterium, Staphylococcus, Pseudomonas,* and cell hyperproliferation.

Paraschos et al (2007), authored by some of the inventors of the aforementioned patent application, disclose preparation of a total mastic extract without polymer (TMEWP), prepared by polar solvent extraction of crude mastic and removal of the insoluble polymer poly-β-myrcene therefrom, and acidic and neutral fractions separated from TMEWP (Paraschos et al (2007) Antimicrob Agents Chemother 51(2):551-559). According to the disclosure, administration of TMEWP to *H. pylori* infected mice over a period of 3 months resulted in a 30-fold reduction of bacterial colonization, largely attributable to a particular compound purified from the acid fraction. The authors indicate that TMEWP was prepared since the high percentage of poly-β-myrcene in crude mastic preparations, as used in previous studies, was speculated to hinder potential in vivo activity during oral administration. The authors further disclose that removal of the poly-β-myrcene can produce an enhanced therapeutic moiety with anti-*H. pylori* activity.

EP Patent Application No. 1520585 discloses use of a product obtained from a plant of the genus *Pistacia* for the manufacture of a medicament for treating or preventing cancer. According to the disclosure, essential oils distilled from leaves, twigs, fruits, nuts and flowers of different *Pistacia* species contain a large number of monomeric terpene compounds in varying proportions inter alia β-myrcene. The application further discloses that the oils have activity against certain tumor cells lines such as colon and ovary adenocarcinomas, and that bornyl acetate was the only single component found to have anti-cancer activity.

International Patent Application Publication No. WO 2005/112967 discloses the purification from mastic of an anti-cancer compound having anti-proliferative effects, which is found in a soluble fraction obtained by suspending mastic in a solvent selected from a non-acidic, aliphatic hydrocarbon, an aqueous solution containing at least 25% of a water-soluble, non-acidic, aliphatic hydrocarbon, or a combination thereof, and removing the insoluble fraction. The application further discloses a method for treating cancer cells comprising administering a pharmaceutically effective amount of a fraction of mastic gum resin that inhibits growth of cancer cells. According to the disclosure, the anti-cancer compound is effective against various types of cancer cells, including human colon cancer cells.

Van der Berg et al (1998) disclose isolation and purification of the polymer fraction of mastic using extraction and size exclusion chromatography (Van der Berg et al (1998) Tetrahedron Lett 3:2645-2648). According to the disclosure, the polymer has a broad molecular weight distribution i.e. 20,000 to 100,000 Da, is formed from monomer units of 136 Da, and has the structure of 1,4-poly-β-myrcene, with cis- and trans-configurations at a ratio of 3:1. The authors assert that their disclosure is the first report of a naturally occurring polymer of a monoterpene.

Barra et al (2007) disclose extraction and gas chromatographic analysis of essential oil from *P. lentiscus* L. (Barra et al (2007) J Agric Food Chem 55(17):7093-7098). According to the disclosure, a total of 45 compounds were identified, including β-myrcene as one of the major compounds.

Marner et al (1991) disclose identification of various triterpenoids from gum mastic of *P. lentiscus* (Marner et al (1991) Phytochemistry, 30, 3709-3712).

U.S. Pat. No. 5,506,406 discloses mastic oil produced by dissolving mastic in an oil or fat, and filled in a soft capsule which optionally further contains an amphipathic substance such as chitin or chitosan. According to the disclosure, the capsule is effective for eliminating and inhibiting *H. pylori*, and for reducing the smell of feces. U.S. Pat. No. 5,637,290 discloses an oral hygiene product comprising the combination of a toothpaste and an ingredient selected from natural mastic, extracted mastic oil and synthetic mastic oil agents. Also disclosed is use of mastic for incorporation into suntan lotion, hair products and cosmetics.

U.S. Pat. No. 6,623,728 discloses cosmetic skin care emulsion compositions comprising from about 0.001 wt % to about 10 wt % solubilized gum mastic; a volatile water miscible solvent; and a cosmetically acceptable vehicle. According to the disclosure, the emulsion is preferably an oil-in-water emulsion, and preferred solvents include ethanol, methanol propanol, isopropyl alcohol and mixtures thereof. According to the disclosure, the same types of solvents are used to obtain the solubilized gum mastic.

U.S. Pat. No. 6,811,769 discloses an oral composition comprising an oil extract of mastic, such as that prepared with olive oil or palm oil; and an antiphlogistic, such as glycyrrhizic acid. According to the disclosure, the composition has antibacterial action against periodontal disease-related bacteria and against tooth decay-related bacteria.

U.S. Pat. No. 7,294,651 discloses use of isoprenoid compounds, inter alia, terpene compounds for inhibiting the production of exoproteins of Gram positive bacteria, such as Toxic Shock Syndrome Toxin-1 produced by *S. aureus*. According to the disclosure, suitable terpenes may be cyclic or acyclic, saturated or unsaturated, and also include polyterpenes. Also disclosed is the use of such compounds for preparing compositions which may be incorporated into aqueous solutions, such as vaginal cleaning formulations.

U.S. Pat. No. 4,564,718 discloses preparation of functionally terminated polymers, referred to as "liquid rubbers" having glass transition temperatures substantially less than room temperature, by polymerization of a terpene or oxygen derivative thereof having a double bond or conjugated double bond available for polymerization, with an initiator which provides the desired functional termination. According to the disclosure, the polymers preferably have a molecular weight of 500 to 20,000, and preferred acyclic monoterpenes for preparation thereof are inter alia β-myrcene. The patent discloses preparation of polymeric myrcene of molecular weight of about 2000 and of about 4000. The patent further discloses that the polymers of the invention may be further reacted with other reagents to provide elastomers, sealants or adhesives, or they may be used as rubber toughening agents. Further disclosed is preparation of hydroxy-terminated polymyrcene from myrcene, and use thereof to prepare a polyurethane elastomer.

Newmark et al J. Polymer Sci. 26, 71-77 (1988) discloses synthesis of polymyrcene having an observed molecular weight of 87,000 and a calculated molecular weight of 46,000.

U.S. Pat. No. 4,374,957 discloses a tacky thermoplastic elastomeric linear triblock polymer corresponding to the formula A-B-A, wherein A is a nonelastic linear homopolymer block of a monovinyl aromatic hydrocarbon having an average molecular weight between 10,000 and 60,000 and a glass transition temperature above 70° C., and wherein B is an elastomeric homopolymeric block of myrcene having an average molecular weight between 50,000 and 200,000 and a glass transition temperature below about −40° C.

U.S. Pat. No. 5,759,569 discloses biodegradable compostable articles that at least partially comprise certain trans-polymers, wherein the polymers have a weight average molecular weight of at least about 20,000 and are made by polymerizing a monomer component that comprises: (1) from about 70 to 100 mole % 1,3-dienes inter alia β-myrcene; and (2) up to about 30 mole % other compatible co monomers. According to the disclosure, the articles include inter alia packaging materials; disposable absorbent articles (e.g., diapers, sanitary napkins); garment articles such as protective clothing, surgical drapes, surgical gowns, surgical sheets; woven, knitted and non-woven fabrics; surgical sponges, tampon applicators, disposable syringes and containers.

U.S. Pat. Nos. 7,232,872 and 7,214,750 disclose a polymerization process comprising contacting one or more monomer(s) inter alia myrcene, one or more Lewis acid(s), one or more initiator(s), and a diluent comprising one or more hydrofluorocarbon(s) in a reactor.

U.S. Patent Application Publication No 2007/0179260 and U.S. Pat. No. 7,417,103 disclose 3,4-isoprene-based polymers with high regioregularity and a method for producing same. According to these disclosures, the number average molecular weight of the polymer is 5000 to 6,000,000, and the polymer may also include units of 1,4-isoprenes such as myrcene. According to the disclosure, the polymer is suitable for use as a plastic material due to its mechanical and thermal durability.

The prior art does not contain any teaching or suggestion of the use of an isolated fraction of polymeric myrcene, whether that derived from mastic, or that chemically synthesized, as an active ingredient in a pharmaceutical composition or in a therapeutic application. The prior art does not teach or suggest use of an isolated fraction of polymeric myrcene in a composition for treating neurological conditions or skin disorders.

SUMMARY OF THE INVENTION

The present invention provides pharmaceutical compositions comprising polymeric forms of the monoterpene compound known as myrcene, which exhibit a variety of beneficial biological activities which may be exploited for therapeutic applications. More specifically, compositions comprising isolated fractions of polymeric myrcene, including that chemically synthesized and that derived from plant sources such as mastic gum, are now disclosed to have activity in neuroprotection, tissue regeneration and wound and tissue repair.

The compositions disclosed herein may be prepared by solvent extraction of certain plant material, such as mastic gum, in so as to obtain isolated fractions which are soluble in both polar and non-polar solvents, and are depleted of various monomeric terpene compounds which interfere with the desired biological activity.

The teachings of the present invention have been exemplified with mastic gum extracts prepared by a two-step extraction procedure, so as to obtain a fraction that is soluble in both a polar solvent and a non-polar solvent, and wherein material from the mastic gum that is soluble in the polar solvent but remains insoluble in the non-polar solvent is eliminated. The present invention has also been exemplified both with polymeric myrcene isolated from a natural source i.e. tree resin mastic, and with chemically synthesized polymeric myrcene having the molecular weight in the same range and chemical structure as that of the corresponding polymer isolated from mastic.

Moreover, the teachings of the present invention are particularly surprising and unexpected over teachings which disclose the use of mastic gum extract fractions from which polymeric myrcene has been removed. Furthermore, the prior art asserts that polymeric fractions derived from mastic are not therapeutically useful, and that the presence of polymeric myrcene in therapeutic compositions actually inhibits the beneficial biological activities and bioavailability of the active compounds. The prior art teaches that the active compounds in mastic gum correspond to various low molecular weight terpene-type molecules, inter alia monomeric myrcene. However, the inventors of the present invention have surprisingly found, and contrary to the teachings of the prior art, that monomeric myrcene, small oligomeric forms of myrcene, and certain other low molecular weight terpenes interfere with and block the activity of polymeric myrcene in inducing cell differentiation.

Without wishing to be bound by any particular theory or mechanism of action, the activity of polymeric myrcene for induction of neuronal cell differentiation, as disclosed herein, renders the present invention useful for reformation of inter-neuronal junctions and overcoming defective inter-neuronal communication in brain and neural tissue affected by pathologies associated with inadequate synaptic formation. This pathology underlies many nervous system pathologies, including for example Alzheimer's disease. The invention is further useful for promoting wound healing and rejuvenation of a large number of cells and tissues.

As used herein "polymeric myrcene" encompasses polymeric forms of myrcene having a degree of polymerization of at least 6. Polymeric myrcene includes without limitation, polymeric β-myrcene (poly-β-myrcene), polymeric α-myrcene (poly-α-myrcene), homopolymers thereof and heteropolymers (also known as copolymers) which contain myrcene subunits. Also included are geometric isomers, optical isomers and diastereoisomers of polymeric myrcene compounds.

It is to be understood explicitly that the scope of the present invention does not include myrcene in its monomeric form, such as β-myrcene and α-myrcene, as active ingredients of the fractions and compositions disclosed herein.

As used herein, β-myrcene refers to 7-methyl-3-methylene-1,6-octadiene and α-myrcene refers to the structural isomer 2-methyl-6-methylene-1,7-octadiene.

It is to be further understood that the biological activity of the fractions and compositions disclosed herein is inhibited by the presence of certain monomeric and small oligomeric forms of various terpenes.

According to a first aspect, the present invention provides a composition comprising an effective amount of an isolated fraction of mastic gum, wherein the fraction is characterized in that it is soluble in at least one polar organic solvent and in at least one non-polar organic solvent, and wherein said fraction is substantially devoid of compounds which are soluble in said polar organic solvent but insoluble in said non-polar organic solvent.

In a particular embodiment, the composition is obtained by a process comprising the steps of:
 (a) treating mastic gum with a polar organic solvent;
 (b) isolating a fraction soluble in said polar organic solvent;
 (c) optionally removing said polar organic solvent;
 (d) treating the soluble fraction obtained in step (b) or (c) with a non-polar organic solvent, (e) isolating a fraction soluble in said nonpolar organic solvent; and
 (f) optionally removing said nonpolar organic solvent;

wherein steps (d) to (f) may precede steps (a) to (c).

In particular embodiments, steps (a) to (c) are carried out prior to steps (d) to (f); or steps (d) to (f) are carried out prior to steps (a) to (c). In particular embodiments, (a) to (c) and/or steps (d) to (f) are repeated for a multiplicity of cycles.

In a particular embodiment, either or both of steps (c) and (f) comprise removing the solvent by a means selected from the group consisting of rotary evaporation, application of high vacuum and a combination thereof. In a particular embodiment, the process further comprises the step of size fractionating the fraction obtained by said process.

Polar organic solvents suitable for use in the invention may be selected from an alcohol, an ether, an ester, an amide, an aldehyde, a ketone, a nitrile, and combinations thereof.

Specific examples of suitable polar organic solvents include methanol, ethanol, propanol, isopropanol, 1-butanol, 2-butanol, sec-butanol, t-butanol, 1-pentanol, 2-pentanol, 3-pentanol, neopentanol, 3-methyl-1-butanol, 2-methyl-1-butanol, 3-methyl-2-butanol, 2-methyl-2-butanol, ethyleneglycol, ethyleneglycol monomethyl ether, diethyl ether, methylethyl ether, ethylpropyl ether, methylpropyl ether, 1,2-dimethoxyethane, tetrahydrofuran, dihydrofuran, furan, pyran, dihydropyran, tetrahydropyran, methyl acetate, ethyl acetate, propyl acetate, acetaldehyde, methylformate, ethylformate, ethyl propionate, methyl propionate, dichloromethane, chloroform, dimethylformamide, acetamide, dimethylacetamide, N-methylpyrrolidone, acetone, ethylmethyl ketone, diethyl ketone, acetonitrile, propionitrile, and combinations thereof.

In particular embodiments, the polar organic solvent is ethanol.

Non-polar organic solvents suitable for use in the invention may be selected from acyclic or cyclic, saturated or unsaturated aliphatic hydrocarbons and aromatic hydrocarbons, each of which is optionally substituted by one or more halogens, and combinations thereof. In particular embodiments, the non-polar organic solvent is selected from C5-C10 alkanes, C5-C10 cycloalkanes, C6-C14 aromatic hydrocarbons and C7-C14 perfluoroalkanes, and combinations thereof.

In particular embodiments, the non-polar organic solvent is selected from pentanes, hexanes, heptanes, octanes, nonanes, decanes, cyclopentane, cyclohexane, cycloheptane, benzene, toluene, xylene, and isomers and mixtures thereof.

In particular embodiments, the C5-C10 alkane is selected from the group consisting of pentane, hexane, heptane, octane, nonane, decane, cyclohexane, and isomers and mixtures thereof.

In particular embodiments, the non-polar organic solvent is hexane.

In a particular embodiment, the polar organic solvent comprises ethanol and the non-polar organic solvent comprises hexane.

In a particular embodiment, the composition is substantially devoid of terpene compounds which are soluble in said polar organic solvent and insoluble in said non-polar organic solvent. In a particular embodiment, the terpene compounds are monomeric terpene compounds. In a particular embodiment, the terpene compounds are selected from β-myrcene, α-myrcene, cis-α-ocimene, dihydromyrcene, limonene, α-pinene, β-pinene and combinations thereof.

In a particular embodiment, the composition comprises from about 0.01 to about 25% (w/w) of the isolated fraction of mastic gum, based on the total weight of the composition. In a particular embodiment, the composition comprises from about 0.01 to about 12% (w/w) of the isolated fraction of mastic gum, based on the total weight of the composition.

In a particular embodiment, the isolated fraction of gum mastic comprises polymeric myrcene.

In another aspect the invention provides a pharmaceutical composition comprising a therapeutically effective amount of an isolated fraction of polymeric myrcene, and a pharmaceutically acceptable carrier.

In a particular embodiment, the composition comprises from about 0.01 to about 12% (w/w) polymeric myrcene, based on the total weight of the composition.

In particular embodiments, the polymeric myrcene is selected from the group consisting of polymeric β-myrcene (poly-β-myrcene), polymeric α-myrcene (poly-α-myrcene), myrcene copolymers and combinations thereof. In particular embodiments, the poly-β-myrcene is selected from the group consisting of 1,4-poly-β-myrcene, 3,4-poly-β-myrcene, 1,2-poly-β-myrcene and combinations thereof. In particular embodiments, the polymeric myrcene comprises a myrcene isomer selected from the group consisting of a cis isomer, a trans isomer and combinations thereof. In particular embodiments, the 1,4-poly-β-myrcene is selected from the group consisting of cis-1,4-poly-β-myrcene, trans-1,4-poly-β-myrcene and combinations thereof. In particular embodiments, the polymeric myrcene comprises cis-1,4-poly-β-myrcene. In particular embodiments, the polymeric myrcene has a cyclic conformation. In particular embodiments, the polymeric myrcene has a branched conformation.

In a particular embodiment, the polymeric myrcene has a degree of polymerization in the range of at least about 6 to about 1800. In a particular embodiment, the degree of polymerization is at least about 10. In a particular embodiment, the degree of polymerization is at least about 15. In a particular embodiment, the degree of polymerization is at least about 25. In a particular embodiment, the degree of polymerization is at least about 35. In a particular embodiment, the degree of polymerization is in the range of about 6 to about 30. In a particular embodiment, the degree of polymerization is in the range of about 30 to about 500, for example, in the range of about 33 to about 150.

Each possibility represents a separate embodiment of the invention.

In a particular embodiment, the polymeric myrcene has a number average molecular weight of at least about 800. In a particular embodiment, the number average molecular weight is at least about 1,000. In a particular embodiment, the number average molecular weight is at least about 2000. In a particular embodiment, the number average molecular weight is at least about 3000. In a particular embodiment, the number average molecular weight is at least about 5000. In a particular embodiment, the polymeric myrcene has a number average molecular weight in the range from at least about 800 to about 100,000. In particular embodiments, the number average molecular weight is in a range selected from the group consisting of: at least about 800 to about 80,000; at least about 800 to about 50,000; at least about 800 to about 20,000; at least about 800 to about 10,000; at least about 800 to about 5000; at least about 1,000 to at least about 50,000; at least about 1,000 to about 10,000; at least about 1,000 to about 5000; about 5000 to about 10,000; about 10,000 to about 15,000; about 5000 to about 20,000; about 15,000 to about 30,000; about 25,000 to about 40,000; about 35,000 to about 50,000; about 45,000 to about 60,000; about 55,000 to about 70,000; about 65,000 to about 80,000; about 75,000 to about 90,000; about 85,000 to about 100,000; or any combinations and sub-ranges thereof. In a particular embodiment, the polymeric myrcene has a number average molecular weight in the range from about 5,000 to about 20,000.

Each possibility represents a separate embodiment of the invention.

It is to be understood that the composition may comprise different molecular weight fractions of polymeric myrcene, for example in the range from at least about 800 to about 100,000, or various combinations thereof. In a particular embodiment, the polymeric myrcene has a polydispersity index less than 5.

In a particular embodiment, the polymeric myrcene is the product of a chemical synthesis. In a particular embodiment, the chemical synthesis comprises use of monomeric myrcene as a substrate. In a particular embodiment, the substrate is β-myrcene. In a particular embodiment, the β-myrcene substrate is derived from a plant.

In a particular embodiment, the product of the chemical synthesis comprises cis-1,4-poly-β-myrcene. In a particular embodiment, the chemical synthesis comprises an anionic polymerization reaction. In a particular embodiment, the chemical synthesis further comprises dissolving the polymeric myrcene obtained therefrom in a hydrophobic carrier, such as at least one vegetable oil.

In a particular embodiment, the isolated fraction of polymeric myrcene is derived from a natural source. Natural sources include plants classified in the family Anacardiaceae. In a particular embodiment, gum mastic is from a plant classified in the family Anacardiaceae. Suitable plants include those classified in a genus selected from the group consisting of *Pistacia*, *Pinus*, *Picea*, *Juniperus*, *Alsies*, *Larix*, *Antirrhinum*, *Boswellia*, *Citrus* and *Gynura*. In a particular embodiment, the species of *Pistacia* is selected from the group consisting of *P. lentiscus*, *P. atlantica*, *P. palestina*, *P. saportae*, *P. terebinthus*, *P. vera* and *P. integerrima*. In a particular embodiment, the species of *Pistacia* is *Pistacia lentiscus* L. In a particular embodiment, the natural source is a plant material selected from the group consisting of resin, leaves, twigs, roots, flowers, seeds, buds, bark, nuts and roots. In a particular embodiment, the natural source is a plant classified in a genus selected from the group consisting of *Ocimum*, *Laurus* and *Lavendula*.

In a particular embodiment, the isolated fraction of polymeric myrcene is obtained by a process comprising the steps of:
(a) contacting plant material with at least one polar organic solvent;
(b) isolating a fraction which is soluble in the at least one polar organic solvent
(c) optionally removing said polar organic solvent;
(d) treating the soluble fraction obtained in step (b) or (c) with at least one non-polar organic solvent;
(e) isolating a fraction soluble in said nonpolar organic solvent; and
(f) optionally removing said nonpolar organic solvent;
wherein steps (d) to (f) may precede steps (a) to (c), and wherein steps (a) to (c) and steps (d) to (f) are each independently carried out for a number of cycles; so as to obtain an isolated fraction of polymeric myrcene.

In particular embodiments, the isolated fraction of polymeric myrcene has a degree of purity of at least about 80% (w/w). The isolated fraction of polymeric myrcene may have a degree of purity of at least about 85% (w/w). In particular embodiments, the isolated fraction of polymeric myrcene has a degree of purity of at least about 90% (w/w), or at least about 93%, or at least about 95%, or at least about 97%, or at least about 98% or at least about 99%.

In a particular embodiment, the isolated fraction of polymeric myrcene has a degree of purity of at least 80%, and the polymeric myrcene has a degree of polymerization of at least 6.

In a particular embodiment, the isolated fraction of polymeric myrcene has a degree of purity of at least 90%, and the polymeric myrcene has a degree of polymerization of at least 10.

In a particular embodiment, the isolated fraction of polymeric myrcene comprises at least 90% (w/w) of cis-1,4-poly-β-myrcene. In a particular embodiment, the isolated fraction of polymeric myrcene comprises a mixture of cis-1,4-poly-β-myrcene and trans-1,4-poly-β-myrcene, wherein the mixture comprises at least 50% (w/w) of cis-1,4-poly-β-myrcene. In a particular embodiment, the isolated fraction of polymeric myrcene comprises at least 90% (w/w) of cis-1,4-poly-β-myrcene having a number average molecular weight of at least 800, or at least 1,000, or at least 5,000 or at least 10,000. In a particular embodiment, the isolated fraction of polymeric myrcene comprises at least 80% (w/w) of cis-1,4-poly-β-myrcene having a number average molecular weight in the range from about 800 to about 5,000. In a particular embodiment, the isolated fraction of polymeric myrcene comprises at least 90% (w/w) of cis-1,4-poly-β-myrcene having a number average molecular weight in the range from about 1,000 to about 10,000. In a particular embodiment, the isolated fraction of polymeric myrcene comprises at least 90% (w/w) of cis-1, 4-poly-β-myrcene having a number average molecular weight in the range from about 5,000 to about 20,000.

In a particular embodiment, the isolated fraction of polymeric myrcene comprises at least 90% (w/w) of cis-1,4-poly-β-myrcene having a number average molecular weight in the range from about 10,000 to about 20,000. In a particular embodiment, the isolated fraction of polymeric myrcene comprises at least 90% (w/w) of cis-1,4-poly-β-myrcene having a number average molecular weight in the range from about 20,000 to about 30,000. In a particular embodiment, the isolated fraction of polymeric myrcene comprises at least 90% (w/w) of cis-1,4-poly-β-myrcene having a number average molecular weight in the range from about 30,000 to about 50,000 In a particular embodiment, the isolated fraction of polymeric myrcene comprises at least 90% (w/w) of cis-1,4-poly-β-myrcene having a number average molecular weight in the range from about 50,000 to about 80,000.

In particular embodiments, the composition comprises less than about 10% (w/w), and more preferably, less than about 5% (w/w), of terpene compounds which are soluble in a polar organic solvent and insoluble in a non-polar organic solvent. In particular embodiments, the composition is substantially devoid of terpene compounds which are soluble in a polar organic solvent and insoluble in a non-polar organic solvent. In particular embodiments, the composition comprises less than about 10% (w/w), and more preferably, less than about 5% (w/w), of monomeric terpene compounds. In a particular embodiment, the composition is substantially devoid of myrcene monomers.

As referred to herein, terpene compounds include monomeric and oligomeric forms of terpene compounds, including those variously classified as monoterpenes, diterpenes, sequiterpenes, triterpenes and tetraterpenes, including their acid, aldehyde and alcohol forms. In a particular embodiment, the composition comprises less than about 10% (w/w), and more preferably, less than about 5% (w/w), of a terpene compound selected from the group consisting of: β-myrcene, α-myrcene, cis-α-ocimene, dihydromyrcene, limonene, α-pinene, β-pinene and combinations thereof.

In a particular embodiment, the isolated fraction of polymeric myrcene is derived from a plant and the composition is substantially devoid of myrcene monomers and myrcene oligomeric forms having a degree of polymerization less than about 6. In a particular embodiment, the isolated fraction of polymeric myrcene is derived from a plant and the composition is substantially devoid of terpene compounds which are soluble in at least one polar organic solvent and insoluble in at least one non-polar organic solvent.

In a particular embodiment, the isolated fraction of polymeric myrcene is the product of a chemical synthesis and the composition is substantially devoid of myrcene monomers and myrcene oligomeric forms having a degree of polymerization less than about 6. In a particular embodiment, the isolated fraction of polymeric myrcene is the product of a chemical synthesis and the composition is substantially devoid of terpene compounds which are soluble in a polar organic solvent and insoluble in a non-polar solvent.

According to another aspect the present invention discloses a pharmaceutical composition comprising a synthetic polymeric myrcene wherein the polymeric myrcene has a number average molecular weight in the range of at least about 800 up to about 50,000, and wherein the isolated fraction of polymeric myrcene has a degree of purity of at least 80%.

In a particular embodiment, the pharmaceutically acceptable carrier comprises a hydrophobic carrier. In a particular embodiment, the hydrophobic carrier comprises at least one oil. In a particular embodiment, the oil is selected from the group consisting of a mineral oil, a vegetable oil and combinations thereof. In a particular embodiment, the vegetable oil is selected from the group consisting of almond oil, canola oil, coconut oil, corn oil, cottonseed oil, grape seed oil, olive oil peanut oil, saffron oil, sesame oil, soybean oil, and combinations thereof. In a particular embodiment, the mineral oil is light mineral oil. In a particular embodiment, the hydrophobic carrier comprises at least one wax. In a particular embodiment, the hydrophobic carrier comprises a combination of at least one oil and at least one wax.

In various embodiments, a composition according to the invention is in a form suitable for administration by a route selected from the group consisting of oral, topical, parenteral and transdermal.

In particular embodiments, the composition is in a form suitable for administration by injection. In various embodiments, the composition is a parenteral formulation for administration by a route selected from the group consisting of intravenous, intramuscular, subcutaneous, intradermal, intraperitoneal, intraarterial, intracerebral, intracerebroventricular, intraosseus and intrathecal. In various embodiments, the composition is a topical formulation for administration by a route selected from the group consisting of dermal, vaginal, rectal, inhalation, intranasal, ocular, auricular and buccal.

In particular embodiments, the composition is in a form suitable for cosmetic or dermatologic administration.

In particular embodiments, the pharmaceutical composition is in a form selected from the group consisting of a capsule, a tablet, a liposome, a suppository, a suspension, an ointment, a cream, a lotion, a solution, an emulsion, a film, a cement, a powder, a glue, an aerosol and a spray. In a particular embodiment, the capsule is selected from the group consisting of a hard gelatin capsule and a soft gelatin capsule. In a particular embodiment, the emulsion is a nanoemulsion or a microemulsion.

In particular embodiments, the formulation comprises at least one of an inclusion complex, a nanoemulsion, a microemulsion, a powder, a lipid raft, a lipid microparticle, a dendrimer and a liposome. In a particular embodiment, the inclusion complex comprises at least one cyclodextrin. In a particular embodiment, the at least one cyclodextrin comprises hydroxypropyl-β-cyclodextrin. In a particular embodiment, the nanoemulsion comprises droplets having average particle size of less than 800 nm. In a particular embodiment, the droplets have average particle size of less than 500 nm. In a particular embodiment, the droplets have average particle size of less than 200 nm. In a particular embodiment, the powder is a spray dried powder. In a particular embodiment, the liposome comprises a multilamellar vesicle. In a particular embodiment, the microemulsion comprises a non-ionic surfactant. In a particular embodiment, the non-ionic surfactant is selected from the group consisting of a polyoxyl castor oil, a polyoxyethylene sorbitan fatty acid ester (polysorbates), a poloxamer, a vitamin E derivative, a polyoxyethylene alkyl ether, a polyoxyethylene sterate, or saturated polyglycolyzed glyceride or combinations thereof.

In a particular embodiment, the composition is disposed on the article of manufacture in the form of a coating. In a particular embodiment, the article of manufacture comprises a vessel, wherein the composition is disposed within the vessel. In a particular embodiment, the article of manufacture is selected from the group consisting of a fabric article, a diaper, a wound dressing, a medical device, a needle or plurality of needles, a microneedle or plurality of microneedles, an injection device and a spray dispenser. In a particular embodiment, the article of manufacture comprises a plurality of microneedles. In particular embodiments, the medical device is selected from the group consisting of a prosthetic, an artificial organ or component thereof, a valve, a catheter, a tube, a stent, an artificial membrane, a pacemaker, a sensor, an endoscope, an imaging device, a pump, a wire and an implant. In a particular embodiment, the implant is selected from the group consisting of a cardiac implant, a cochlear implant, a corneal implant, a cranial implant, a dental implant, a maxillofacial implant, an organ implant, an orthopedic implant, a vascular implant, an intraarticular implant and a breast implant.

In a particular embodiment, the composition is suitable for administration by a means selected from the group consisting of electroporation, sonication, radio frequency, pressurized spray and combinations thereof.

In a particular embodiment, the composition is for treating impaired neurological function. In a particular embodiment, the impaired neurological function comprises a decrease in a function selected from the group consisting of cognitive function, sensory function, motor function and combinations thereof. In particular embodiments, the impaired neurological function is associated with a condition or disease, including for example, impaired neurological function is associated with a condition or disease, including for example, trauma, vascular dementia, senile dementia, Alzheimer's disease, amyotrophic lateral sclerosis (ALS), multiple sclerosis, Parkinson's disease, stroke, schizophrenia, bipolar disorder, depression, obesity, anorexia, cachexia an infection, and an immunological disorder. In a particular embodiment, the impaired neurological function is due to exposure to a drug, such as an anesthetic.

In a particular embodiment, the composition is for treating a skin or scalp disorder selected from the group consisting of alopecia, eczema, psoriasis, seborrheic keratosis and seborrhea. Skin and scalp disclosers include disorders of skin, scalp and hair appendages, including for example, nails and hair follicles. In a particular embodiment, the skin disorder is a skin wound, including for example, a venous leg ulcer, a pressure ulcer, a diabetic foot ulcer, a burn, an amputation wound, a decubitus ulcer (bed sore), a split-skin donor graft, a skin graft donor site, a medical device implantation site, a bite wound, a frostbite wound, a puncture wound, a shrapnel wound, a dermabrasion, a contusion, an infection, a wound and a surgical wound.

In a particular embodiment, the composition is for inducing or promoting tissue tissue repair. As used herein, tissue repair encompasses induction and promotion of tissue regeneration, including of neural tissues.

In a particular embodiment, the composition is for inducing or promoting tissue tissue repair following an injury or insult. In a particular embodiment, the injury or insult is selected from the group consisting of a myocardial infarction, a pulmonary embolism, a cerebral infarction, peripheral artery occlusive disease, a hernia, a splenic infarction, a venous ulcer, an axotomy, a retinal detachment, an infection and a surgical procedure.

It is to be understood explicitly that the scope of the present invention encompasses shorter and longer forms of polymeric myrcene, including synthetic and semi-synthetic forms, including myrcene copolymers, and derivatives substituted with various functionalities, and conjugates with additional molecules, as are known in the art, with the stipulation that these variants and modifications preserve the therapeutic capacity of the polymeric myrcene in the context of the methods of the present invention.

Other objects, features and advantages of the present invention will become clear from the following description and drawings.

BRIEF DESCRIPTION OF THE DRAWINGS

FIG. 8A, control cultures treated with oil vehicle; FIG. 8B, test cultures 48 hours after RPh-1 (0.1%; 1 mg/ml) administration and incubation; FIG. 8C, test cultures 4872 hours after RPh-1 (0.25%; 2.5 mg/ml) administration and incubation; FIG. 8D test cultures 72 hours after RPh-1 (0.25%; 2.5 mg/ml) administration and incubation.

FIG. 11A, differentiation grade 3; FIG. 11B, differentiation grade 4; FIG. 11C, differentiation grade 5.

FIGS. 12A-D show the effect of RPh-1 on human melanoma cells. FIG. 12A, oil vehicle treated control cells; FIG. 12B, cells treated with RPh-1 (5 µL) after 48 hours incubation, FIG. 12C, cells treated with RPh-1 (2 µL) after 48 hours incubation; FIG. 12D, cells treated with RPh-1 (5 µL) after 72 hours incubation.

FIG. 13A, differentiation induced with Fraction 18.1; FIG. 13B, differentiation induced with Fraction 18.2.

FIG. 14A, prior to treatment; FIG. 14B, following 2 weeks of treatment.

Figure 16A:
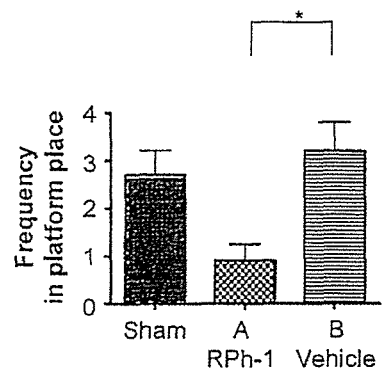
FIGS. 16A-G show the effect of RPh-1 on recovery from cerebral hypoperfusion in a vascular dementia rat model, as assessed by the Morris water maze test.
Figure 16B:
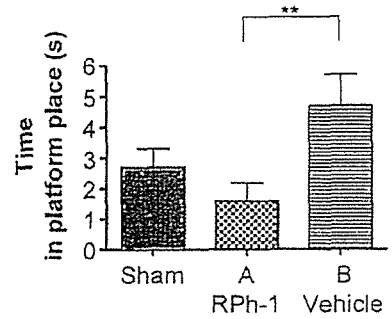
Figure 16C:
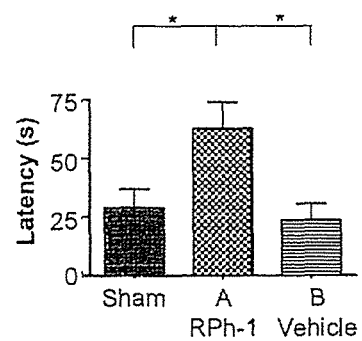
Figure 16D:
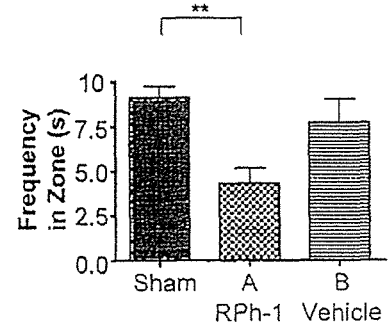
Figure 16E:
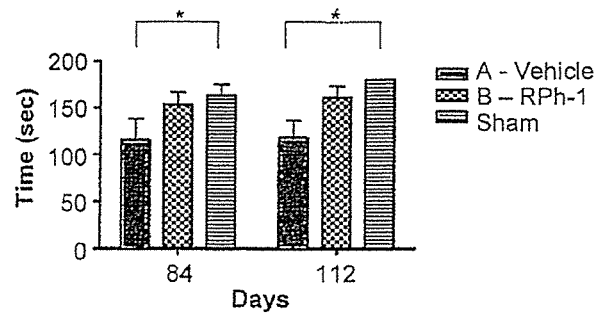
Figure 16F:
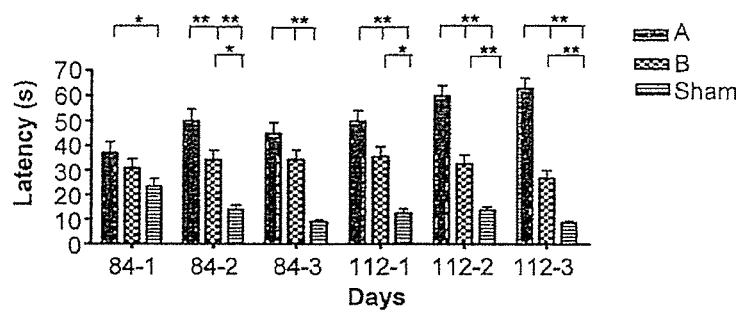
Figure 16G:
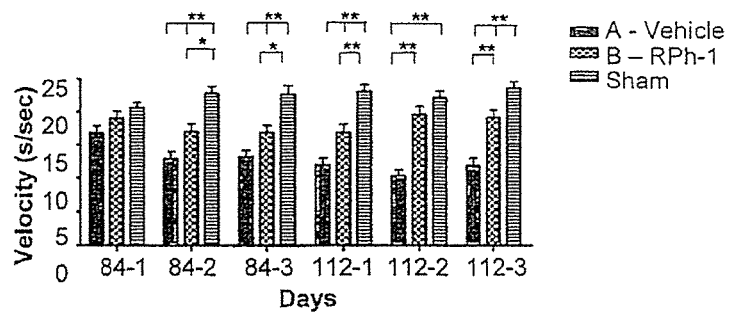

Performance of RPh-1-treated animals (Group A; cross-hatched bars), vehicle treated animals (Group B; horizontally striped bars) and in sham control animals (filled bars) were tested for frequency in platform location (FIG. 16A); the time spent in platform area (FIG. 16B); the latency to find the platform (FIG. 16C); the frequency in zone 1 location (FIG. 16D); the time spent in light part (FIG. 16E); the latency to find the platform (FIG. 16F); and the velocity (FIG. 16G).

Figure 17A:
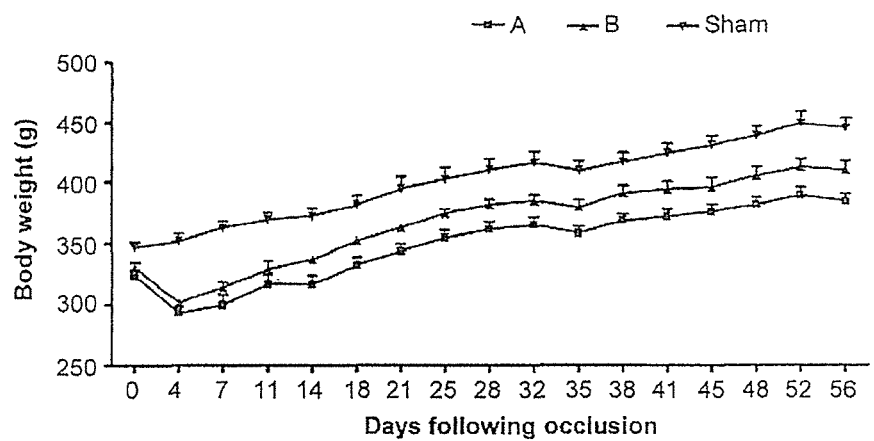
Figure 17B:
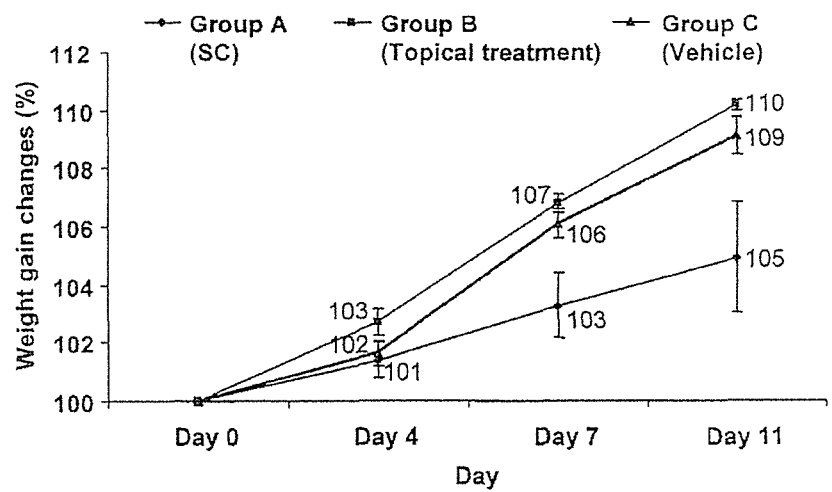

FIGS. 17A-B show the effect of RPh-1 on weight gain:

FIG. 17A shows weight gain in animals after cerebral hypoperfusion in a vascular dementia rat model. Weight of Group B animals (RPh-1 treated; triangle symbols) is recovering significantly faster then Group A animals (vehicle treated; square symbols).

FIG. 17B shows weight gain of obese mice (ob/ob) following treatment with RPh-1, either by subcutaneous administration (Group A; diamond symbols) or by topical administration (Group B; square symbols), or treatment with vehicle alone (Group C; triangle symbols). Mice of GroupS B and C gained 10.2% and 9.1% respectively. The rate of body weight gain in all groups as expressed by the slopes was similar (p=0.07 (A vs. B), 0.08 (A vs. C) and 0.43 (B vs. C).

Figure 18A:
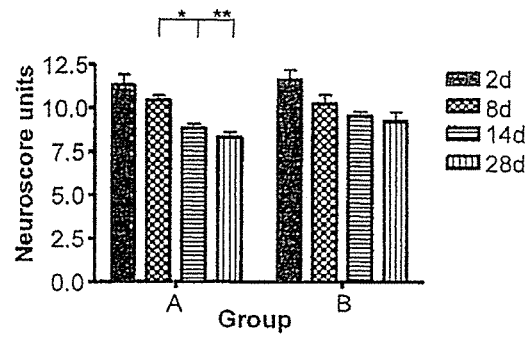
Figure 18B:
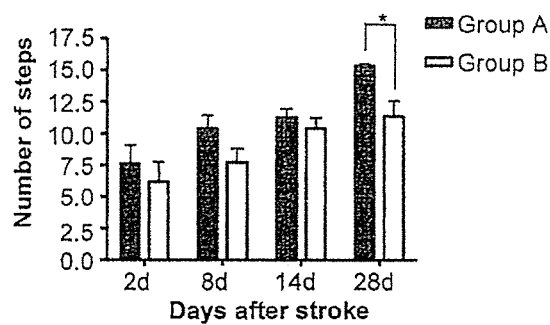
Figure 18C:
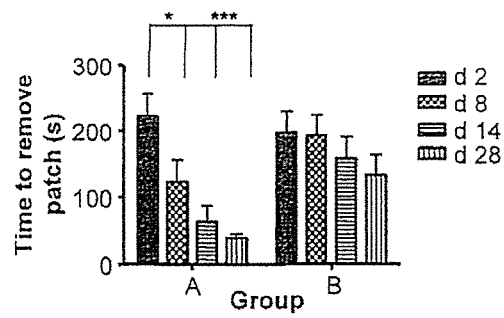

FIGS. 18A-C show the effect of RPh-1 on recovery from transient middle cerebral artery occlusion (tMCAO) in a rat stroke model:

FIG. 18A shows neuro-muscular score (Neuroscore) at various time points in days (d) as indicated, following MCAO in rats treated with RPh-1 (Group A) or with vehicle (Group B). Significant differences were seen only in Group A, between day 8 and day 14, and between day 8 and day 28.

FIG. 18B shows the results of stepping test at various time points following MCAO in rats treated with RPh-1 (Group A; black bars) or with vehicle (Group B; open bars) treatment. Significant differences were found between the two groups only on day 28.

FIG. 18C shows the results of adhesive removal test at various time points in days (d) as indicated, following MCAO in rats treated with RPh-1 (Group A) or with vehicle (Group B). Significant differences were seen only in Group A, between day 2 and the other days.

Figure 19:
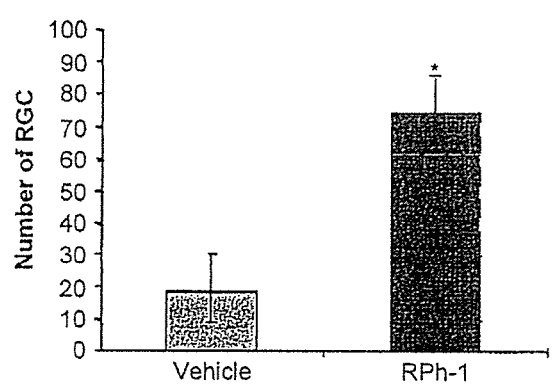

FIG. 19 shows the average number of surviving Retinal Ganglion Cells (RGC) following axotomy of the optic nerve in RPh-1 treated and control-treated rats.

Figure 20A:
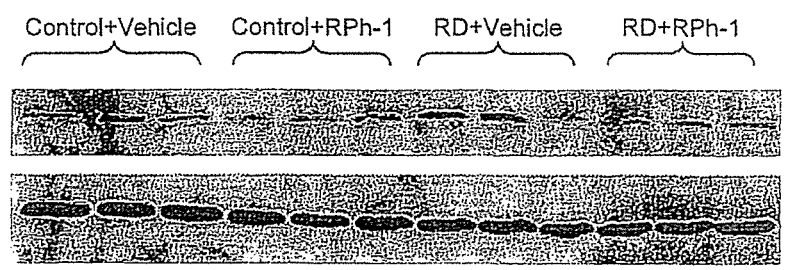
Figure 20B:
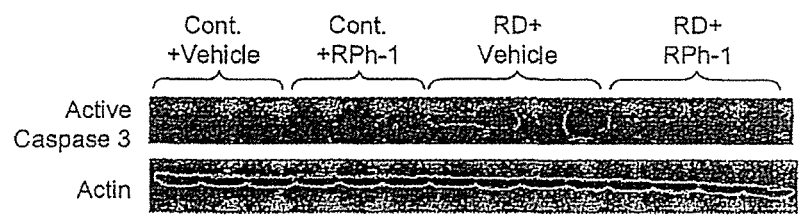

FIGS. 20A-B shows Western blot analysis of expression of SEMA3 (FIG. 20A) and caspase-3 (FIG. 20B) in detached retinas (RD) and non-injured retinas (control) from animals treated with RPh-1 or vehicle following retinal detachment.

DETAILED DESCRIPTION OF THE INVENTION

The inventor of the present invention has surprisingly found that isolated fractions of mastic gum have activity in ameliorating impaired neurological function, healing of skin and scalp disorders and wounds, and in promoting tissue repair. Such fractions are known to contain polymeric myrcene. Furthermore, it has also been surprisingly found that purified fractions of polymeric myrcene exhibit the same biological activities as that observed with isolated fractions of mastic gum. The aforementioned biological activities of polymeric myrcene have been demonstrated both with that derived from a plant source and that chemically synthesized. Moreover, the molecular weight range of the polymer, and the degree of purity of the preparation are important factors influencing the biological activity of the polymeric myrcene. These findings are highly unexpected in light of prior art which teaches that the polymeric fraction obtained from mastic, has no therapeutic benefit, and in fact hinders certain biological activities attributed to crude mastic preparations and mastic extracts.

It is herein disclosed for the first time that owing to its various activities in stimulating and inducing cell regeneration, the isolated fraction of mastic gum as described herein may be employed as an active ingredient in a pharmaceutical composition for a number of therapeutic indications.

Advantageously, the compositions of the invention may be used in methods of treating impaired neurological function and skin and scalp conditions. Upon contact with cells of both human and non-human subjects, the composition induces cell differentiation in a wide array of tissues, cell compartments and cell lineages, including skin, endothelium, mucous membranes, bones, tendons and cartilage. In addition, the cell differentiation activity of the pharmaceutical composition may be exploited for promoting in vivo incorporation of medical devices, implants and organ transplants.

Definitions

As used herein, the terms "mastic", "mastic resin", "gum mastic" and "mastic gum", are used interchangeably to refer to a tree resin (also known as an oleoresin) obtained as an exudate from any tree classified in the family Anacardiaceae. Trees in the genus *Pistacia*, most notably *Pistacia lentiscus* L., and in particular the cultivar *P. lentiscus* L. cv. Chia (cultivated on the Greek island of Chios), are known for their high yield of mastic. Other varieties include *P. lentiscus* L. var. *emarginata* Engl., and *P. lentiscus* L. var. *latifolia*

Coss. Additional species of *Pistacia* include for example, *P. atlantica, P. palestina, P. saportae, P. terebinthus, P. vera* and *P. integerrima*.

As used herein, the term "polymer" refers to a compound or a mixture of compounds, comprising repeating subunits (also referred to as monomers) of the same chemical structure, wherein the monomers are in covalent connection. An example of a monomer from which a polymer may be formed is a terpene, for example a monoterpene such as myrcene. Polymers may have various degrees of polymerization and thus encompass polymeric forms of various chain length. Polymers include homopolymers and heteropolymers (also known as copolymers), and may have various isomeric and diastereoisomeric configurations.

As used herein, the terms "polymeric myrcene" and "polymyrcene" interchangeably refer to a polymer formed from myrcene monomers. Polymeric myrcene encompasses polymeric forms having various degrees of polymerization and preferably myrcene polymers having a degree of polymerization of at least 6. The invention encompasses without limitation, polymeric β-myrcene (poly-β-myrcene), polymeric α-myrcene (poly-α-myrcene), homopolymers thereof, heteropolymers (also known as copolymers) comprising myrcene monomers in direct or indirect covalent connection with heterologous monomers, trans- and cis-isomers thereof, D- and L-enantiomers thereof, or combinations thereof. Polymeric myrcene may be obtained in isolated form from a plant source, in particular from mastic, or may be the product of a chemical synthesis reaction.

As used herein, the term "an isolated fraction of mastic gum" refers to a fraction obtained following extraction of gum mastic in at least one polar or non-polar organic solvent, or combinations thereof. The isolated fraction of the invention is generally soluble in either or both of polar and non-polar organic solvents.

As used herein, the term "an isolated fraction of polymeric myrcene" refers to a preparation of polymeric myrcene having a defined molecular weight or molecular weight range, which is separated away from other chemical components present in the source from which the polymeric myrcene was isolated, in particular a chemical reaction mixture or a plant extract.

As used herein, the term "degree of purity" refers to the content of a specified chemical compound in a preparation, expressed as a percentage on a weight per weight basis of the specified chemical compound relative to other chemical compounds in the preparation.

As used herein, "homopolymer" refers to a polymer that is produced from a single type of monomer. For example, polymeric myrcene is a homopolymer when it is produced only from myrcene monomers, for example β-myrcene. A homopolymer may also be a mixture of polymers produced from the same monomer, but having a varying degree of polymerization i.e. chain length. Accordingly, polymeric myrcene may encompass a range of compounds of different chain lengths and accordingly different molecular weights. Further, a homopolymer may contain monomers having different isomeric configurations, for example, β-myrcene and α-myrcene.

As used herein, "heteropolymer" and "copolymer" refer to a polymer produced from more than one type of monomer. Thus for example, a myrcene copolymer is produced from myrcene monomers, in addition to a heterologous type of monomer that is not myrcene. Copolymers include alternating copolymers, periodic copolymers, random copolymers, block copolymers and statistical copolymers, as is known in the art.

As used herein, "degree of polymerization" refers to the number of monomers or monomeric units which are covalently associated together to form a polymer, for example, the number of myrcene monomers in a polymeric myrcene compound.

As used herein, "weight average molecular weight" refers to the average molecular weight of a polymer having molecules of different chain lengths, as expressed by the equation:

$$\overline{M}_w = \frac{\sum_i N_i M_i^2}{\sum_i N_i M_i}$$

where $N_i$ is the number of molecules of molecular weight $M_i$. The weight average molecular weight can be determined for example, by light scattering, small angle neutron scattering, X-ray scattering, and sedimentation velocity.

As used herein, "number average molecular weight" refers to the average molecular weight of a polymer having molecules of different chain lengths, as expressed by the equation:

$$\overline{M}_n = \frac{\sum_i N_i M_i}{\sum_i N_i}$$

where $N_i$ is the number of molecules of molecular weight $M_i$. The number average molecular weight can be determined for example, by gel permeation chromatography (also known as size exclusion chromatography) or viscometry.

The terms "polydispersity index" and "molecular distribution" are herein used interchangeably to refer to the ratio of the weight average molecular weight to the number average molecular weight.

As used herein, "terpene compounds" refers to isoprene-containing hydrocarbons and related oxygen-containing compounds such as alcohols, aldehydes or ketones (terpenoids). The isoprene unit ($CH_2=C(CH_3)-CH=CH_2$) is the basic building block of such compounds. Terpene hydrocarbons in general, have the molecular formula $(C_5H_8)_n$, and include monoterpenes, sesquiterpenes, diterpenes, triterpenes, and tetraterpenes which respectively have 2, 3, 4, 6 and 8 isoprene units. Terpenes may be further classified as acyclic or cyclic.

Examples of monoterpenes include myrcene, limonene and pinene, which are respectively examples of acyclic, monocyclic and bicyclic monoterpenes. Examples of sesquiterpenes include nerolidol and farnesol. Examples of diterpenes include cafestol and phytol. Examples of a triterpene and a tetraterpene are squalene and carotene, respectively.

As used herein, "substantially devoid" means that a preparation or pharmaceutical composition according to the invention that generally contains less than 3% of the stated substance, preferable less than 1% and most preferably less than 0.5%.

As used herein, "therapeutically effective amount" refers to that amount of a pharmaceutical ingredient which substantially induces, promotes or results in a desired therapeutic effect.

As used herein, "pharmaceutically acceptable carrier" refers to a diluent or vehicle which is used to enhance the delivery and/or pharmacokinetic properties of a pharmaceutical ingredient with which it is formulated, but has no therapeutic effect of its own, nor does it induce or cause any undesirable or untoward effect or adverse reaction in the subject.

As used herein, "pharmaceutically acceptable hydrophobic carrier" refers to a hydrophobic non-polar diluent or vehicle in which the polymeric myrcene is dissolved or suspended.

As used herein, "cell differentiation" refers to the process in which a less specialized cell becomes a more specialized cell. Cell differentiation may be established on the basis of changes in any of a number of cellular characteristics, including but not limited to size, shape, organelle appearance, membrane potential, metabolic activity, and responsiveness to signals. A particular "grade" may be given to a cell type to describe the extent of differentiation.

As used herein, "impaired neurological function" refers to a decline or decrease in at least one of sensory, cognitive or motor function, as compared to a previous level of function or activity, and/or as compared to non-impaired individuals matched according to accepted criteria.

Numerical values stated herein are to be understood as the stated value +/−10%.

Isolated Fractions of Mastic Gum and Polymeric Myrcene

The present invention employs isolated fractions comprising polymeric myrcene. The fraction may be from a plant source, in particular mastic gum, or it may be the product of a chemical synthesis. Polymeric myrcene for use in the invention is a polymer compound, or a mixture of polymers of different molecular weights, which are formed from myrcene subunits. Suitable plant sources of polymeric myrcene includes those classified either in the family Anacardiaceae or a different plant family Plant species useful for obtaining the compositions of the invention include without limitation, those of the genera *Pistacia, Pinus, Picea, Juniperus, Alsies, Larix, Ocimum, Laurus* and *Lavendula*. Useful species of *Pistacia* include without limitation, *P. lentiscus, P. atlantica, P. palestina, P. saportae, P. terebinthus, P. vera* and *P. integerrima*. The polymeric myrcene may be obtained from any plant part, including for example, resin, leaves, branches, berries and seeds.

An isolated fraction of polymeric myrcene may be most conveniently obtained from mastic gum, although other plant parts and products may be used. Various methods for obtaining and characterizing an isolated fraction comprising polymeric myrcene from mastic gum are exemplified in Examples 1 and 2 herein. Commercial preparations of mastic are available for example, from the Chios Gum Mastic Growers Association, or from G. Baldwin & Co., U.K.

Alternately, polymeric myrcene may be chemically produced as a synthetic equivalent of a naturally occurring polymer, such as cis-1,4-poly-β-myrcene, or it may be a myrcene polymer not known to occur in nature, such as polymeric α-myrcene. The invention is not limited to the process by which the polymeric myrcene is produced or whether it is natural, synthetic or semi-synthetic.

It is envisioned that the polymeric myrcene may be a synthetic product, produced by a chemical process using as a substrate a monomeric form of the monoterpene myrcene. The monomeric myrcene substrate may be isolated from a plant, or may be chemically or enzymatically converted from a precursor terpene, as is known in the art. For example, monomeric β-myrcene isolated from a plant source may be subsequently polymerized to polymeric β-myrcene by a chemical process. When the myrcene substrate is derived from a natural source, the resultant product may be referred to as a semi-synthetic product. Chemical processes for polymerizing β-myrcene are disclosed for example in U.S. Pat. Nos. 4,564,718; 5,759,569; 7,232,872 and 7,214,750, and in Newmark et al (1988) J. Polymer Sci. 26, 71-77 (1988) and in Cawse et al (1986) Journal of Applied Polymer Science, Vol. 31, 1963-1975.

A suitable chemical synthetic process employs an anionic polymerization reaction, for example that which comprises use of at least one alkane or cycloalkane solvent and at least one alkyl alkali metal. For example, the alkyl alkali metal may be butyl lithium, and the alkane solvent may be hexane, or the cycloalkane solvent may be cyclohexane. The alkane solvent and the alkyl alkali metal initiator may be present in the reaction mixture at a ratio of at least 20:1. The anionic polymerization reaction may be terminated by a compound such as water, an alcohol, molecular oxygen and carbon dioxide.

The synthetic process for 1,4-poly-β-myrcene disclosed herein (Example 3) is particularly suitable for maintaining the various biological activities of the polymer, such as promoting cell differentiation. Monomeric β-myrcene is known to occur in a variety of plants, including trees in the genera *Pinus, Picea, Juniperus, Alsies* and *Larix*, and flowers in the genera *Antirrhinum, Boswellia, Citrus* and *Gynura*.

An isolated fraction of polymeric myrcene may be obtained as the purified product of a chemical synthesis reaction, as exemplified in Example 3 herein. Chemically synthesized polymeric myrcene may be isolated from unreacted substrate and other reagents, analyzed and further fractionated according to molecular weight using analytical and separation methods as are known in the art. Such methods include those which separate molecules on the basis of size, charge or hydrophobicity, including for example, size exclusion chromatography (SEC), high pressure liquid chromatography (HPLC), gas liquid chromatography (GLC) and combinations thereof.

Analytical methods for determining the precise chemical structure of the obtained polymer include nuclear magnetic resonance (for example $^1$HNMR and $^{13}$CNMR), viscometry, various mass spectrometry methods (for example MALDI-TOF), combination methods such as Liquid Chromatography-Mass spectrometry (LC-MS)), light-scattering techniques such as for example Multi Angle Laser Light Scattering (MALLS), total carbon analysis, UV-VIS spectrophotometry, IR and FT-IR spectrophotometry and other methods as are known in the art. The same methods and approaches may be used for purifying and characterizing polymeric myrcene from plants, as shown herein in Example 2.

In a particularly preferred embodiment, a fraction of polymeric myrcene which is a product of a chemical synthesis should be substantially devoid of myrcene monomers and myrcene oligomeric forms having a degree of polymerization less than about 5. It is also preferred that the isolated product be substantially devoid of monomeric terpene compounds which are soluble in polar organic solvents.

Similar methods may be used for obtaining isolated fractions of mastic gum and isolated fractions of polymeric myrcene, when the polymeric myrcene is to be derived from a plant source, such as mastic gum. By way of a general description, collected plant material, for example mastic gum, is combined in a suitable vessel with a suitable solvent, usually a polar solvent. Suitable polar solvents include for example, alcohols, ethers, esters, amides, aldehydes, ketones, nitriles and combinations thereof. Particular examples of polar organic solvents are methanol, ethanol, propanol, isopropanol, 1-butanol, 2-butanol, sec-butanol, t-butanol, 1-pentanol, 2-pentanol, 3-pentanol, neopentanol, 3-methyl-1-butanol, 2-methyl-1-butanol, 3-methyl-2-butanol, 2-methyl-2-butanol, ethyleneglycol, ethyleneglycol monomethyl ether, diethyl ether, methylethyl ether, ethylpropyl ether, methylpropyl ether, 1,2-dimethoxyethane, tetrahydrofuran, dihydrofuran, furan, pyran, dihydropyran, tetrahydropyran, methyl acetate, ethyl acetate, propyl acetate, acetaldehyde, methylformate, ethylformate, ethyl propionate, methyl propionate, dichloromethane, chloroform, dimethylformamide, acetamide, dimethylacetamide, N-methylpyrrolidone, acetone, ethylmethyl ketone, diethyl ketone, acetonitrile, propionitrile, and combinations thereof.

The mastic gum and the solvent are preferably combined such that the solvent is in large excess, for example 10:1 or 20:1. The mixture may be periodically or continuously agitated over a period ranging from a few minutes to a number of hours. The solvent may be decanted without any treatment, or optionally the mixture may be first subjected to low speed centrifugation, for example at 100 to 2000 rpm, as is known in the art. The insoluble material is recovered from the extract and a fresh aliquot of solvent is added to the insoluble material, such that the extraction and dissolution process is repeated for a number of cycles, in order to obtain as much as possible of the polar solvent soluble compounds. After the final dissolution step, the extracts containing polar solvent soluble material are combined and the polar solvent is evaporated (for example by using a rotary evaporation as is known in the art), so as to yield polar solvent soluble material, which may be referred to as a crude, or "first step" extract.

The first step extract material is combined with a non-polar organic solvent and extracted by shaking over a period of 1 hour. Suitable non-polar solvents include acyclic or cyclic, saturated or unsaturated aliphatic hydrocarbons and aromatic hydrocarbons, for example, C5-C10 alkanes, C5-C10 cycloalkanes, C6-C14 aromatic hydrocarbons, and combinations thereof. Each of the foregoing may be optionally substituted by one or more halogens, for example, C7-C14 perfluoroalkanes. Particular examples of non-polar organic solvents are pentanes, hexanes, heptanes, octanes, nonanes, decanes, cyclopentane, cyclohexane, cycloheptane, benzene, toluene, xylene, and isomers and mixtures thereof. Material remaining insoluble or precipitating in the presence of the non-polar solvent is removed and discarded. The non-polar solvent-soluble fraction is then obtained by evaporating the non-polar solvent (for example by rotary evaporation). This fraction may be referred to as purified or "two step" extract, corresponding to an isolated fraction of mastic gum which is characterized by the fact that it is soluble in both a polar solvent and a non-polar solvent, while materials which are soluble in the polar solvent but insoluble in the non-polar solvent, have been removed. This feature distinguishes the isolated fractions of the invention over prior art extracts of mastic gum, the latter of which generally include a wide variety of compounds which are soluble only in polar solvents. According to the teachings of the present invention, such compounds interfere with the beneficial biological activities of the isolated fractions disclosed herein.

The two step extract may be dried further, for example by high vacuum treatment (for example <0.01 mbar for up to several days) to remove residual solvent and other volatile material, weighed and combined with a suitable non-polar organic solvent or other carrier to effect its dissolution. As disclosed herein in Examples 1 and 2, such isolated fractions contain polymeric myrcene. The obtained fractions containing polymeric myrcene may be used directly, or further purified, characterized and/or fractionated using means known in the art, as enumerated above.

In particular embodiments, the isolated fractions of the invention may be obtained by a process comprising the steps of:

(a) treating mastic gum with a polar organic solvent;
(b) isolating a fraction soluble in said polar organic solvent;
(c) optionally removing said polar organic solvent;
(d) treating the soluble fraction obtained in step (b) or (c) with a non-polar organic solvent, (e) isolating a fraction soluble in said nonpolar organic solvent; and
(f) optionally removing said nonpolar organic solvent;

wherein steps (d) to (f) may precede steps (a) to (c).

The process may further comprise size fractionating the soluble fraction obtained following step (c) or step (f), for example by size exclusion chromatography, or any other method known in the art.

The process may further comprise removing the solvent after either or both of steps (c) or (f). Solvent removal may be carried out by any means known in the art, for example rotary evaporation, application of high vacuum and a combination thereof. In particular embodiments, steps (a) to (c) are carried out prior to steps (d) to (f) or vice versa. In a particular embodiment, the polar organic solvent comprises ethanol and the non-polar organic solvent comprises hexane. As is readily understood by one of skill in the art, steps (a) to (c) and steps (d) to (f) may each be independently carried out for a number of cycles to optimize the extraction process and degree of purification of the product.

For preparation of a composition for therapeutic use, suitable carriers may be used, such as hydrophobic carriers including pharmaceutically acceptable oils, optionally in combination with waxes, as described herein.

In particularly preferred embodiments, the compositions comprising the fractions isolated from mastic gum as herein described, should comprise less than about 20% (w/w) of monomeric and oligomeric terpene compounds which are soluble in the polar organic solvent and are substantially insoluble in the non-polar organic solvent, wherein the aforementioned solvents refer to those used in the preparation of the fraction. More preferably, the isolated fractions comprise less than about 5% (w/w) of such terpene compounds. Even more preferably, the isolated fractions are substantially devoid of such terpene compounds. The inhibitory effects of fractions comprising such low molecular weight compounds on the biological activity of polymeric myrcene are exemplified herein in Example 8.

In another particular embodiment, an isolated fraction comprising polymeric myrcene is derived from a plant and is substantially devoid of myrcene monomers and myrcene oligomeric forms having a degree of polymerization less than 6. In another particular embodiment, an isolated fraction comprising polymeric myrcene is derived from a plant and is substantially devoid of terpene compounds which are soluble in a polar organic solvent but are substantially insoluble in a non-polar organic solvent.

It is to be understood that the polymeric myrcene may not have a single molecular weight, but rather, a distribution of molecular weights, representing a population of polymeric myrcene molecules of different chain length i.e. degree of polymerization.

There is no particular upper limit on the molecular weight or degree of polymerization of the polymeric myrcene. In one currently preferred embodiment of the invention, the degree of polymerization is at least about 6. In a particular embodiment, the degree of polymerization is at least about 10. In a particular embodiment, the degree of polymerization is at least about 25. In a particular embodiment, the degree of polymerization is at least about 35. In a particular embodiment, the polymeric myrcene has a degree of polymerization in the range of at least about 6 to about 1800. Suitable exemplary ranges include about 30 to about 500, or about 35 to about 150. The number average molecular weight of the polymeric myrcene is preferably at least about 800. More preferably, the number average molecular weight is at least about 1,000, such as at least 2000 or at least 3000, and even more preferably, the number average molecular weight is at least about 5000. In a particular embodiment, the polymeric myrcene has a number average molecular weight in the range from about 5000 to about 20,000. In a particular embodiment, the polymeric myrcene has a number average molecular weight in the range from at least about 800 to about 100,000. In particular embodiments, the number average molecular weight is in a range selected from the group consisting of: at least about 800 to about 5000; at least about 800 to about 15,000; about 5000 to about 15,000; about 5000 to about 20,000; about 15,000 to about 30,000; about 25,000 to about 40,000; about 35,000 to about 50,000; about 45,000 to about 60,000; about 55,000 to about 70,000; about 65,000 to about 80,000; about 75,000 to about 90,000; about 85,000 to about 100,000; and combinations thereof. In a particular embodiment, the number average molecular weight is at least about 5000. It is to be understood that the composition may comprise different molecular weight fractions of polymeric myrcene, for example in the range from at least about 5000 to about 20,000, as well as in the range from about 25,000 to about 40,000. In a particular embodiment, the polymeric myrcene has a molecular distribution of less than 5.

In a particular embodiment, the isolated fraction consists essentially of polymeric myrcene that has a number average molecular weight in the range from about 5000 to about 20,000.

The molecular weight of the polymeric product may be expressed in a number of ways, for example, weight average molecular weight or number average molecular weight, as is known in the art. Molecular weight may be determined by any of a number of means, such as light scattering, multi angle laser light scattering (MALLS), small angle neutron scattering, X-ray scattering, sedimentation velocity, viscometry (Mark-Houwink equation), mass spectrometry (e.g. MALDI-TOF) and gel permeation chromatography.

The polymeric myrcene may exist as different geometric isomers, resulting from the arrangement of substituents around the carbon-carbon double bond. Such isomers are designated as the cis- or trans-configuration (also referred to respectively as the Z or E configuration), wherein cis-(or Z) represents substituents on the same side of the carbon-carbon double bond, and trans- (or E) represents substituents on opposite sides of the carbon-carbon double bond. The various geometric isomers and mixtures thereof are included within the scope of the invention.

The polymeric myrcene product may contain one or more asymmetric carbon atoms and may therefore exhibit optical isomerism and/or diastereoisomerism. All stereoisomers and diastereoisomers are included within the scope of the invention, either as a single isomer or as a mixture of sterochemical isomeric forms. The various stereoisomers and diastereoisomers may be separated using conventional techniques, for example chromatography or fractional crystallisation. Alternatively desired optical isomers may be made by reaction of the appropriate optically active starting materials under conditions which will not cause racemisation or epimerisation, or by derivatisation, for example with a homochiral acid followed by separation of the diastereomeric derivatives by conventional means.

Suitable forms of polymeric myrcene include polymeric β-myrcene (poly-β-myrcene), including 1,4-poly-β-myrcene, 3,4-poly-β-myrcene, 1,2-poly-β-myrcene, cis-1,4-poly-β-myrcene, trans-1,4-poly-β-myrcene, polymeric α-myrcene (poly-α-myrcene) or combinations thereof. The isolation and characterization of 1,4-poly-β-myrcene from mastic is disclosed for example in Van der Berg et al (1998) Tetrahedron Lett 3:2645-2648.

In particular embodiments, the polymeric myrcene has a linear conformation, a branched conformation or a cyclic conformation.

The isolated fraction of polymeric myrcene according to the invention has a degree of purity of at least 90%, such as at least 93%, or at least 95%, or at least 97%, or at least 98% or at least 99%. As is understood in the art, as high a degree of purity as possible is desirable inter alia to ensure compliance with health regulatory agency requirements. It is to be understood however, that the fraction of polymeric myrcene may contain myrcene polymeric species having various molecular weights, such as within a defined narrow or wide range, without reducing the specified degree of purity. In addition, the isolated fraction of polymeric myrcene may contain different structural isomers as described above of polymeric myrcene without reducing the specified degree of purity. In a particular embodiment, the isolated fraction of polymeric myrcene comprises at least 90% (w/w) of cis-1,4-poly-β-myrcene. In a particular embodiment, the isolated fraction of polymeric myrcene comprises a mixture of cis-1,4-poly-β-myrcene and trans-1,4-poly-β-myrcene, wherein the mixture comprises at least 80% (w/w) of cis-1,4-poly-β-myrcene. In a particular embodiment, the isolated fraction of polymeric myrcene comprises at least 90% (w/w) of cis-1,4-poly-β-myrcene having a number average molecular weight of at least 800. The number average molecular weight may be at least 1,000. The average molecular weight may be at least 2000. The number average molecular weight may be at least 3,000. The number average molecular weight may be at least 5000. The number average molecular weight may be at least 10,000. In a particular embodiment, the isolated fraction of polymeric myrcene comprises at least 90% (w/w) of cis-1,4-poly-β-myrcene having a number average molecular weight in the range from about 800 to about 5000. In a particular embodiment, the isolated fraction of polymeric myrcene comprises at least 90% (w/w) of cis-1,4-poly-β-myrcene having a number average molecular weight in the range from about 1,000 to about 10,000. In a particular embodiment, the isolated fraction of polymeric myrcene comprises at least 90% (w/w) of cis-1,4-poly-β-myrcene having a number average molecular weight in the range from about 10,000 to about 20,000. In a particular embodiment, the isolated fraction of polymeric myrcene comprises at least 90% (w/w) of cis-1,4-poly-β-myrcene having a number average molecular weight in the range from about 5000 to about 20,000. In a particular embodiment, the isolated fraction of polymeric myrcene consists essentially of cis-1,4-poly-β-myrcene that has a number average molecular weight in the range from about 5000 to about 20,000.

In a particular embodiment, the isolated fraction of polymeric myrcene has a degree of purity of at least 90%, and the polymeric myrcene has a degree of polymerization of at least 10.

In a particular embodiment, the isolated fraction of polymeric myrcene comprises at least 90% (w/w) of cis-1,4-poly-β-myrcene having a number average molecular weight in the range from about 20,000 to about 30,000. In a particular embodiment, the isolated fraction of polymeric myrcene comprises at least 90% (w/w) of cis-1,4-poly-β-myrcene having a number average molecular weight in the range from about 30,000 to about 50,000. In a particular embodiment, the isolated fraction of polymeric myrcene comprises at least 90% (w/w) of cis-1,4-poly-β-myrcene having a number average molecular weight in the range from about 50,000 to about 80,000.

In particularly preferred embodiments, the isolated fraction of polymeric myrcene is substantially purified of terpene compounds which are soluble in a polar organic solvent but substantially insoluble in a non-polar organic solvent. In particular, the composition should comprise less than about 10% (w/w), and more preferably, less than about 5% (w/w), and most preferably, less than about 3% (w/w), of terpene compounds which are soluble in a polar organic solvent but substantially insoluble in a non-polar organic solvent. In particular embodiments, the composition is substantially devoid of terpene compounds which are soluble in a polar organic solvent but insoluble in a non-polar organic solvent. In particular embodiments, the composition comprises less than about 10% (w/w), and more preferably less than about 5% (w/w), and most preferably, less than about 3% (w/w), of monomeric terpene compounds. In a particular embodiment, the composition is substantially devoid of myrcene monomers and myrcene oligomeric forms having a degree of polymerization less than about 5. In a particular embodiment, the composition comprises less than about 10% (w/w), and more preferably, less than about 5% (w/w), and most preferably, less than about 3% (w/w), of a terpene compound selected from the group consisting of: β-myrcene, α-myrcene, cis-α-ocimene, dihydromyrcene, limonene, α-pinene, β-pinene, and combinations thereof.

Pharmaceutical Compositions

The composition for use in the invention comprises a therapeutically effective amount of an isolated fraction of polymeric myrcene, and a pharmaceutically acceptable hydrophobic carrier.

A suitable hydrophobic carrier comprises at least one oil, such as for example a mineral oil, a vegetable oil or combinations thereof.

The term "mineral oil" refers to a clear colorless nearly odorless and tasteless liquid obtained from the distillation of petroleum. It may also be referred to as white oil, white mineral oil, liquid petrolatum, liquid paraffin or white paraffin oil. In accordance with a particular embodiment of the invention, the mineral oil is light mineral oil, a commercially available product which may be obtained either as a NF (National Formulary) grade product or as a USP (US Pharmacopoeia) grade product. For use in the invention, the mineral oil is preferably free of aromatics and unsaturated compounds.

Suitable vegetable oils include, but are not limited to almond oil, canola oil, coconut oil, corn oil, cottonseed oil, grape seed oil, olive oil peanut oil, saffron oil, sesame oil, soybean oil, or combinations thereof. In a particular embodiment, the mineral oil is light mineral oil.

The pharmaceutically acceptable carrier may alternately or in addition comprise a suitable oil replacement. Oil replacements include alkanes having at least 10 carbon (e.g., isohexadecane), benzoate esters, aliphatic esters, noncomodogenic esters, volatile silicone compounds (e.g., cyclomethicone), and volatile silicone substitutes. Examples of benzoate esters include $C_{12}C_{15}$ alkyl benzoate, isostearyl benzoate, 2-ethyl hexyl benzoate, dipropylene glycol benzoate, octyldodecyl benzoate, stearyl benzoate, and behenyl benzoate. Examples of aliphatic esters include $C_{12}C_{15}$ alkyl octonoate and dioctyl maleate. Examples of noncomodogenic esters include isononyl isononanoate, isodecyl isononanoate, diisostearyl dimer dilinoleate, arachidyl propionate, and isotridecyl isononanoate. Examples of volatile silicone substitutes include isohexyl decanoate, octyl isononanoate, isononyl octanoate, and diethylene glycol dioctanoate.

Cyclomethicone is an evaporative silicone which may be included in the carrier to assist in making the composition amenable to ejection from a spray dispenser. Furthermore, due to its evaporative property, cyclomethicone may assist in retaining and fixing the formulation on the surface to which it is sprayed e.g. a wound site.

The hydrophobic carrier may further comprise at least one wax. Waxes include for example, beeswax; vegetable waxes, sugar cane waxes, mineral waxes, and synthetic waxes. Vegetable waxes include for example, carnauba, candelilla, ouricury and jojoba wax. Mineral waxes include for example, paraffin wax, lignite wax, microcrystalline waxes and ozokerites. Synthetic waxes include for example, polyethylene waxes.

The pharmaceutical composition may be formulated in any of a number of forms such as for example, a capsule (including a softgel capsule), a tablet, a gel, a liposome, a suppository, a suspension, an ointment, a solution, an emulsion or microemulsion, a film, a cement, a powder, a glue, an aerosol, a spray and a gel.

For preparing the pharmaceutical composition, the polymeric myrcene may be suitably formulated as inclusion complexes, nanoemulsions, microemulsions, powders and liposomes. In a particular embodiment, an inclusion complex comprises at least one cyclodextrin. In a particular embodiment, cyclodextrins comprise hydroxypropyl-β-cyclodextrin. In a particular embodiment, nanoemulsions comprise droplets having average particle size of less than 800 nm. In a particular embodiment, the droplets have average particle size of less than 500 nm. In a particular embodiment, the droplets have average particle size of less than 200 nm. In a particular embodiment, powders are spray dried powders. In a particular embodiment, liposomes comprise multilamellar vesicles. In a particular embodiment, a microemulsion comprises a non-ionic surfactant. Non-ionic surfactants include, without limitation, polyoxyl castor oils, polyoxyethylene sorbitan fatty acid esters (polysorbates), a poloxamer, a vitamin E derivative, polyoxyethylene alkyl ethers, polyoxyethylene sterates, saturated polyglycolyzed glycerides or combinations thereof.

Various formulations of polymeric myrcene and preparation thereof are disclosed herein in Examples 17-21. The pharmaceutical compositions of the invention may be administered by any means that achieve their intended purpose. For example, administration may be by oral, parenteral, topical or transdermal routes. Parenteral administration includes intravenous, intramuscular, subcutaneous, intradermal, intraperitoneal, intraarterial, intrauterine, intraurethral, intracardial, intracerebral, intracerebroventricular, intrarenal, intrahepatic, intratendon, intraosseus and intrathecal routes of administration. Topical administration includes application via a route selected from dermal, vaginal, rectal, inhalation, intranasal, ocular, auricular and buccal., The administering may in addition comprise a technique or means such as electroporation, or sonication in order to assist in their delivery, for example transdermally.

Other techniques which may be employed include for example, radio frequency or pressurized spray application.

The dosage administered will be dependent upon the age, health, and weight of the subject, the use of concurrent treatment, if any, frequency of treatment, and the nature of the effect desired. The amount of the polymeric myrcene of the present invention in any unit dosage form comprises a therapeutically effective amount which may vary depending on the recipient subject, route and frequency of administration.

In general, the amount of polymeric myrcene or isolated mastic gum fraction present in the pharmaceutical composition may conveniently be in the range from about 0.01% to about 25%, such as 0.01% to about 12%, on a weight per weight basis, based on the total weight of the composition. For topical use, the percentage of polymeric myrcene or isolated mastic gum fraction in the composition may be in the range from about 0.05% to about 2.5%. For administration by injection, the percentage of polymeric myrcene or isolated mastic gum fraction in the composition may be conveniently in the range from about 0.1% to about 7%. For oral administration, the percentage of polymeric myrcene or isolated mastic gum fraction in the composition may be in the range from about 0.005% to about 7%.

The pharmaceutical compositions of the invention may be manufactured in a manner which is itself known to one skilled in the art, for example, by means of conventional mixing, granulating, dragee-making, softgel encapsulation, dissolving, extracting, or lyophilizing processes. In preferred embodiments, the formulations are non-aqueous and/or do not comprise polar solvents which directly contact the polymeric myrcene active ingredient, so as to avoid loss of biological activity of the active ingredient. Thus, pharmaceutical compositions for oral use may be obtained by combining the active compounds with solid and semi-solid excipients and suitable preservatives, and/or antioxidants. Optionally, the resulting mixture may be ground and processed. The resulting mixture of granules may be used, after adding suitable auxiliaries, if necessary, to obtain tablets, softgels, capsules, or dragee cores.

Suitable excipients are, in particular, fillers such as saccharides, e.g., lactose or sucrose, mannitol or sorbitol; cellulose preparations and/or calcium phosphates, e.g., tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropymethyl-cellulose phthalate, are used. Dye stuffs or pigments may be added to the tablets or dragee coatings, e.g., for identification or in order to characterize combinations of active compound doses.

Other pharmaceutical compositions for oral use include push-fit capsules made of gelatin, as well as soft, sealed capsules made of gelatin and a plasticizer, such as glycerol or sorbitol. The push-fit capsules can contain the active compounds in the form of granules, which may be mixed with fillers, such as lactose; binders, such as starches; and/or lubricants, such as talc or magnesium stearate and, optionally, stabilizers. In soft capsules, the active compounds are preferably dissolved or suspended in suitable liquids, such as fatty oils, or liquid paraffin. In addition, stabilizers may be added.

Other pharmaceutical compositions for oral use include a film designed to adhere to the oral mucosa, as disclosed for example in U.S. Pat. Nos. 4,713,243; 5,948,430; 6,177,096; 6,284,264; 6,592,887, and 6,709,671.

Pharmaceutical compositions in the form of suppositories consist of a combination of the active compound(s) with a suppository base. Suitable suppository bases include for example, natural or synthetic triglycerides, polyethylene glycols, or paraffin hydrocarbons.

Formulations for parenteral administration include suspensions and microparticle dispersions of the active compounds as appropriate. In a particular embodiment, oily injection suspensions may be administered. Suitable lipophilic solvents or vehicles include fatty oils, e.g., sesame oil, or synthetic fatty acid esters, e.g., ethyl oleate, triglycerides, polyethylene glycol-400, cremophor, or cyclodextrins. Injection suspensions may contain substances which increase the viscosity of the suspension include, e.g., sodium carboxymethyl cellulose, sorbitol, and/or dextran. Optionally, the suspension may also contain stabilizers.

Pharmaceutical compositions can also be prepared using liposomes comprising the active ingredient. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. In general, the preferred lipids are phospholipids and the phosphatidyl cholines (lecithins), both natural and synthetic. Methods to form liposomes are known in the art, as disclosed for example, in Prescott, Ed., Methods in Cell Biology, Volume XIV, Academic Press, New York, N.Y. (1976) and in U.S. Pat. No. 7,048,943.

Formulations for topical administration include ointments. Suitable carriers include vegetable or mineral oils, white petrolatum, branched chain fats or oils, animal fats and waxes. The preferred carriers are those in which the active ingredient is soluble. Stabilizers, humectants and antioxidants may also be included, as well as agents imparting color or fragrance, if desired. Ointments may be formulated for example, by mixing a solution of the active ingredient in a vegetable oil such as almond oil with warm soft paraffin, and allowing the mixture to cool.

The pharmaceutical composition may comprise an oil-in-water emulsion or microemulsion in order to facilitate its formulation for oral, parenteral or topical use Such emulsions/microemulsions generally include lipids, surfactants, optionally humectants, and water. Suitable lipids include those generally know to be useful for creating oil-in-water emulsions/microemulsions, for example fatty acid glyceride esters. Suitable surfactants include those generally known to be useful for creating oil-in-water emulsions/microemulsions wherein lipids are used as the oil component in the emulsion. Non-ionic surfactants may be preferred, such as for example, ethoxylated castor oil, phospholipids, and block copolymers of ethylene oxide and propylene oxide.

Suitable humectants, if used, include for example propylene glycol or polyethylene glycol.

The pharmaceutical composition may be formulated in the form of a gel, such as a hydrogel formed from a gel-forming polymer such as carrageenan, xanthan gum, gum karaya, gum acacia, locust bean gum, guar gum. A hydrogel may be combined with an oil-in-water emulsion comprising the active ingredient.

The pharmaceutical composition may be formulated in the form of a cement such as those comprising polymethylmetacrylate (PMMA) or calcium phosphate, as are used in orthopedic surgery.

The pharmaceutical composition may be formulated in the form of a powder, in particular such as those used for transdermal applications using radio frequency, as described for example, in U.S. Pat. Nos. 6,074,688 and 6,319,541 and WO 2006/003659.

The pharmaceutical composition may be formulated in the form of a glue, such as those comprising octocyanoacrylate used for wound closure applications.

In a particular embodiment, the pharmaceutical composition is substantially devoid of monomeric and low molecular weight terpene compounds, including for example, those classified as monoterpenes, diterpenes, sesquiterpenes, triterpenes, tetraterpenes. Examples of terpene compounds include β-myrcene, α-myrcene, cis-α-ocimene, dihydromyrcene, limonene, α-pinene, β-pinene, tirucallol, betulonal, masticadienonic acid, masticadienolic acid, isomasticadienonic acid, isomasticadienolic acid, oleanolic acid, and oleanonic acid.

Therapeutic Uses

The present invention provides therapeutic uses and methods of treating impaired neurological function, treating skin and scalp disorders, inducing tissue repair and wounds in a subject in need thereof. The methods comprise administering to the subject a therapeutically effective amount of a composition comprising an isolated fraction of mastic gum, or an isolated fraction of polymeric myrcene, as described herein.

The step of administering the compositions may comprise any acceptable route including oral, topical, parenteral, and transdermal. Parenteral administration includes intravenous, intramuscular, subcutaneous, intradermal, intraperitoneal, intraarterial, intrauterine, intraurethral, intracardial, intracerebral, intracerebroventricular, intrarenal, intrahepatic, intratendon, intraosseus and intrathecal routes of administration. Topical administration includes application via a route selected from dermal, vaginal, rectal, inhalation, intranasal, ocular, auricular and buccal.

In particular embodiments, the step of administering comprises contacting cells of a particular type, of a particular lineage or at a particular stage of differentiation, with the composition. The cells may be any of a wide variety of cell types, including in particular, neural cells, neuronal cells, endothelial cells, epithelial cells and stem cells of said lineages. Further, the cells may be of any lineage for example, ectodermal, mesodermal, entodermal lineages and stem cells of said lineages. In various embodiments, the step of contacting cells is carried out in vivo, ex vivo or in vitro.

The method disclosed herein for treating impaired neurological function is particularly advantageous for subjects afflicted with neurodegenerative conditions and diseases, including in particular, trauma, vascular dementia, senile dementia, Alzheimer's disease, amyotrophic lateral sclerosis (ALS), multiple sclerosis), stroke and Parkinson's disease. In other cases, the method may be advantageously applied in subjects suffering from impaired neurological function due to an infection (e.g. viral, bacterial, fungal, parasitic) or an immunological disorder. In a particular embodiment, the impaired neurological function is due to exposure to a drug, such as an anesthetic. Impaired neurological function may also be associated with a condition selected from the group consisting of schizophrenia, bipolar disorder, depression, obesity, anorexia and cachexia.

Skin and scalp disorders include all disorders of skin, scalp and hair appendages, including for example, nails and hair follicles. Particular conditions that may benefit from the invention include alopecia, eczema, psoriasis, seborrheic keratosis, seborrhea and skin wounds. Skin wounds include venous leg ulcers, pressure ulcers, diabetic foot ulcers, burns, amputation wounds, decubitus ulcers (bed sore), split-skin donor grafts, skin graft donor sites, medical device implantation sites, bite wounds, frostbite wounds, puncture wounds, shrapnel wounds, dermabrasions, contusions, an infection wounds and surgical wounds. Wounds may be the result of infection; exposure to ionizing radiation; exposure to laser, or exposure to a chemical agent.

The invention may be particularly effective for scar-less repair of wounds.

The invention may be particularly effective and economical for treatment of chronic non-healing wounds. As is known to one of ordinary skill in the art, the efficacy of a particular treatment in promoting wound healing may be assessed by various criteria, including the rate of closure measured by length, width and depth of the wound over time, epithelization rate, formation of granulation tissue and tissue tensile strength.

The methods disclosed herein for inducing or promoting tissue regeneration are particularly advantageous for subjects who have tissue damage, which for example, may be associated with, or the result of an injury or insult. The methods for inducing or promoting tissue regeneration may be used in subjects who have suffered an injury or insult selected from the group consisting of a myocardial infarction, a pulmonary embolism, a cerebral infarction, peripheral artery occlusive disease, a hernia, a splenic infarction, a venous ulcer, an axotomy, a retinal detachment, a wound (for example, a burn wound, bite wound, a frostbite wound, a puncture wound, a shrapnel wound, a contusion, an infection wound or a surgical wound), an infection and a surgical procedure.

The methods of the invention are exemplified in the Examples disclosed herein Example 4 discloses that an isolated fraction of polymeric myrcene (derived from mastic of *Pistacia*) induces differentiation of retinal pigment epithelium cells.

Example 5 discloses that polymeric myrcene shortens the recovery time from anesthesia in experimental animals.

Example 6 discloses that the same fraction has activity in inducing differentiation in melanoma and neuroblastoma tumor cell lines.

Example 7 discloses that chemically synthesized polymeric myrcene of various molecular weight ranges induces differentiation in retinal pigment epithelium cells.

Example 8 discloses that small molecular weight compounds from mastic which are separated from polymeric myrcene during preparation thereof on the basis of their being soluble only in a polar solvent in accordance with the invention, interfere with, reduce and hinder the cell differentiation inducing activity exerted by polymeric myrcene.

Examples 9, 10 and 11 disclose that the invention may be applied to wound healing in mammals and non-mammalian subjects.

Example 12 discloses that compositions comprising polymeric myrcene according to the invention have ameliorating effects in an animal model of vascular dementia.

Example 13 discloses that the invention may be used to stimulate appetite in subjects affected by various disorders that result in appetite loss or pathological weight gain result in obesity.

Example 14 discloses that compositions comprising polymeric myrcene according to the invention have ameliorating effects in an animal model of stroke.

Example 15 discloses that compositions comprising polymeric myrcene according to the invention have ameliorating effects in an animal model of optic nerve injury/trauma.

Example 16 discloses that compositions comprising polymeric myrcene according to the invention have ameliorating effects in an animal model of retinal detachment and provides evidence of scar-less repair of wounds. The step of contacting cells may be carried out in vitro or ex vivo. In particular, cells, or an organ or tissue derived therefrom which is intended for implantation or transplantation into the subject may be treated according to the invention. For example, cell explants or cells or tissues grown and maintained in culture may be contacted with the composition. The cells may originate for example, from stem cells of an autologous or homologous donor, and be intended for organ regeneration and/or implantation into a recipient. In other cases, the cells are from a heterologous donor and are intended for implantation or transplantation into a recipient. In a particular embodiment, the cells are those of an organ or tissue from a heterologous donor intended for implantation or transplantation into a recipient. In a particular embodiment, the cells are those which secrete soluble factors.

The method may be carried out prior to or following implantation of a medical device into the subject. Medical devices include, but are not limited to a prosthetic, an artificial organ or component thereof, a valve, a catheter, a tube, a stent, an artificial membrane, a pacemaker, a sensor, an endoscope, an imaging device, a pump, a wire and an implant. Implants include, but are not limited to a cardiac implant, a cochlear implant, a corneal implant, a cranial implant, a dental implant, a maxillofacial implant, an organ implant, an orthopedic implant, a vascular implant, an intraarticular implant and a breast implant.

In a particular embodiment, the medical device is an organ implant, which may in certain cases comprise autologous cells of the subject.

In a particular embodiment, the step of contacting comprises a means selected from the group consisting of electroporation, sonication, radio frequency, pressurized spray and combinations thereof.

In a particular embodiment, the step of contacting comprises establishing contact between interstitial fluid and the composition. This may be particularly advantageous for wounds which are surrounded by interstitial fluid. Contact between interstitial fluid and the composition may be accomplished by piercing and/or teasing the dermis with a needle, a microneedle, or an apparatus comprising a plurality of needles or microneedles. Such needles or microneedles are preferably non-hollow and may be fashioned in a plurality for example, on a comb or brush-like apparatus.

The method of the invention is suitable for application in humans, non-human mammals, fish and birds.

Articles of Manufacture

The method of the invention may encompass use of an article of manufacture which incorporates the composition comprising polymeric myrcene described herein.

The pharmaceutical composition may be in the form of a coating on the article of manufacture, or may be contained within a vessel which is integral to the article of manufacture. The pharmaceutical composition is advantageously present as a coating on devices which are inserted to the body and are intended for integration therein, for example an implant. The pharmaceutical composition can thus promote tissue closure over the implant due to the activity of polymeric myrcene in inducing cell differentiation.

The pharmaceutical composition may be advantageously incorporated onto or into articles used in wound healing or tissue repair, for example, a dressing or bandage. The pharmaceutical composition can thus promote wound healing due to the activity of polymeric myrcene in inducing cell differentiation.

In other cases, the pharmaceutical composition may be incorporated to a delivery device such as a needle, an injection device or a spray dispenser from which the composition is delivered to a body site requiring therapy, for example a wound site.

Articles of manufacture include, but are not limited to a fabric article, a diaper, a wound dressing, a medical device, a needle, a microneedle, an injection device and a spray dispenser. In a particular embodiment, the article of manufacture comprises a plurality of microneedles. Medical devices and implants are as hereinbefore described.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1 Preparation of Isolated Fractions of Mastic Gum from Plant Sources

Method 1.

Mastic resin (10 g) was combined with absolute ethanol (200 ml) and the mixture was allowed to stand overnight. The mixture was shaken, larger insoluble particles were allowed to settle over 20 minutes, and the ethanol was transferred into a new flask. The remainder was shaken with a fresh portion of absolute ethanol (150 ml) for 10 minutes. This ethanol fraction was combined with the first fraction. The procedure was repeated with another 150 ml portion of absolute ethanol which was combined with first two ethanol fractions. Subsequently, the ethanol was removed in vacuo using a rotary evaporator (water-bath temperature 30° C.). Hexane (300 ml) was added to the remaining residue and the mixture was shaken repeatedly over a period of two hours. After standing overnight in the closed flask in order to complete dissolution of soluble material and precipitation of any insoluble material, the clear hexane solution was transferred into a clean pre-weighed flask and the hexane was removed using a rotary evaporator. To the obtained isolated fraction was added immediately the desired amount of oil and the mixture was shaken until a homogeneous mixture was obtained.

Method 2.

Mastic resin (10 g) was combined with absolute methanol (300 ml) and the mixture was allowed to stand overnight. The mixture was shaken, larger insoluble particles were allowed to settle over 20 minutes, and the methanol soluble fraction was transferred into a new flask. The remaining insoluble material was shaken with a fresh portion of absolute methanol (200 ml) for 10 minutes. This second methanol soluble fraction was combined with the first methanol soluble fraction. The procedure was repeated with another 200 ml portion of absolute methanol, and a third methanol soluble fraction was combined with first two methanol soluble fractions. Subsequently, the methanol was removed in vacuo using a rotary evaporator (water-bath temperature 30° C.). Hexane (300 ml) was added to the remaining residue and the mixture was shaken repeatedly over a period of two hours. After standing overnight in the closed flask in order to complete dissolution of soluble material and precipitation of any insoluble material, the clear hexane solution was transferred into a clean pre-weighed flask and the hexane was removed using a rotary evaporator. To the obtained isolated fraction was added immediately the desired amount of oil and the mixture was shaken in the closed flask until a homogeneous mixture was obtained.

Method 3.

Mastic resin (5 g) was pulverized with pestle and mortar and combined with hexane (200 ml). The mixture was shaken every 30 minutes during an eight hour period and subsequently left to stand overnight. The hexane soluble fraction was removed from insoluble material and transferred to a clean flask. The hexane was removed from the hexane soluble fraction using a rotary evaporator. The remaining residue was then subjected to a high-vacuum system (<0.01 mbar) for at least 24 hours in order to remove additional volatile materials. Absolute ethanol (100 ml) was then added to the remaining residue and the mixture was shaken repeatedly over a period of 1 hour. The ethanol soluble fraction was transferred to clean flask and the extraction was repeated with two additional 100 ml portions of absolute ethanol. The ethanol soluble fractions were combined and any remaining insoluble material was allowed to settle overnight. The clear ethanol solution was transferred into a clean, pre-weighed flask and the ethanol was removed under vacuum. To the remainder was added immediately the desired quantity of oil and the mixture was shaken until a homogeneous formulation was obtained.

Method 4.

Leaves, soft twigs, fruits and berries of *Pistacia lentiscus* L., *P. atlantica* or *P. palestina* trees were collected, cleaned and pulverized. Dissolution with ethanol or methanol was initially carried out essentially as described in Methods 1 and 2, and subsequent dissolutions were carried out using combinations of ethanol or methanol with a vegetable oil for a number of cycles.

Method 5.

Leaves (30 g) of *Pistacia lentiscus* L. were collected, cleaned and cut to small pieces with a knife and placed in a food processor. Olive oil (100 ml) was added and processed. The whole mixture was removed and placed in a glass beaker. Two hundred ml of ethanol (96%) was added and the mixture heated to 65° C. for 20 min. The whole mixture was placed in gauze and the liquid was pressed out. The upper ethanol phase was removed by pipetting and discarded. Residual ethanol may be removed from the oil phase by evaporation.

Method 6.

Berries (25 gram) of *Laurus nobilis* (collected in May or June) were washed with ethanol (96%, 200 ml) for 30 seconds. The ethanol and the berries were removed and olive oil was added to the remaining residue. Any insoluble material was allowed to precipitate, and the clear oil solution was isolated.

Method 7.

For each preparation, approximately ten grams of resin exudate collected from *Pistacia lentiscus* L., *P. atlantica* or *P. palestina* trees in the area of Zikhron Yaakov, Israel was used. The resin was combined with 30 ml methanol in a suitable glass vessel and the mixture was vigorously shaken repeatedly during a time period of 30 minutes to 2 hours—. A portion of the resin dissolved, while insoluble material settled at the bottom of the vessel. The upper liquid was decanted, and additional aliquots of methanol were added as above, and the shaking and decantation process was repeated. The insoluble material remaining was then immersed in distilled water for 30 seconds to 1 minute, resulting in a white milky liquid with insoluble material remaining. After several alternate rapid cycles of treatment with water, and methanol, the remaining insoluble material was air dried and weighed. Typically, about 1-3 grams of insoluble material were obtained from ten grams of starting resin. Similar results were obtained using ethanol as the solvent instead of methanol. Dissolution of the final fraction of insoluble material was carried out immediately after drying by addition of a vegetable oil, typically olive oil or grape seed oil, in an amount sufficient to provide a solution of desired concentration, typically 1% or 10%.

Method 8.

For each preparation, approximately ten grams of either (i) resin exudate collected from the bark of *Pistacia lentiscus* L. or *P. palestina* trees growing in the Carmel Mountain Region, Israel, or (ii) commercially obtained Chios mastic (available for example from the Chios Gum Mastic Growers Association or from G. Baldwin & Co.) was used. The resin was pulverized in a mortar, transferred to a glass beaker and 100 ml of ethanol (98%) was added. After shaking for few minutes, the ethanol was decanted, leaving a reduced mass of resin due to the removal of solubilized material. An additional amount of ethanol was added, and the steps of shaking, decanting and solvent addition were rapidly repeated for a number of cycles, each cycle lasting between 5 to 30 minutes. The insoluble material remaining after the final cycle (typically corresponding to 20 to 35% by weight of the commercial starting material, or 10 to 25% of the collected resin starting material) was solubilized in one of olive oil, peanut oil, grape seed oil, sesame oil, cotton oil or soy oil to give a final concentration of 8 to 10% (w/w).

Method 9.

Pulverized mastic (~10 g) was combined with 100 ml methanol. After shaking for few minutes, the methanol was decanted, leaving a reduced mass of non-soluble white material due to the removal of solubilized material. An additional amount of methanol was added, and the steps of shaking, decanting and solvent addition were rapidly repeated for a number of cycles. The insoluble material remaining after the final cycle (typically corresponding to 20 to 30% by weight of the starting material) was solubilized in olive oil. The dissolution process typically involves olive oil warmed to 45° C. and gentle agitation in the beaker.

Method 10.

Pulverized mastic (~10 g) was combined with 25 ml soy oil and 100 ml methanol in a glass beaker. Stirring using a magnetic stirrer was carried out for 2 hours. The solvent was decanted off and fresh methanol was added, followed by stirring for one hour. The solvent was decanted off, followed by evaporation under vacuum to remove residual solvent.

Method 11.

Pulverized mastic (~10 g) was combined with 100 ml ethanol (96%) in a glass beaker. Stirring using a magnetic stirrer was carried out for 10 minutes. The solvent was decanted off and an additional amount of ethanol was added, followed by stirring for 5 minutes and decanting off the solvent. The steps of solvent addition, stirring and decanting were repeated for 4 cycles. Then n-hexane (100 ml) was added to the insoluble white material, followed by repeated shaking until the material dissolved. A small sample was desiccated and weighed in order to determine the concentration. The bulk of the hexane solution was applied to a calibrated size exclusion column and the fraction having molecular weight up to 1500 was discarded. The fraction having molecular weight greater than 1500 was mixed with 20 grams of heavy paraffin ointment. The mixture is homogenized by repeated mixing, and the hexane was removed by evaporation under vacuum.

This procedure may also be performed by mixing paraffins and waxes having increasing molecular weight in order to obtain a more solid product.

The term "RPh-1" is used herein to refer to an isolated fraction prepared as in any of the above Methods, and following dissolution in a suitable oil, wax or combination thereof.

RPh-1 was used directly for in vitro cell culture experiments or for treatment of test animals, typically at final concentrations ranging from 0.025 to 5% in a particular oil or mixture of oils, as specified herein. Furthermore, as shown in Example 2, the major component of RPh-1 was determined to be 1,4-poly-β-myrcene of molecular weight in the range from 5000 to 20,000.

Example 2. Chemical Characterization of Polymeric Myrcene Isolated from Plant Sources Overview Mastic resin from *Pistacia lentiscus* L. was extracted according to method 1 or 2 in order to obtain the desired fraction (termed RPh-1) which was analyzed by Size Exclusion Chromatography (SEC) in order to define the molecular weight distribution. The chemical structure of RPh-1 was analyzed by nuclear magnetic resonance (NMR) following preparative SEC fractionation.

It was found that the RPh-1 contains a "light" fraction with molecular weights below 1,000 and a "heavy" polymer fraction with molecular weight in the range 5000 to 20,000. Based on NMR analysis ($^1$H-NMR and $^{13}$C-NMR) the predominant compound in the "heavy" fraction has a structure consistent with that of 1,4-poly-β-myrcene.

Preparative separations were carried out using ethyl acetate and tetrahydrofuran (THF) as eluents. In both cases, the "heavy" polymer fraction was observed to exhibit various beneficial biological activities, including that of inducing cell differentiation, as described in Examples 4 and 6. In contrast, the "light" fraction demonstrated toxicity in in vitro efficacy experiments using pigmented retinal epithelial cells. It was found that in order to preserve the activity of the polymer fraction, it is highly important to protect it from oxidation or cross-linking reactions by diluting it in a hydrophobic solvent, preferably oil, optionally in combination with a wax.

Methods

Mastic resin (10 g) was combined with absolute ethanol (200 ml) and the mixture was allowed to stand overnight. The mixture was shaken, larger insoluble particles were allowed to settle over 20 minutes, and the ethanol was transferred into a new flask. The remainder was shaken with a fresh portion of absolute ethanol (150 ml) for 10 minutes. This ethanol fraction was combined with the first fraction. The procedure was repeated with another 150 ml portion of absolute ethanol which was combined with first two ethanol fraction. Subsequently, the ethanol was removed in vacuo on a rotary evaporator (water bath temperature 30° C.). To the remainder was added hexane (300 ml) and the mixture was shaken repeatedly over a period of two hours. After standing overnight in the closed flask in order to complete precipitation of any insoluble material, the clear hexane solution was transferred into a clean flask and used for analytical and preparative separations.

Macromolecules are separated using Size Exclusion Chromatography (SEC) on the basis of their being excluded from the stationary phase. In SEC the highest molecular weight compounds are totally excluded from the packing pores and therefore elute first. Molecular weights of polymer test compounds may be estimated by SEC on the basis of comparison with a standard curve constructed with compounds of known molecular weight, for example polystyrene standards. However, polymer molecular weights determined on the basis of such comparisons may be subject to an inherent error margin of at least about 10 to 15%, since the relationship between hydrodynamic volume and molecular weight is not the same for all polymers, so only an approximate determination can be made.

For analytical SEC, a PLgel (7.5*300 mm 5μ $10^3$ A°) column was used and calibrated with polystyrene standards of molecular weights 1,000, 2000, 5000, 10,000, 30000 and 70000. Solvents used (hexane, ethyl acetate, tetrahydrofuran (THF), dichloromethane (DCM) and acetone) were all analytical grade for liquid chromatography. For analytical purposes THF was found to be optimal. The chromatography instrument used was a ThermoPhinnigan TSP fitted with either a diode array detector or an ELSD detector, using a flow rate of 1 ml/min, run time of 15 min and 100% THF for the mobile phase.

Preparative SEC was carried out using the following conditions:
1. Conditions for THF:
Column: PLgel: 25*300 mm 5μ $10^3$ A°
Mobile phase: hexane 60%/THF 40% flow rate 11 ml/min
Separation was repeated 12 times with 1 ml extract each and two fractions were collected:
1) Heavy MW content; 2) Low MW content.
2. Conditions for DCM:
Column: PLgel: 25*300 mm 5μ $10^3$ A°.
Mobile phase: hexane 70%/DCM 30% flow rate 11 ml/min.
Separation was repeated 12 times with 1 ml extract each and two fractions were collected:
1) Heavy MW content; 2) Low MW content.
For each preparative SEC run, the column was calibrated with polystyrene standards of molecular weights 1,000, 2000, 5000, 10,000, 30000 and 70000.

The collected fractions from these two different mobile phases were divided into two, one half was evaporated to dryness using an evaporator and 3 ml oil was added. To the second half 3 ml oil was added and then the organic solvent was evaporated. The obtained samples were analyzed for biological activity.

The heavy MW material from the THF elution was analyzed by $^1$H-NMR and $^{13}$C-NMR at 300 MHz and 75 MHZ respectively.

Results

Analytical SEC

Figure 1:
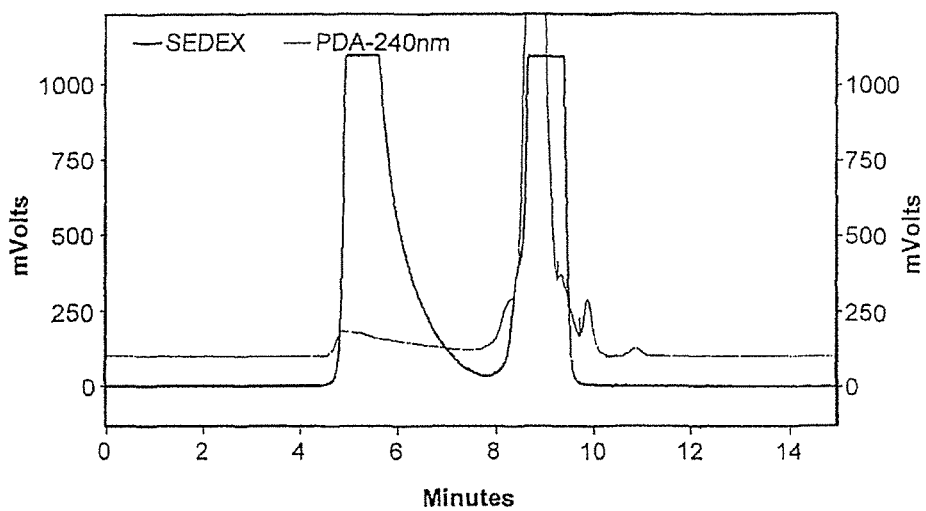
FIG. 1 shows size exclusion chromatography of a mastic resin extract using SEDEX and PDA detectors.

FIG. 1 shows the SEC analytical chromatogram obtained_using a PDA detector (faint line) and an ELSD-SEDEX detector (bold line). A fraction corresponding to molecular weight in the range of about 60,000 to about 5000 (eluting at 5-7 minutes) was detected only with the ELSD detector. Both detectors indicated the presence of a fraction of molecular weight in the range <1,000.

Preparative SEC

Figure 2A:
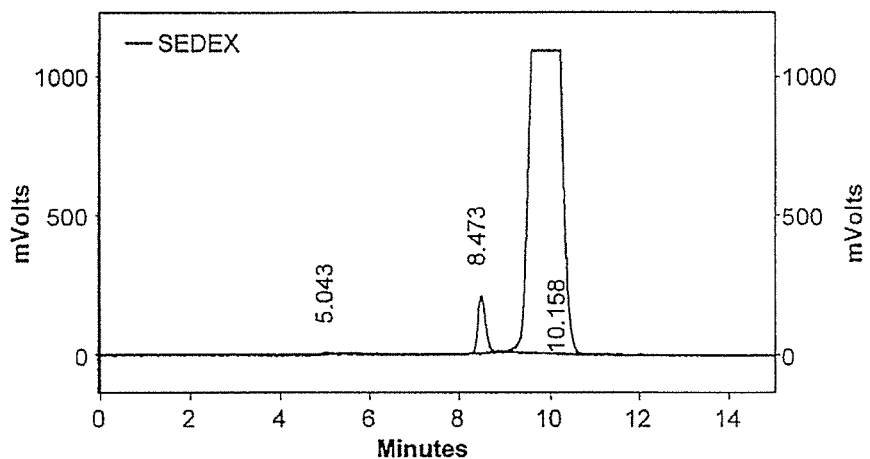
FIGS. 2A-B show low (FIG. 2A) and heavy (FIG. 2B) molecular weight fractions of a mastic resin extract obtained by preparative size exclusion chromatography.
Figure 2B:
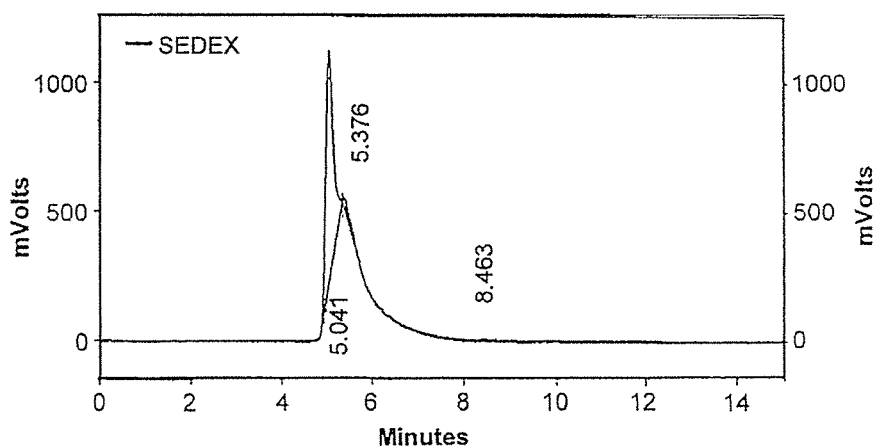

FIGS. 2A-B show the heavy (FIG. 2B) and low molecular weight (FIG. 2A) fractions obtained by preparative SEC. The heavy fraction was obtained by SEC run in DCM/hexane, while the light fraction was obtained by SEC run in THF/hexane. Table 1 summarizes the fractions obtained using preparative SEC and various solvent systems.

TABLE 1

Fractions collected from preparative columns using various eluents and evaporation modes.

| Fraction No. | Molecular weight range | Eluents/evaporation mode |
|---|---|---|
| 19-1 | Heavy | THF/Hexane evaporation with oil |
| 19-2 | Light | |
| 19-3 | Heavy | THF/Hexane evaporation without oil |
| 19-4 | Light | |
| 19-5 | Heavy | DCM/Hexane evaporation with oil |
| 19-6 | Light | |
| 19-7 | Heavy | DCM/Hexane evaporation without oil |
| 19-8 | Light | |

NMR Analysis

Figure 3:
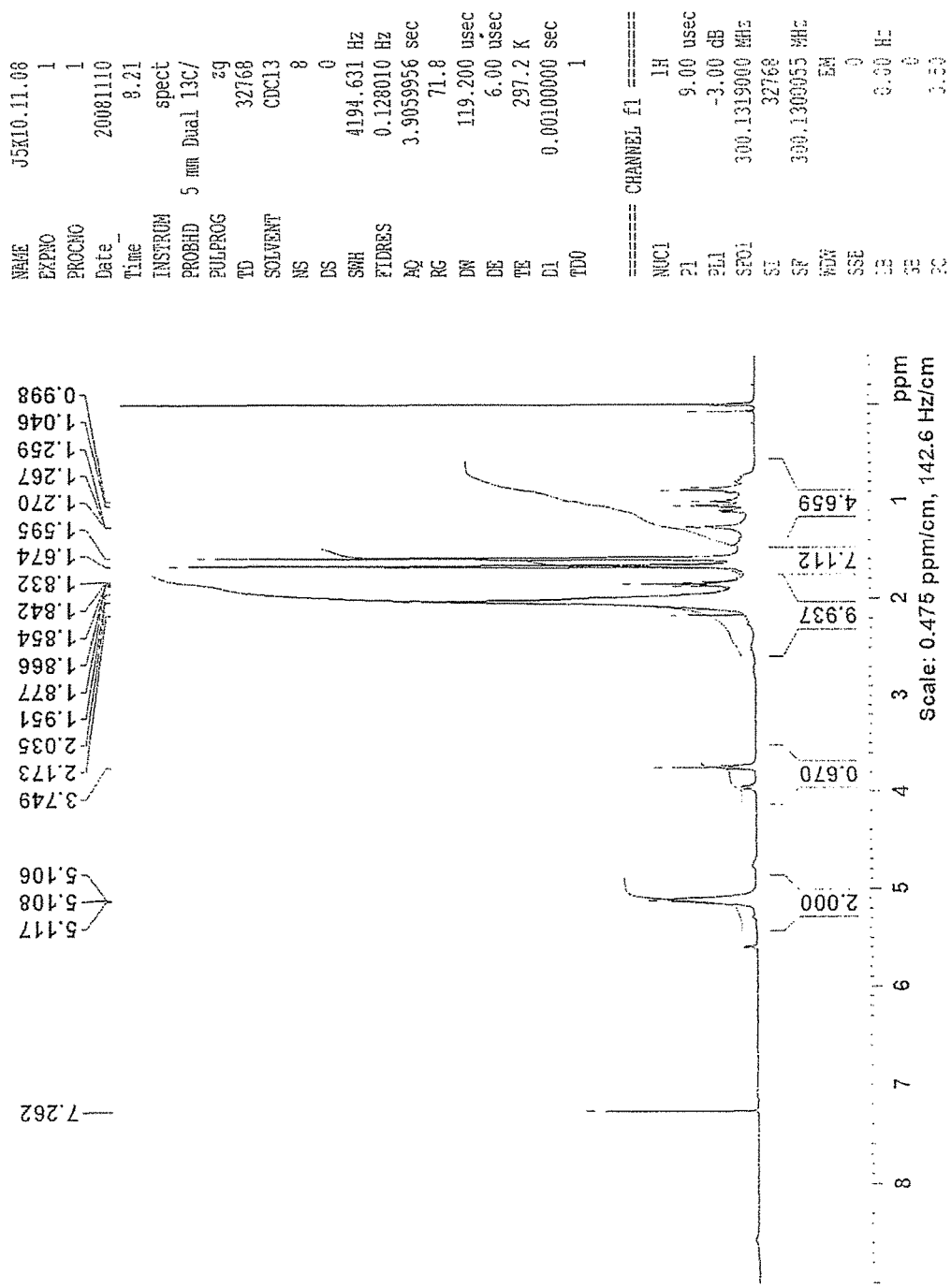
FIG. 3 shows the $^{13}$C-NMR spectrum of the heavy MW fraction obtained by preparative SEC of a mastic resin extract.
Figure 4:
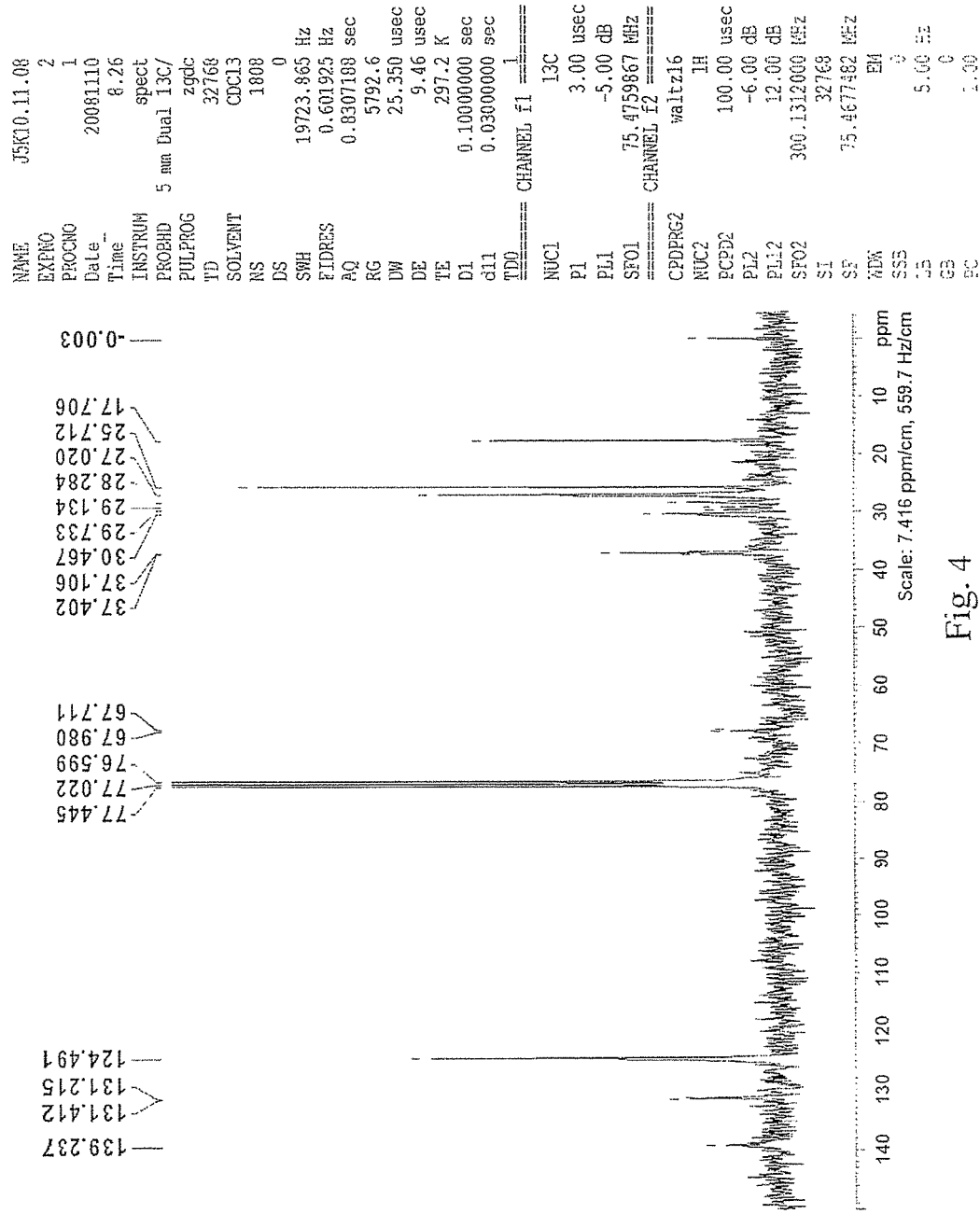
FIG. 4 shows the $^{13}$C-NMR spectrum of the heavy MW fraction obtained by preparative size exclusion chromatography of a mastic resin extract.

FIG. 3 shows the $^1$H-NMR spectrum obtained for the heavy MW material from preparative SEC run in hexane 60%/THF 40%. FIG. 4 shows the $^{13}$C-NMR spectrum obtained for the heavy MW material from preparative SEC run in hexane 50%/THF 50%.

The $^1$H-NMR and $^{13}$C-NMR analyses indicate that 1,4-polymeric β-myrcene is the major component of the heavy MW fraction obtained from preparative SEC of the polar solvent-insoluble material (RPh-1) from mastic.

Example 3. Chemical Synthesis of 1,4-Polymeric β-Myrcene

Synthetic 1,4-polymeric β-myrcene preparations of various molecular weights was prepared, using methods generally based on procedures disclosed in Newmark et al (1988) J. Polym Sci. 26:71-77.

Methods

The following reagents were added to a 250 ml 3-necked flask equipped with a condenser: β-myrcene, hexane and sec-butyl lithium in cyclohexane, all under nitrogen atmosphere, in the quantities shown in Table 2. The volume of hexane used in each reaction was generally at least about 20 to 25 times the volume of the butyl lithium initiator. Each reaction mixture was heated to 80° C. and stirred for about 1 hour. In order to estimate polymer concentration a small aliquot (few ml) of solution was taken and evaporated to dryness.

For some reaction mixtures, lithium was removed following the reaction by diluting the final mixture with an excess of hexane and washing twice with water. The organic phase was separated and dried with sodium sulfate.

For use in biological activity assays and characterization of molecular weight, a 10% solution of the synthesized polymer in olive oil was prepared by adding olive oil to a final concentration of 10% (without hexane) and the hexane solvent evaporated. Apparent molecular weight was determined using SEC and calculation from a calibration curve prepared using polystyrene standards of molecular weight 2000, 5000, 10,000, 30000 and 70000. The conditions used for SEC were as follows:

Column: PLgel: 7.5*300 mm 5µ 10$^3$ A°
Mobile phase: 100% THF
Flow rate 1 ml/min
Detector: ELSD Results The expected and calculated molecular weights of the polymeric β-myrcene produced under different reaction conditions are presented in Table 2.

TABLE 2

Reactant quantities and product molecular weight of chemically synthesized polymeric myrcene.

| Reaction | sec-butyl lithium (ml) | sec-butyl lithium (mol) | β-myrcene (mol) | Expected MW | Calculated MW |
|---|---|---|---|---|---|
| 1 | 3 | 0.00420 | 0.0735 | 2381 | 3816.05 |
| 2 | 2 | 0.00280 | 0.0735 | 3571 | 7007.32 |
| 3 | 1 | 0.00140 | 0.0735 | 7143 | 11400.54 |
| 4 | 0.5 | 0.00070 | 0.0735 | 14286 | 27153.13 |
| 5 | 0.25 | 0.00035 | 0.0735 | 28571 | 46034.97 |
| 6 | 4 | 0.00560 | 0.0735 | 1786 | 2845.24 |

Figure 5A:
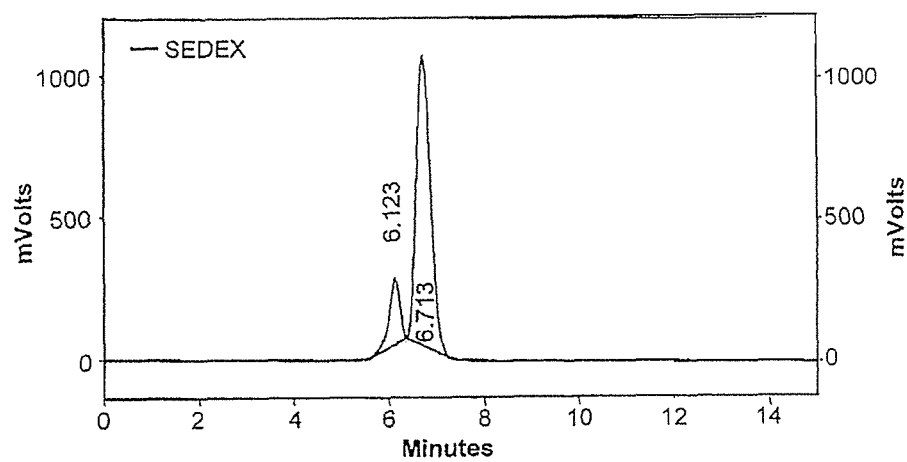
FIGS. 5A-B shows analytical size exclusion chromatography of high (FIG. 5A) and low (FIG. 5B) products obtained in a chemical synthetic process for polymeric myrcene.
Figure 5B:
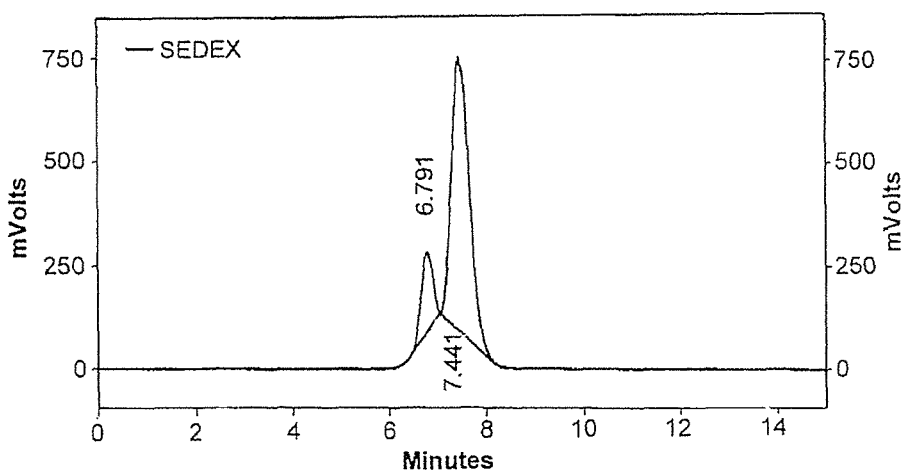

As can be seen from Table 2, the various reaction conditions yielded polymeric myrcene having calculated molecular weights in the range from about 3000 to about 46,000. The products may be designated as being in the range of "high" molecular weight polymeric myrcene i.e. <20,000 to about 50,000, and "low" molecular weight polymeric myrcene i.e. <3000 to ~11,000. Representative analytical SEC profiles for "high" and "low" molecular weight polymeric β-myrcene are shown in FIGS. 5A and 5B, respectively.

Reaction products washed with water yielded substantially identical results in analytical SEC.

Figure 6:
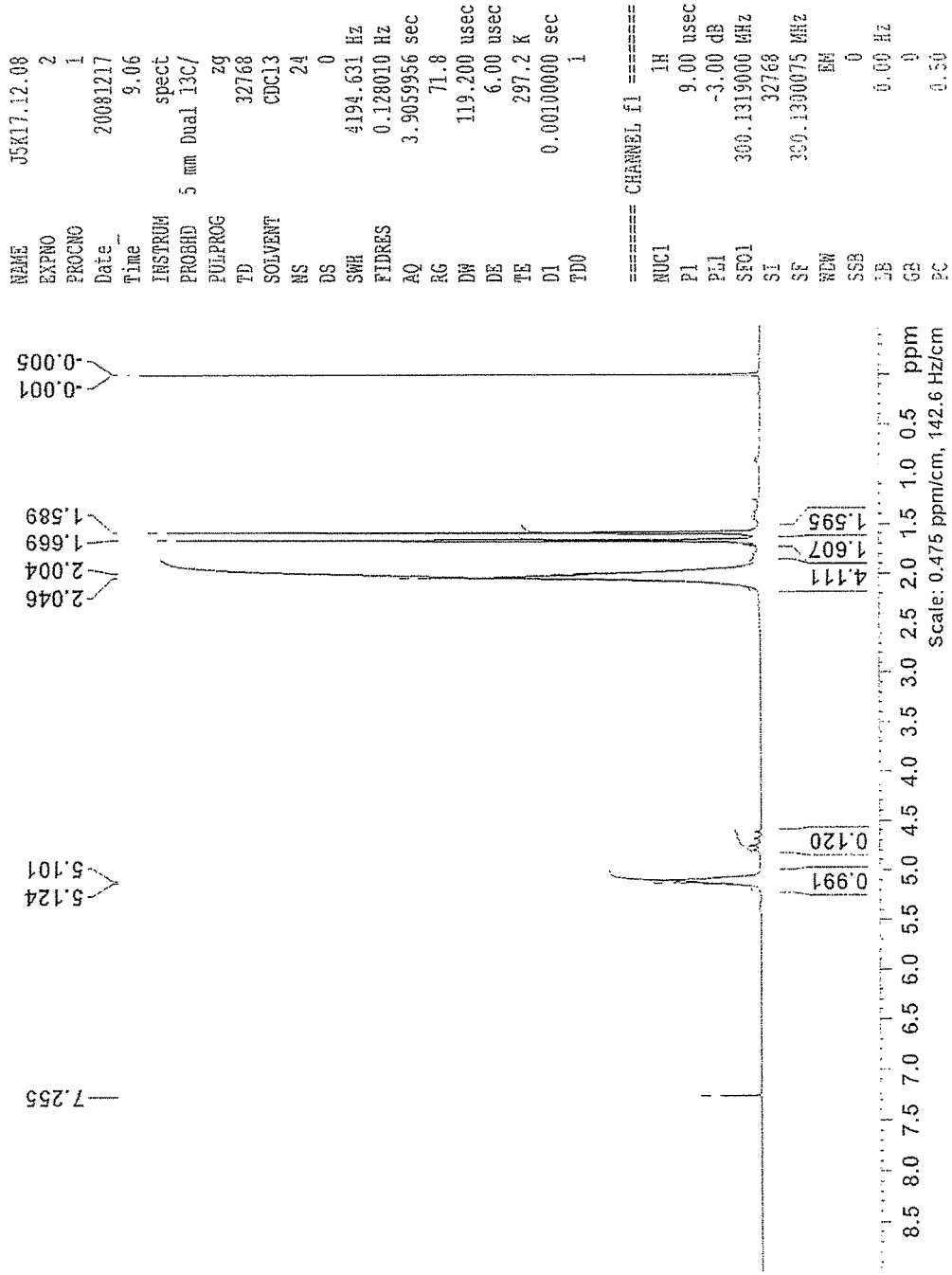
FIG. 6 shows the $^{13}$C-NMR spectrum of the synthesized 1,4-poly-β-myrcene.
Figure 7:
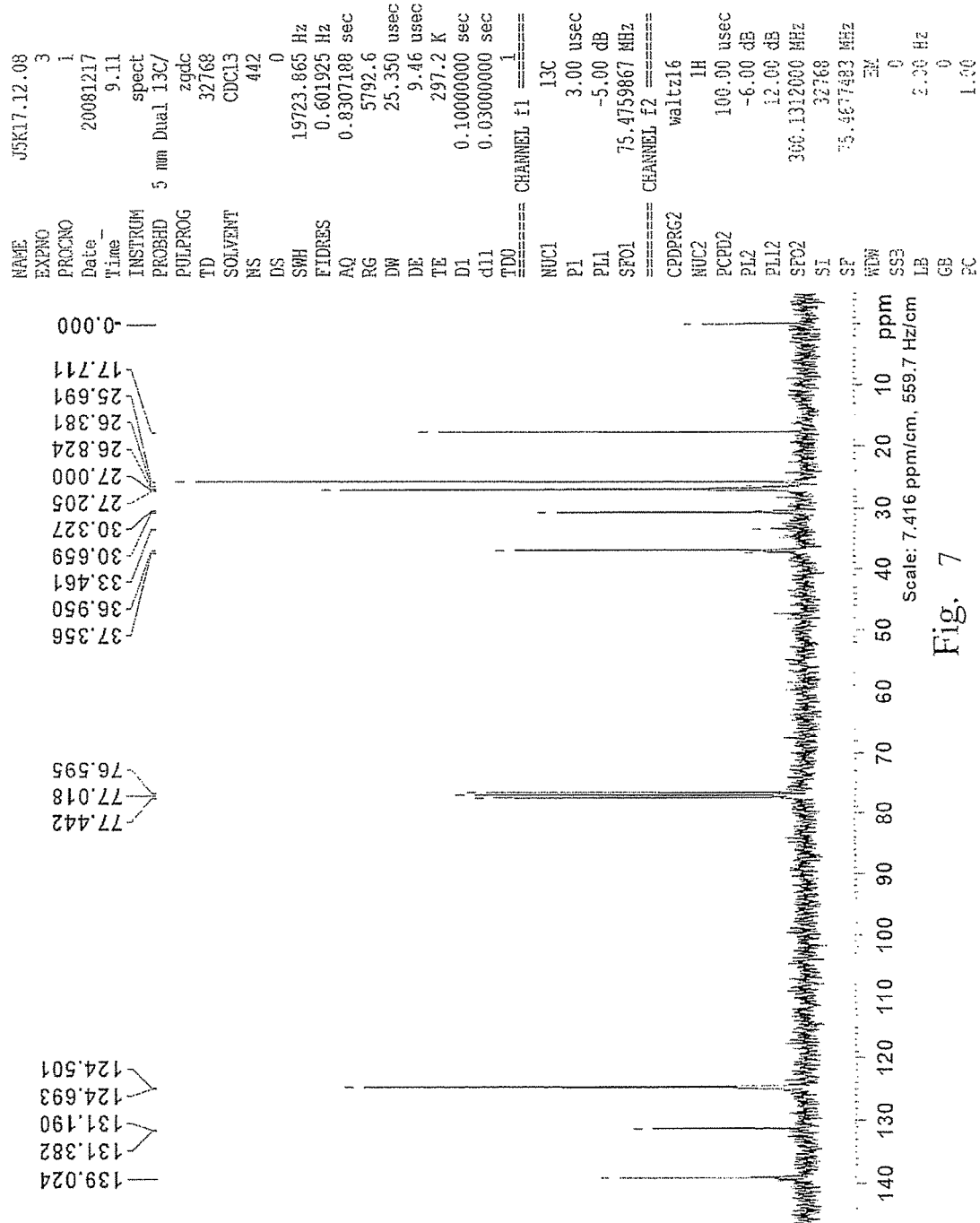
FIG. 7 shows the $^{13}$C-NMR spectrum of the synthesized 1,4-poly-β-myrcene.

FIG. 6 shows a representative $^1$H-NMR spectrum of the β-myrcene polymerization product. FIG. 7 shows a representative $^{13}$C-NMR spectrum of the β-myrcene polymerization product.

The $^1$H-NMR and $^{13}$C-NMR analyses indicate that the product of the polymerization reaction has a structure consistent with that of 1,4-poly-β-myrcene.

The synthetic reaction used for producing polymeric β-myrcene involves a mechanism of anionic polymerization (known as the "Michael reaction").

For initiation to be successful, the free energy of the initiation step must be favorable. Therefore, it is necessary to match the monomer with the appropriate strength of initiator so that the first addition is "downhill" A typical anionic reaction is the polymerization of styrene using butyllithium, $C_4H_9Li$, in an inert solvent such as n-hexane. When carried out under the appropriate conditions, termination reactions do not occur in anionic polymerization. One typically adds a compound such as water, an alcohol, molecular oxygen or carbon dioxide to terminate the propagation, due to rapid reaction with the carbanions at the chain ends.

Anionic polymerization gives rise to very sharp molecular mass distributions because transfer processes are absent. If the solvent is extremely pure, the polymer chains will still be active after all the monomer has been consumed.

The degree of polymerization is expressed as:

$$n = \frac{[M]}{[I]}$$

wherein M=monomer and I=initiator.

As indicated above, butyl lithium is an appropriate initiator for anionic polymerization for isoprene-containing molecules such as terpenes. Therefore, it has been used in the synthesis of 1,4-polymyrcenes for the present invention.

While the above described procedure is generally disclosed in the prior art (see for example Newmark et al (1988) J. Polym Sci. 26:71-77), important modifications disclosed herein are the work up in a high dilution of hexane and the final step of changing the solvent to oil, in order to obtain neat polymer which retains its biological activity with high potency.

Example 4. RPh-1 Induces Neuronal-Like Differentiation in Retinal Pigment Epithelial Cell Cultures Overview The present invention is directed to induction of differentiation and cell maturation, and has direct application to regeneration of functional tissue, in particular neuronal tissue. Our experimental findings show that RPh-1 induces differentiation of retinal pigment epithelial cells, an epithelial tissue of neuronal origin, to morphological neuronal cells producing axons, dendrites and junctions between cells known as synapses. The morphological differentiation in RPh-1 treated cells is accompanied by de novo expression of the neuron-specific differentiation antigen β3 tubulin. The induction of neuronal cell differentiation strongly suggests that RPh-1 affects neuronal stem cell differentiation into functional neurons. Current dogma on the pathology of dementia and Alzheimer's disease holds that the deficiency involves the failure of neurons to form functional synaptic junctions (see for example, Kimura R, Ohno M. Impairments in remote memory stabilization precede hippocampal synaptic and cognitive failures in 5XFAD Alzheimer mouse model. Neurobiol Dis. 2008 Nov. 5).

Accordingly, the experiments described herein support use of an isolated fraction of mastic as described in Example 1, as well as of polymeric myrcene, an active molecule in RPh-1, as a therapeutic modality to elicit neuro-regeneration in neurodegenerative diseases such as dementia and Alzheimer's disease.

Synthetic polymeric myrcene is also within the scope of the invention and is useful in the therapeutic methods of the invention.

Retinal Pigment Epithelium (RPE) Cells

Studies aimed at evaluating effects of RPh-1 on various cell lines of human origin led to use of ARPE-19 cells, a non-malignant human retinal pigment epithelial cell line.

The retinal pigment epithelium (RPE) is a single layer of hexagonal pigmented epithelial cells of neuronal origin, which forms the outermost cell layer of the eye retina and is attached to the underlying choroid. RPE functions include support, nourishment and protection of the underlying photoreceptors of the neuro-retina.

RPE cells are involved in the phagocytosis of the outer segment of photoreceptor cells, in the vitamin A cycle where they isomerize all-trans retinol to 11-cis retinal and in supplying the photoreceptors with D-glucose, amino acids and ascorbic acid.

Although in vivo the RPE is pigmented, ARPE-19 cells do not form melanin and are not pigmented. In culture the cells grow as spindle shaped and as polygonal cells.

Methods

ARPE-19 cells (obtained from the American Type Culture Collection, ATCC) were plated in flat bottom 96 well tissue culture microplates (Costar) at a concentration of $2-5\times10^3$ cells per well ($1-2.5\times10^4$ cells/mL) in a growth medium consisting of DMEM:Ham F-12, 1:1, supplemented with 10% Fetal Bovine Serum, 200 mM glutamine, 100 units/mL penicillin and 100 µg/mL streptomycin. The cells were allowed to adhere to the plate surfaces overnight prior to treatment with RPh-1.

RPh-1 was prepared essentially as described in Example 1, Method 1 to provide a 10% solution in a carrier composed of grape seed oil, olive oil, cottonseed oil, Mygliol® 810 or Mygliol® 812. The preparations were added to the cultures at volumes of 0.5 µl, 2 µl, 5 µl and 20 µl. These volumes, introduced into an overall sample medium volume of 200 µl, correspond to final RPh-1 concentrations of 0.025%, 0.1%, 0.25% and 1%, respectively. The oil carrier served as a vehicle control and was applied to control cultures at the same volumes.

The cultures were incubated in a 37° C., 5% $CO_2$ incubator for 72 hrs. The medium was then removed, the cultures washed twice with phosphate buffered saline (PBS), fixed with absolute methanol for 10 min and stained with Hemacolor® reagents (Boehringer Mannheim), which stain cells in a manner similar to Giemsa, and may be used in a quantitative cell viability assay (see Keisari, Y. A colorimetric microtiter assay for the quantitation of cytokine activity on adherent cells in tissue culture. *J. Immunol. Methods* 146, 155-161, 1992). The dye was eluted with 20% SDS, and quantified in an ELISA reader at 630 nm (triplicate samples evaluated). For determination of beta-3 tubulin expression, cells were plated on sterile glass coverslips immersed in 6 well microplates at a concentration of $10^5$ cells/well in a medium consisting of 1:1 mixture of Dulbecco's minimal essential medium (DMEM) and Ham F12 medium, supplemented with 10 fetal bovine serum and penicillin (100 units/ml), streptomycin (100 µg/ml) and glutamine (2 mM). The cells were allowed to adhere overnight to the coverslips and 7% RPh-1 in olive oil (or olive oil alone for control preparations) was administered to the cultures at a volume of 25 µl/ml medium and incubated at 37° C., 5% $CO_2$ for 72 hrs. The cells were then washed 2× with PBS and fixed with 4% para-formaldehyde. To determine beta-3 tubulin protein expression in the cells, the glass coverslips were stained with a mouse monoclonal primary antibody directed against human beta-3 tubulin followed by a secondary FITC-labelled anti-mouse IgG. The cell nuclei were counter stained with DAPI. Test and control preparations were then evaluated in a confocal microscope.

Results

Treatment of ARPE-19 RPE cells with RPh-1 was unexpectedly found to induce dramatic morphological changes that are unequivocally characteristic of neuro-differentiation. The morphological changes did not occur in control cultures treated with oil carrier alone, and similar results were seen among the test cultures treated with RPh-1, regardless of the oil used as the carrier for the active compound. The morphological changes were also associated with cessation in cell proliferation, further supporting the conclusion that RPh-1 induces neuro-differentiation.

Figure 8A:
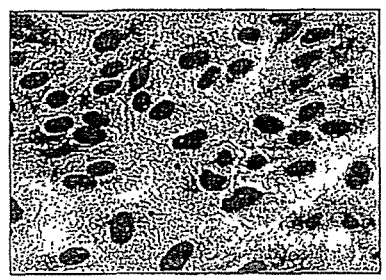
FIGS. 8A-D show the effects of RPh-1 on ARPE-19 cells.
Figure 8B:
Figure 8C:
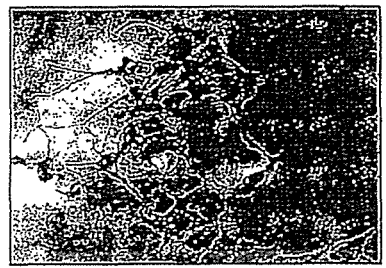
Figure 8D:
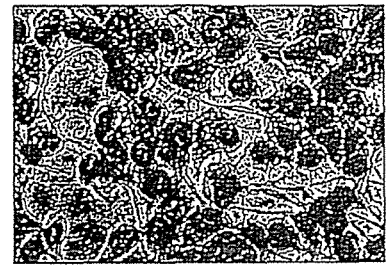

Control oil-treated cultures displayed the typical spindle shaped and polygonal growth pattern characteristic of ARPE-19 RPE cells (FIG. 8A). After 48 hours of incubation in culture, treated cells treated with RPh-1 (0.1%; 1 mg/ml) were altered in shape, and developed thick, densely staining very long single protrusions reminiscent of neuronal cell axons (FIG. 8B). After 48 hour of incubation, cells treated with RPh-1 (0.25%; 2.5 mg/ml) displayed a larger number of thinner long protrusions reminiscent of dendrites (FIG. 8C) after 72 hours of incubation with RPh-1 the thin long protrusions formed junctions with similar protrusions in adjacent cells creating a network of inter-connected cells, potentially capable of communicating information between one another (FIG. 8D). Similar networks occur normally between neurons in the central nervous system and enable transmission and processing of information.

While control cells proliferated during the 72 hour incubation period, RPh-1 treated cells rapidly ceased to proliferate and the cells remained in sparse density, further supporting the notion of cell differentiation.

Using inactive preparations of RPh-1 which did not induce differentiation as described above, ARPE-19 cells began to produce large amounts of melanin granules and these cultures continued to proliferate and cell density increased to confluence.

Figure 9:
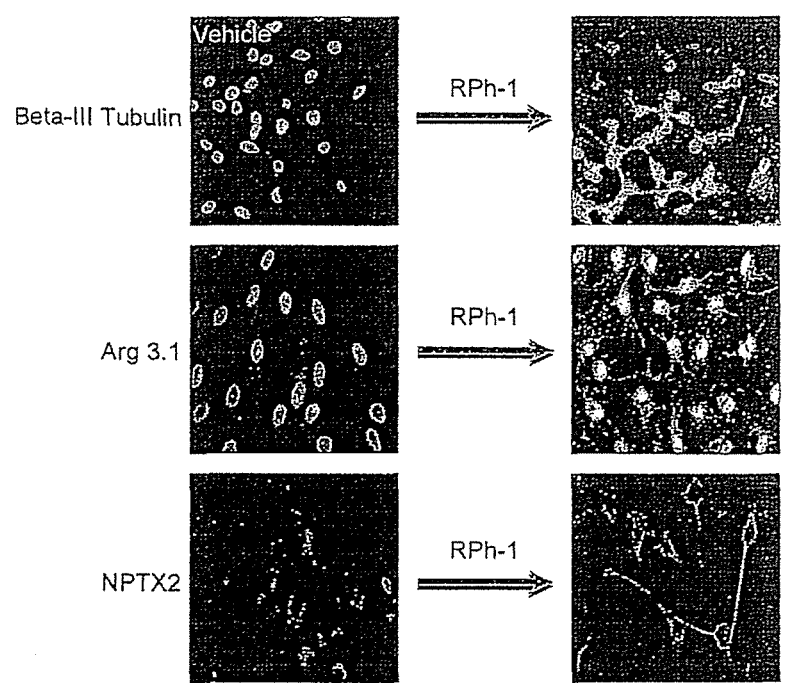
FIG. 9 shows immunofluorescence analysis of differentiated ARPE-19 cells before (left panels) and after (right) 72 hours of incubation with RPh-1, indicating expression of tubulin, beta 3 (TUBB3), activity-regulated cytoskeleton-associated protein (Arc/Arg3.1) and neuronal pentraxin II (NPTX2) following the treatment.

Treatment of ARPE-19 cells with RPh-1 (5% in cottonseed oil) was shown to result in expression of the neuronal and synaptogenesis markers β3 tubulin (TUBB3), a neuronal-type differentiation marker; Arc/Arg3.1, associated with synaptic plasticity; and neuronal pentraxin II (NPTX2), a neuronal immediate early gene that functions in excitatory synaptogenesis. Immunofluorescence analysis of differentiated ARPE-19 cells showed that after 72 hours of incubation with RPh-1, the cells stained positively for β3TUB, Arc/Arg3.1 and NPTX2 (FIG. 9, right panels), whereas little or no expression of these markers was seen prior to treatment (FIG. 9, left panels).

Figure 10:
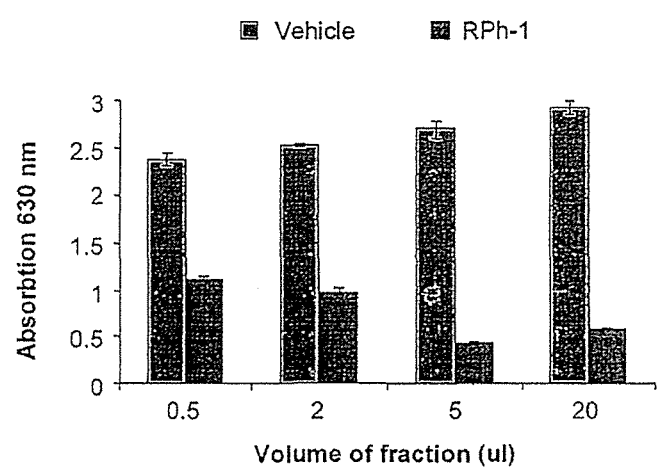
FIG. 10 shows the effect of RPh-1 on ARPE-19 cell proliferation as monitored by an assay to assess total protein content.

Evidence was further obtained that RPh-1 treatment of ARPE-19 cells leads to cessation in cell replication. Cells were treated with RPh-1 for 72 hours and the total protein content (related to the total number of cells present in the culture) was compared to untreated control ARPE-19 cells. As shown in FIG. 10, the RPh-1 treated cultures contained significantly lower protein content as compared to control cultures, confirming that cell proliferation was substantially terminated.

A Scoring System for the Potency of RPh-1 in Inducing Cell Differentiation

On the basis of the above results, a scoring system was developed to evaluate the potency of RPh-1 for inducing differentiation in cell culture, with cells plated $2 \times 10^3$ per well. The grades and their respective descriptions are set out in Table 3.

TABLE 3

| Grade | Description of Differentiation Effect |
|---|---|
| 0 | No effect. The cells proliferate, the cultures become confluent and the cells maintain their typical spindle shaped and polygonal morphology. |

TABLE 3-continued

| Grade | Description of Differentiation Effect |
|---|---|
| 1 | The cells produce pigmented granulation, yet continue to proliferate |
| 2 | Less than 10% of the cells undergo morphological changes to produce elongated, dendrite-like protrusions |
| 3 | Approximately 10-30% of the cells show elongated protrusions. Reduced cell proliferation compared to untreated control cells |
| 4 | More than 30% of cells form elongated dendrite-like protrusions that form junctions between adjacent cells as well as thick axon-like extensions. |
| 5 | The entire culture undergoes differentiation. The cells remain sparse and all of them undergo morphological changes that culminate in formation of elongated dendrite-like protrusions, axon like structures and intercellular junctions. |

Figure 11A:
FIGS. 11A-C show ARPE-19 cells of various grades of differentiation.
Figure 11B:
Figure 11C:
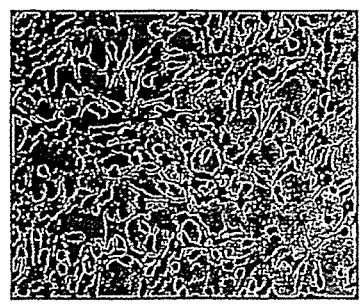

Representative examples of cell cultures at grades 3, 4 and 5 are presented in FIGS. 11A, 11B and 11C, respectively.

Example 5. RPh-1 Shortens the Recovery Period from Anesthesia

It is becoming increasingly evident that anesthesia is associated with neuronal damage, and safe effective methods are required for neuroprotection against such damage.

Methods

C57Bl/6 mice, 8 per group were injected with RPh-1 via the sub-cutaneous route three times over 7 days (every other day) with 0.05 ml of a 3% solution in grape seed oil for a dose of 30 mg/kg. The mice were then subjected to A sub-lethal dose (120 mg/kg) of ketamine was then administered to the mice. A control group was treated with 0.05 ml of the grape seed oil vehicle.

Results

Following anesthesia, the RPh-1 treated mice recovered significantly faster, as evidenced by their full mobility, while the controls were still immobile. Recovery in the control group as defined by an ability to become mobile took 3 minutes longer in the control group as compared to the RPh-1-treated group. This observation indicates that the active ingredient polymeric myrcene in RPh-1 shortens the recovery period from and can be used for neuroprotection against the adverse side effects associated with anaesthetic drugs.

Example 6. RPh-1 Induces Cell Differentiation Followed by Cell Death in Tumor Cell Lines The effects of RPh-1 on two melanoma cell lines and three neuroblastoma cell lines were investigated. Human melanoma cell line 5151 and murine melanoma cell line B16F10 both proliferate in tissue culture in an undifferentiated manner and do not produce melanin. Human neuroblastoma cell lines Lan-1, Lan-5 and SY5Y proliferate in culture as spindle shaped cells that do not exhibit differentiation morphology.

Methods

Cells were plated at $2 \times 10^3$ cells per well in 96 well flat bottom microplates (Costar) and cultured in 200 ml of medium DMEM (Dulbecco's medium) supplemented with 10 fetal bovine serum, 200 mM L-glutamine, 100 units/ml penicillin and 100 microgram/ml streptomycin (all reagents from Gibco-BRL). Following overnight attachment, RPh-1 (from a 10% solution in grape seed oil) was added to the cell cultures to provide final concentrations of 0.025%, 0.1%, 0.25% and 0.5%, and incubation was continued for 48 and 72 hours. The grape seed oil vehicle was used as control.

After 72 hours, cells were fixed with methanol and stained with Hemacolor® reagents (Boehringer Mannheim).
Results Treatment of melanoma cells with RPh-1 was found to induce formation of melanin after 24-48 hrs, as shown by FIG. 12B and FIG. 12C, as compared to the control treated cells in FIG. 12A. The RPh-1 treatment further caused arrest of replication, as shown by the decreased cell density, for example in FIG. 12D. By 72 hours, cell death was seen in cultures incubated with each of the four RPH-1 concentrations tested.

Upon treatment of neuroblastoma cell lines Lan-1, Lan-5 and SY5Y with RPh-1 (final concentration 0.025%), the cells began to develop dendrite-like protrusions and cell proliferation ceased. Higher RPh-1 concentrations caused cell death in the entire culture. Thus, the treatment with RPh-1 induced morphological neuron-like differentiation features that were followed by cell death.
Conclusion Polymeric myrcene, an active component in RPh-1, is associated with the induction of differentiation of various cell lines derived from the malignant cancers melanoma and neuroblastoma.

A block in terminal differentiation is recognized as a major avenue in the perpetuation of cell proliferation in cancer. Overcoming this block has already proven to be an effective treatment modality of several forms of cancer (e.g. retinoids in treatment of acute promyelocytic leukemia) and is now known as "targeted therapy". Targeted therapy does not kill cancerous cells but modifies their behavior, primarily by inducing differentiation. Accordingly, the aggressiveness of many cancers can be reduced.

As disclosed herein, polymeric myrcene, an active ingredient of RPh-1 has been found to overcome the block in tumor cell differentiation, as indicated by formation of neuronal cell dendrites in neuroblastoma cell lines, and induction of melanin formation in melanoma cell lines. In both cases these changes were associated with cessation in cell proliferation and cell death.

Example 7. Chemically Synthesized Polymeric Myrcene Induces Cell Differentiation in Retinal Pigment Epithelial Cell Cultures Experiments were carried out to determine whether synthetic polymeric myrcene of two different molecular weight ranges induces neuro-differentiation in ARPE-19 cells.
Methods ARPE-19 cells were plated in flat bottom 96 well tissue culture microplates (BIOFIL) at a concentrations of $5\times10^3$ cells per well ($2.5\times10^4$ cells/mL) in a growth medium consisting of DMEM:Ham F-12, 1:1, supplemented with 10% Fetal Bovine Serum, 200 mM glutamine, 100 units/mL penicillin and 100 µg/mL streptomycin. The cells were allowed to adhere to the plate surfaces overnight prior to treatment with the chemically synthesized polymeric myrcene fractions.

Figure 13A:
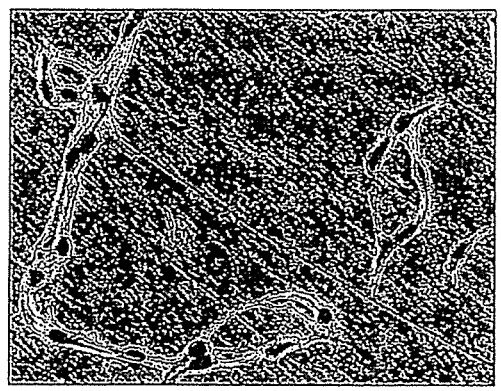
FIGS. 13A-B show the effects of chemically synthesized polymeric myrcene on RPh-1 cells.
Figure 13B:
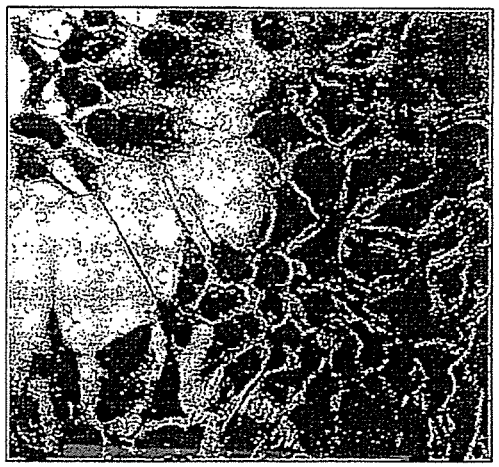

Isolated fractions of chemically synthesized polymeric myrcene, having distinct molecular weights were tested for activity in the RPE cell differentiation assay. Fraction 18-1 (molecular weight in the range of about 50,000 daltons), and fraction 18-2 (molecular weight in the range of about 20,000 daltons), described in Example 3 were used. Fractions 18-1 and 18-2, and RPh-1 were each prepared at a concentration of 10% in olive oil. Each preparation was added to the ARPE-19 cell cultures using volumes of 0.5 µl, 2 µl, 5 µl and 20 µl, corresponding to final concentrations of 0.025%, 0.1%, 0.25% and 1%, respectively. Olive oil served as vehicle control and was applied to control cultures at the same volumes. The cultures were incubated in a 37° C., 5% $CO_2$ incubator for 72 hrs. The medium was then removed, the cultures washed twice with phosphate buffered saline (PBS), fixed with absolute methanol for 10 min and stained with Hemacolor® reagents.
Results Both Fractions 18-1 and 18-2 were shown to have activity in inducing neuro-differentiation in ARPE-19 cells (FIG. 13 and Table 4). Optimal activity was observed with Fraction 18-1 at 0.25% (as shown in FIG. 13A), while 0.1% was somewhat effective and 0.025% had no effect (Table 4). The effect of fraction 18-2 is shown in FIG. 13B.

TABLE 4

Effects of Fractions 18-1 and 18-2 on ARPE-19 cell differentiation

| Fraction | Volume (ul) | Results |
| --- | --- | --- |
| 18-1 | 0.5 | High cell density. No differentiation |
|  | 2 | High density. Differentiated cells |
|  | 5 | Lower density. Differentiated cells. Long axons with intercellular junctions |
|  | 20 | Cell death |
| 18-2 | 0.5 | Low density. Few full differentiated cells. |
|  | 2 | Differentiated cells but axons shorter and less prevalent than 18-1 |
|  | 5-20 | Cell death |
| RPh-1 | 0.5 | Differentiated cells in clusters. Long axons |
|  | 2 | Differentiated cells with lower density. Long axons |
|  | 5-20 | Cell death |
| Oil Vehicle | 0.5-20 | Very high cell density, no differentiation |

Conclusion

The observed results support the conclusion that RPh-1, a formulation of an isolated fraction of mastic gum, has activity in inducing differentiation of neuronal cells.

The observed results also support the conclusion that polymeric myrcene, whether isolated from a plant source or that chemically synthesized, has activity in inducing differentiation of neuronal cells.

Example 8. The Effect of RPh-1 in Inducing Cell Differentiation is Blocked by the Polar Solvent-Soluble Fraction Present in Mastic Resin Overview Mastic resin and various compounds identified therein have been associated with a variety of beneficial biological and therapeutic activities. Various prior art disclosures indicate that the biological activity is associated with a fraction that is obtained by extraction of mastic with a polar solvent, and recovery of the polar solvent-soluble material. In contrast, RPh-1 is a fraction which has been isolated from mastic resin on the basis of its being soluble in both polar organic solvents and non-polar organic solvents, while compounds that are soluble only in polar organic solvents but not in non-polar organic solvents are discarded (the latter herein designated Fraction SP). A major component in RPh-1 is polymeric myrcene, as shown in Example 2. This compound however, has not previously been attributed with beneficial effects, but rather has been acknowledged to interfere with oral administration and bioavailability of active compounds present in mastic resin. Fraction SP corresponds to prior art mastic fractions which have been attributed to have various beneficial biological activities. The aim of the present study was to assess the effect of SP on the cell differentiation effect exerted by RPh-1. It is now disclosed that compounds present in SP interfere with and block the cell differentiation effects induced by RPh-1.

Methods

Mastic resin was treated to obtain RPh-1, essentially as described in Method 1 of Example 1, using ethanol as the polar solvent. The ethanol-soluble fraction was decanted off from the insoluble material to obtain Fraction SP. Mixtures of RPh-1 and Fraction SP in differing proportions were prepared as follows:

| Mixture | RPh-1 (%) | Fraction SP (%) |
|---------|-----------|-----------------|
| A0 | 95 | 5 |
| A1 | 90 | 10 |
| A2 | 80 | 20 |
| A3 | 70 | 30 |
| A4 | 50 | 50 |
| A5 | 25 | 75 |

In addition, whole mastic dissolved in oil (warmed to 60° C.) was prepared to obtain preparation TC.

The results of the study, summarized in Table 5, indicate that fractions rich in RPh-1 (A0 and A1) were effective in inducing ARPE-19 differentiation. The morphological changes seen in these cultures were similar to that shown in FIGS. 8B and 8C. As the proportion of Fraction SP was increased in the mixtures, cell death increased, with no cell differentiation observed. Cells in cultures treated with SP alone were dead at all tested doses, and fraction TC exerted only negligible effect.

These results show that the potent neuro-differentiation inducing activities were only contributed by the polymers in RPh-1 whereas the SP polar fraction only caused cell death.

TABLE 5

Effects of mixtures of RPh-1 and SP on cell differentiation

| Fraction | Volume (ul) | Results |
|----------|-------------|---------|
| A0 | 0.5 | High cell density, differentiated cells. |
|    | 2 | Lower cell density. Differentiated cells with long axons. |
|    | 5-20 | Cell death. |
| A1 | 0.5 | High cell density. Less differentiated cells than in A0. |
|    | 2 | Differentiation. |
|    | 5 | Low cell density. Differentiated cells with long axons. |
|    | 20 | Cell death. |
| A2 | 0.5 | Low cell density. Differentiation. |
|    | 2 | Partially differentiated cells (only short dendrites) associated with cell death |
|    | 20 | Cell death. |
| A3 | 0.5 | Sporadic, partial differentiation. High cell density (cell proliferation). |
|    | 2-20 | Cell death. |
| A4 | 0.5 | Cell death, toxic |
|    | 2-20 | Cell death. |
| A5 | 0.5-20 | Cell death. |
| RPh-1 | 2 | Differentiated cells with intercellular junctions and long axons |
|    | 5 | Differentiation and long axons |
|    | 20 | Cell death. |
| SP | 0.5-20 | Cell death. |
| TC | 0.5 | Negligible effects |
|    | 2 | Cell death. |
| Vehicle | 0.5-20 | High density |

Example 9. Wound Healing in Dogs

An aging Golden Retriever male dog had an open chronic leg wound for more than 6 months. The dermal lesion was associated with alopecia (loss of fur) and depigmentation of the surrounding fur. The dog was treated by several cycles of topical treatment with RPh-1. Following the initial application, transient edema with swelling occurred for 16-20 hrs. This was followed by de novo formation of functional epithelial tissue (epithelization) and neoangiogenesis (novel formation of microvasculature) with normal tissue contours, resulting from rapid and vigorous formations of granulation tissue. Wound healing contracted inwards towards the center of the wound, suggesting the presence of fibro-myocytes (of mesodermal origin).

Figure 14A:
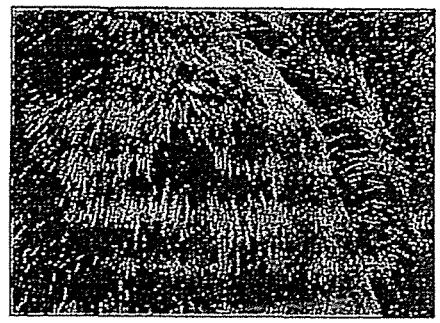
FIGS. 14A-B shows regeneration of fur in an aging Golden Retriever male dog afflicted with a dermal lesion associated with alopecia following treatment with RPh-1.
Figure 14B:
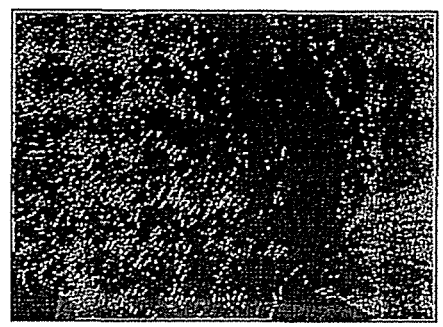

The wound was completely healed within approximately 12 weeks with predominantly functional skin and re-growth of the fur. FIG. 14 shows the afflicted area before (FIG. 14A) and after (FIG. 14B) treatment with RPh-1.

In another aging male dog afflicted by alopecia, topical treatment with RPh-1 resulted in re-growth of the fur to become integrated with the surrounding fur.

A different dog had a jaw tumor (non-induced), portions of which protruded into the buccal cavity. The protruding portions were surgically excised, while the sections of the tumor that were embedded within the jaw could not be removed. The tumor was diagnosed as a sarcoma. RPh-1 formulated in grape seed oil was applied to the affected jaw area. The treatment brought about complete cure of the gums covering the surgical incision site to the extent that no scar was left and the surgical incision site was no longer discernable. Even the expected recurrence of the tumor from portions embedded in the jaw was prevented for an extended interval of several weeks. The treatment with RPh-1 induced an extraordinarily rapid healing of the surgical incision site and complete regeneration of the gums.

In both of the above cases, wound healing was accompanied by a general increase in vitality, mental awareness and physical activity in the treated dogs.

The above results support the use of polymeric myrcene, the active component of RPh-1, for wound healing, regeneration of hair follicles and reversal of neurological degeneration.

Example 10. Treatment of Wounds in Fish

Gold fish as well as koi fish (both in the carp family) are prone to integument ulcers caused by bacteria, in particular *Aeuromonas hydrophila*.

Gold fish weighing approximately 100 gram each, which had developed bacterial ulcerations were divided into two groups in separate tanks, each group containing four fish. Each tank was filled with a volume of 100 liters of water and maintained under aeration with an air pump. The groups were randomized by weight and wound size (in the range of 1-1.5 cm by 1-1.5 cm). Each fish was injected intramuscularly through intact integument at a site approximately 5 mm from an ulcer with 20 microliters of either grape seed oil alone (control group), or a 1% solution of RPh-1 in grape seed oil (treatment group).

Fish in the test group began to improve progressively following 4 cycles of treatment with RPh-1 and were healed over a period of a month. All fish in this group survived through the six week duration of the study. These fish also exhibited alert and responsive behavior including active swimming, searching for and snatching at food provided at the water surface, and rapid, startled movement away in response to percussion on the wall of the tank.

In contrast, fish in the control group displayed no improvement in the condition of their ulcers. The fish were lethargic, exhibited sedentary behavior at the bottom of the tank, and did not respond to stimulation. All of the fish in this group died by the end of six weeks.

The differences between these two groups were highly significant in both parameters: fish survival and wound closure.

Example 11. Effect of RPh-1 in Wound Healing Using B6.V-Lepob/Olahsd Mice Model

B6.V-Lepob/OlaHsd (ob/ob) mice (express obesity at age 4 weeks) were used to evaluate the effect of RPh-1 in wound healing. Full thickness skin puncture was performed using a disposable biopsy puncher (Uni-Punch® Disposable Biopsy Punch, Premier) in the distal zone of each mouse back. The puncture has an ellipse shape. Average long axis length of punctures ranged between 5.1 to 5.3 mm. The average width axis length of punctures ranged between 4.8 to 5.1 mm RPh-1 (5%) in olive oil was injected subcutaneously at two sites surrounding the wound at a distance of 3-5 millimeters from the edge of the wound (Group A, n=6) or topically onto the wound (Group B, n=6). Vehicle was applied topically onto the wounds of mice (Group C, n=6). Thereafter, RPh1 (5%) was applied 3 times a week, 7 times in total, during the 16 days of the study at a 20 ul dose volume (injection) or a 50 ul dose volume (topical administration).

Figure 15:
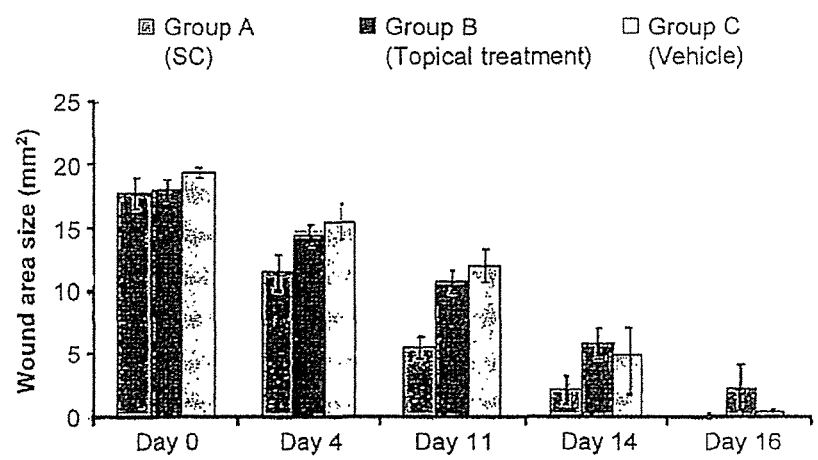
FIG. 15 shows the effect of RPh-1 on wound healing of inflicted wounds in experimental mice as indicated by the wound size (mm$^2$) at various time points after wound infliction in mice treated with RPh-1 by SC injection (Group A, grey bars), topically (Group B, black bars) and in mice treated with vehicle alone (Group C, open bars).

FIG. 15 shows that at day 11 following wound infliction, the size of the wound (wound area) was significantly reduced in mice treated with RPh-1 (Group A) as compared to those treated with vehicle alone (p=0.005) (Group C). The rate of wound healing during the period from Day 0 to Day 11 following wound infliction was significantly more rapid in mice treated with RPh-1 as compared to those treated with vehicle alone (p-0.034).

Example 12. Effect of RPh-1 in Reversing the Neurodegenerative Effects of Chronic Cerebral Hypoperfusion (Vascular Dementia) in a Rat Model Vascular dementia (VD) is a subtype of dementia with a prevalence that is second only to that of Alzheimer's disease in westernized societies. VD causes many neuropsychiatric and physical problems, and represents a significant economic burden. Brain imaging has revealed obvious changes in the cerebral cortex and white matter, and these lesions are thought to be the core pathology for cognitive declines in patients with vascular dementia (see for example, Farkas et al., Experimental cerebral hypoperfusion induces white matter injury and microglial activation in the rat brain. Acta Neuropathol. 2004; 108:57-64; Stenset et al., White matter lesion subtypes and cognitive deficits in patients with memory impairment. Dement Geriatr Cogn Disord. 2008 26: 424-431).

Cerebral lesions can be experimentally induced in rat brains by permanent occlusion of both common carotid arteries which can affect cognitive function. This model is similar to vascular dementia and the experimental technique can decrease the blood flow in the cerebral cortex and hippocampus by up to 40-80% for several months, inducing certain learning disorders. Thus this model was used to study the effects of RPh-1 treatment in reversing the deficiencies caused by vascular dementia lesions.

A total of 40 animals were randomized into 3 groups i.e. an untreated sham control group, a vehicle control group and an RPh-1 treated group (10-15 animals per group). They were randomized into 3 groups, an untreated sham control group, a vehicle control and an RPh-1 treated group. Ten μl of RPh-1 (5% in cottonseed oil) or vehicle was administered subcutaneously 2x/wk, with the first dose administered 14 days after induction of vascular dementia.

The Morris water maze (MWM) test is sensitive to hippocampal function. The water maze task is performed to evaluate two CCA-related learning deficits using the method described previously (Watanabe et al., Cilostazol Stroke. 2006; 37(6):1539-1545). In a 160-cm diameter circular pool filled with 20-cm deep water, a circular transparent acrylic platform is prepared, the top surface of which is 3 cm below the water. Rats are released facing the wall, and the time taken to escape to the platform is recorded as the escape latency. Tests are performed on day 3 before CCA occlusion and on days 14, 35, 56, 84 and 112 after CCA occlusion. On training days six training trials are conducted per day with an inter-trial interval of 2 min. Animals are placed in the pool at one of six starting positions. In each training trial, the time and path length required to escape onto the hidden platform are recorded. Results of six training trials are averaged to obtain a single representative value, and the averages are used for final statistical analyses. Animals that found the platform are allowed to remain on the platform for 30 sec. Animals that do not find the platform within 90 sec are softly guided to the platform for 30 sec at the end of the trial.

Performance of RPh-1-treated animals (cross-hatched bars), vehicle treated animals (open bars) and in sham control animals (black bars) were tested for frequency in platform location (FIG. 16A); the time spent in platform area (FIG. 16B); the latency to find the platform (FIG. 16C); the frequency in zone 1 location (FIG. 16D); the time spent in light part (FIG. 16E); the latency to find the platform (FIG. 16F); and the velocity (FIG. 16G). All tests showed significantly higher performance in the RPh-1-treated animals as compared to at least one of the control groups.

Example 13. Pathologic Weight Control Regulation Effect of RPh-1 (Orexigenic and Anti Obesity Effect)

The dogs with various wounds described in Example 9 additionally suffered from loss of appetite and would not eat food placed in front of them. Following after approximately 10 days of treatment with RPh-1 as described, dogs gradually re-gained interest in food and started to eat. Within a month, the dogs showed strong interest in food and appetite was similar to that of normal healthy dogs.

The fish with ulcerations described in Example 10 additionally suffered from loss of appetite. The control group continued to ignore food applied into the water, whereas the fish treated with RPh-1 responded eagerly with rapid movement in response to administration of food.

Rats described in Example 12 additionally suffered from weight loss after chronic cerebral hypoperfusion. After 35 days of treatment (day 56 of study) rats treated with RPh-1 as described, recovered their weight significantly faster than animals treated with vehicle (FIG. 17A).

Mice described in Example 11 generally suffer from obesity as a result of mutation leptin gene. FIG. 17B shows that subcutaneous administration of RPh-1 to mice (Group A; diamond symbols), causes a significant lower body weight gain compared to vehicle treated animals (Group C; triangle symbols) or animals treated by topical administration of RPh-1 (Group B; square symbols). Mice of group A gained 4.9% during the 11 days. The body weight gain was compared of the initial (day 0) body weight. The body weight gain of group A is significantly lower than the mean body weight gain of mice in group B (p value=0.02, T-TEST, Excel). Mice of group C were similar (p=0.08) to mice of group B and gained body weight significantly different (p value=0.04) from mice of group A. Mice of group B and C gained 10.2% and 9.1% respectively. The rate of body weight gain in all groups as expressed by the slopes was similar (p=0.07 (A vs. B), 0.08 (A vs. C) and 0.43 (B vs. C).

The above observations support the conclusion that RPh-1 is regulator of pathological weight disorder and can serve as an orexigenic (appetite stimulant) or anti-obesity agent.

Example 14. Effect of RPh-1 in Transient Middle Cerebral Artery Occlusion (tMCAO) Stroke Model in Rats In a study to assess the ability of RPh-1 to prevent or reverse neurological deficit as a result of ischemia utilizing the rat transient middle cerebral arterial occlusion model (tMCAO), RPh-1 (5% in cottonseed oil) was administered subcutaneously at a 10 ul dose and first administration was done 3 h after the surgical procedure and then twice weekly until termination of the study on day 28. During the study neurological, motor and somatosensory functions were tested in a battery of behavioral tests.

Throughout the study no significant differences in general physiological conditions, body weight gain or general clinical signs between the two groups were observed.

Clear differences were seen between the RPh-1 treated group and the vehicle treated control group in neurological function recovery after stroke during the 28 days following stroke. In general, accelerated and improved recovery was demonstrated in animals that were treated with RPh-1. Somatosensory functions were most sensitive to the treatment, and significant response was demonstrated as early as day 8 following stroke (FIGS. 18A and 18C). Assessment of Neuroscore showed significant differences were seen only in rats treated with RPh-1 (Group A), between day 8 and day 14, and between day 8 and day 28 (FIG. 18A). Neurological recovery as assessed by the patch removal test was significant only in rats treated with RPh-1 (Group A) between day 2 and the other days (FIG. 18C). Motor function improvement, as assessed by the stepping test, was significant only in rats treated with RPh-1 (black bars), by day 28 (FIG. 18B).

Example 15. Effect of RPh-1 on Retinal Ganglion Cells (RGC)

Axotomy of the optic nerve was performed on the right eye of deeply anesthetized rats (19 rats per group). The test group received a sub-dermal injection in the posterior neck area of RPh-1 (5% in cottonseed oil); 0.025 ml/injection), and the control group was similarly injected with the same volume of vehicle. The first injection was given to all the animals directly after surgery. Subsequent injections (same dosage and method of administration) were administered twice a week, every 3 to 4 days.

Fourteen days after axotomy, a fluorescent retrograde neurotracer (Di-Asp) was inserted into the axotomized optic nerve in order to stain surviving Retinal Ganglion Cells (RGC), and 24 hours later, the rats were sacrificed in a $CO_2$ saturated chamber and the injured right eye was enucleated. The retinas were isolated, flattened on a slide and fixed with xylene based mounting medium.

Whole-mount retinas were evaluated with a fluorescent microscope. Dyed cells were counted manually. The average number of RGC per group is shown in FIG. 19, showing a significantly higher number of cells in the RPh-1 test group.

Example 16. Retinal Detachment (RD) Model

Retinal detachment (RD) was performed on the right eye of deeply anesthetized animals (xylazine 50 mg/kg and ketamine 35 mg/kg) following dilatation of the pupil with Tropicamide drops 0.5%. RD was induced through the generation of a small opening in the retina at the ora serata followed by a sub-retinal injection of 5 µl saline with a 30 G syringe needle. Approximately half of the retinal area was detached by this procedure.

Rats with RD were divided into two experimental groups, with the test group receiving a sub-dermal injection in the posterior neck area of RPh-1 (5% in cottonseed oil; 0.025 ml/injection), and the control group injected with the same volume of vehicle. The first injection was given to all the animals directly after surgery. The second injection (same dosage and method of administration) was administered 48 hours after surgery.

On days 3 and 14 days after RD, the operated rats were euthanized in a $CO_2$ saturated chamber. The injured right eye and the untreated left eye were enucleated. The retinas were isolated, frozen on dry ice and processed for Western blot analysis or immunohistochemical analysis. The left eye retinas served as non-operated controls.

The expression levels of Semaphorin3A (Sema3A), Neuropilinl (NP1), and GAP43 were studied, Caspase3 was used as a apoptotic marker, and morphological changes in Müller and microglial cells were examined.

Sema3A is an axonal growth inhibitor that has been shown to be involved in retinal ganglion cell loss following injury to the optic nerve. High levels of Sema3A were detected in retinas after RD as shown by Western blot analysis (FIG. 20A). Treatment with RPh-1 clearly decreased Sema3A expression levels, both in control non-injured retinas and those with RD (FIG. 20A). Samples were normalized to beta-actin expression (lower band, FIG. 20A).

Immunohistochemical analysis of 20 µm retinal sections incubated with anti-Sema3A antibody and the nuclear dye Sytox Blue showed that Sema3A expression was clearly higher in detached retinas as compared to the controls. Sema3A expression was observed mainly around the retinal ganglion cells. Similar to the results observed in Western blot analysis, Sema3A expression was reduced in RD animals treated with RPh-1.

NP1 is a functional Sema3A receptor. TUNEL-positive cells, indicating apoptotic processes, were evident 24 hours post retinal detachment and increased after 7 days.

Caspase-3 was activated in response to RD. However, caspase-3 was elevation was significantly attenuated in RD animals treated with RPh-1 (FIG. 20B).

GAP43 is an intracellular protein that is tightly connected to the membrane of the growth cones. It is normally expressed during the process of synaptogenesis. In the retina, GAP43 is expressed in the neurons at an early stage of embryogenesis, while the optic nerve is still elongating. In the rat optic nerve, GAP43 is found both in axons and cell bodies of RGCs, but the expression disappears at the age of 8 to 16 weeks, and is found again following ischemia or injury to the optic nerve.

The morphological changes of the Muller cells were studied by staining for glial fibrillary acidic protein (GFAP). GFAP labels Muller cells in the retina, and is commonly used as a stress indicator. GFAP labeling in the intact control retina was concentrated at the GCL. Immunohistochemical analysis showed elevated levels of GFAP in the detached retinas in comparison to controls. Detached retinas treated with RPh-1 exhibited higher GFAP levels.

Microglial invasion and activation are regarded as harmful or beneficial to neurons. Microglial activation after acute CNS injury is primarily a reactive and adaptive glial cell response, which is triggered by injured neurons and which is designed to ameliorate primary tissue damage and to promote subsequent repair and gliosis (glial scar) as a result. Microglia become activated in the retina usually after injury stimulate and recruit endothelial cells and fibroblasts. Immunohistochemical analysis of sections of detached and non-injured retinas labeled with IB4 and stained with the nuclear dye PI showed evidence of activated microglial cells in detached retinas only. However, in detached retinas from animals treated with RPh-1, less microglial activation was evident as compared to detached retinas from animals that were treated with vehicle.

The results showed reduced recruitment of active microglia around an injury region and support a scar-less repair mechanism of wounds.

Example 17. Preparation of Complexes of Cyclodextrin with Polymeric Myrcene

Cyclodextrins, by virtue of their ability to form inclusion complexes with many drugs, can substantially increase the aqueous solubility of biopharmaceuticals, in particular those that are defined as water-insoluble such as polymeric myrcene. Cyclodextrins are water-soluble compounds, which can form reversible complexes with poorly water-soluble molecules resulting in a soluble molecular inclusion complex. When the inclusion complex of the drug-cyclodextrin combination is diluted in a sufficiently large volume of water or blood, it dissociates rapidly, releasing the sequestered pharmacologically active agent.

Complexation of polymeric myrcene with β-HPCD will be performed as follows:
a. Dissolution of pre weighed polymeric myrcene in a minimum amount of non-polar solvent such as hexane, heptane, or the like.
b. Dropwise addition of the non-polar solvent to the β-HPCD powder.
c. Drying at 50-80° C. until non-polar solvent evaporates.
d. Mixing with necessary amount of water.
e. Dissolution with sonication and heating.
f. Filtration through 0.2-0.45 μm filter.

Example 18. Preparation of Nanoemulsions of Polymeric Myrcene

Liquid oil-in-water nanoemulsion formulations are to be prepared by high pressure emulsification techniques of all lipid ingredients and the active component polymeric myrcene dissolved in the lipid oil phase and emulsified with an aqueous phase, projected to result in the formation of stable, spheric and uniformly dispersed drug-containing lipid nanodroplets. The emulsion droplet size reduction is essential to generate drug formulations with high stability. Preferred nanoemulsion droplets have a mean droplet size of less than one micron (generally in the range of 0.1-0.2 μm) uniformly dispersed in an aqueous phase. The uniqueness of the large internal hydrophobic oil core of the nanoemulsion droplets provides high solubilization capacity for water insoluble compounds such as polymeric myrcenes.

1. Preparation of Oil Phase
The oil phase is composed of 13% lipoid E-75, 0.026% αTP-succinate, propylparaben as antioxidant and 86.9% Miglyol® 810. Polymeric myrcene prepared as in Example 1 is dissolved in the oil phase. The components are mixed with mild heating until a homogenous completely solubilized solution is obtained.

2. Preparation of Aqueous Phase
The aqueous phase is composed of 0.1% EDTA, 0.5% Tween-80, 2.3% glycerol, methylparaben as preservative and 97.1% water. pH was adjusted to 7.4 by NaOH 1N.

3. Mixing of Oil and Aqueous Phases
Oil phase (3.7 g) is heated and added to 70 ml of the aqueous phase (preheated). The mixture is gently stirred for 10-15 min at room temperature.

4. Preparation of Oil-in-Water Coarse Emulsion
An oil-in-water emulsion is prepared using the medium size dispenser and high shear homogenizing unit Polytron®, at 20,000 rpm for 5 min.

5. Sizing the Emulsion to Submicron Range by Gaulin® High Pressure Homogenizer
The droplet size of the emulsion obtained after step 4 is reduced to the submicron (nanosize) range by submitting the emulsion to high shear homogenization using the Gaulin® Microlab 70 high pressure homogenizer at 800 bar pressure. A total of 5-6 cycles should be performed to obtain homogenous nanoemulsion droplets having average particle size of less than 200 nm. Particle size is to be determined by photon correlation spectroscopy (PCS) using a N4MD particle size analyzer (Coulter® Electronics, UK). When most of the particles (>90%) are smaller than 200 nm, the sizing process is determined to be complete.

6. Sterile Filtration
Filtration at aseptic conditions of the nanoemulsion to sterile vials using a 0.2 μm PES sterile filter and storage at 40° C.

Example 19. Preparation of Spray-Dried Polymeric Myrcene Powder

A convenient process for manufacturing the polymeric myrcene-lipid mixture product is by direct spray-drying of the formulation from a mixture of non-polar solvent dispersion containing all the lipid ingredients and water containing the hydrophilic components, taking into account cost effectiveness and upscaling considerations. The selected spray-drying method is optimized in order to get a fine, free-flowing powder. Polymeric myrcene is dissolved in the lipid phase containing the lipid ingredients lecithin, tricaprin (capric acid triglyceride), tocopherol succinate and warmed (~40° C.) in a nonpolar solvent until a good dispersion is obtained. A dispersion of fumed silicon dioxide (Cab-O-Sil®) in water (5%) was prepared by swelling the powder in purified water. The resultant slurry (prewarmed to 40° C.) is then poured slowly into the nonpolar solvent lipid dispersion and the mixture is agitated at 40° C. for about 1 hr until a homogenous dispersion is obtained. The mixture is then spray-dried using the Yamato Pulvis® GA32 spray-dryer. The spray-drying conditions are: flow rate 7 ml/min, inlet temperature 130° C., outlet temperature 70° C., and drying air flow 0.5 m³/min. A homogeneous dry powder containing the polymeric myrcene-lipid mixture is expected to be obtained.

The polymeric myrcene-lipid mixture formulation prepared by the direct spray drying process is expected to show good water dispersibility, thus being suitable for the preparation of solid-dosage forms such as hard gelatin capsules or tablets for the enhanced oral delivery of polymeric myrcene with potential good oral bioavailability.

Example 20. Preparation of Liposomal Preparations Containing Polymeric Myrcene

Lipids containing dissolved polymeric myrcenes were dissolved in 100 ml dichloromethane in a round bottom flask, and stirred for 30 min at room temperature until a clear transparent solution was obtained. Solvent will be evaporated using a rotary evaporation unit at 39° C. First, the flask will be rotated at 4.5 rpm, 5 min under atmospheric pressure, followed by 10-30 min (until full evaporation of the solvent) under weak vacuum, and finally 15 min under full vacuum. At the end of the evaporation process a uniform lipid film will be created. The lipid film will be dissolved in 15 ml isotonic buffer. Liposomes are prepared by vigorous shaking for 10-30 min using multi-wrist shaker, until a uniform and milky dispersion of multilamellar vehicle (MLV) will be formed and no remaining lipid film will be apparent. In order to obtain an equilibrated and homogenous liposome preparation the flask will be further shaken at 37° C. for 30-90 min. at 270 rpm.

Example 21. Preparation of Microemulsions Containing Polymeric Myrcenes

Several surfactants commonly used in parenterals may be utilized to develop water-in-oil and oil-in-water-microemulsions acceptable for injectable, oral and topical use. The pharmaceutically acceptable surfactants suitable for the formation of microemulsion formulations are non-ionic surfactants including polyoxyl 40 hydrogenated castor oil (sold under the trade name Cremophor RH40®), polyoxyl 35 castor oil (sold under the trade name Cremophor® EL), polyoxyethylene sorbitan fatty acid esters (polysorbates), poloxamers (Pluronics®), vitamin E-TPGS 1,000 (VE-TPGS 1,000), polyoxyethylene alkyl ethers, Solutol® HS-15, Tagat® TO, Peglicol 6-oleate, polyoxyethylene sterates, or saturated polyglycolyzed glycerides, all of which are commercially available. The preferred surfactants include polyoxyl 40 hydrogenated castor oil (Cremophor® RH40®), polyoxyl 35 hydrogenated castor oil (Cremophor® EL), polyoxyethylene sorbitan fatty acid esters (polysorbates), poloxamers (Pluronics®), and vitamin E-TPGS 1,000. The total amount of the surfactant present in the composition will be generally from about 100 to about 700 mg/g, and preferably from about 300 to about 500 mg/g.

Preparation of microemulsions containing polymeric myrcene may be performed by dissolving the polymeric myrcenes in an appropriate amount of oil such as medium chain tryglycerides (Miglyol) in a suitable vial. The vial is then capped. The vial is put into a water bath of about 50-60° C. and shaken gently until all of the drug material is completely dissolved. After the vial is cooled to room temperature, an appropriate amount of surfactant (such as Cremophor® EL or VE-TPGS) is added and followed by the mixture of mono- and di-glycerides of fatty acids, if any. The vial is then capped and placed into the water bath of about 50-60° C. The vial is shaken gently to obtain a clear, uniform solution. This solution can be filled into HPMC capsules and stored at room temperature before oral dosing. Alternatively, the substituted polymer powders (such as HPMC) can be added into the solution with adequate agitation (i.e., stirring, shaking) to obtain a uniform polymer suspension. The resulting composition can then be filled into either soft gelatin or hard gelatin capsules and stored at room temperature before oral dosing. Alternatively the microemulsion formulation can be used as a topically or filtered through 0.2 um membranes to be administered parenterally.

The microemulsions containing polymeric myrcenes have good water-dispersibility properties and self-emulsify when diluted in aqueous media to form small nanometric micelles that with enhanced bioavailability.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A composition consisting of an isolated fraction of mastic gum and an added pharmaceutically acceptable carrier, wherein the fraction is characterized in that it is soluble in at least one polar organic solvent and in at least one non-polar organic solvent, and wherein said fraction is substantially devoid of compounds which are soluble in said polar organic solvent but insoluble in said non-polar organic solvent, wherein the isolated fraction of mastic gum is obtained by a process comprising the steps of:
   (a) treating mastic gum with a polar organic solvent;
   (b) isolating a fraction soluble in said polar organic solvent;
   (c) treating the soluble fraction obtained in step (b) with a non-polar organic solvent; and
   (d) obtaining the isolated fraction of mastic gum by isolating a fraction soluble in said non-polar organic solvent.

2. The composition according to claim 1, wherein the mastic gum is obtained from a species of *Pistacia* selected from the group consisting of *P. lentiscus, P. atlantica, P. palestina, P. saportae, P. terebinthus, P. vera* and *P. integerrima*.

3. The composition according to claim 1, wherein the at least one polar organic solvent is selected from the group consisting of an alcohol, an ether, an ester, an amide, an aldehyde, a ketone, a nitrile, and combinations thereof; or
   wherein the polar organic solvent is selected from the group consisting of ethanol, methanol, propanol, isopropanol, 1-butanol, 2-butanol, sec-butanol, t-butanol, 1-pentanol, 2-pentanol, 3-pentanol, neopentanol, 3-methyl-1-butanol, 2-methyl-1-butanol, 3-methyl-2-butanol, 2-methyl-2-butanol, ethyleneglycol, ethyleneglycol monomethyl ether, diethyl ether, methylethyl ether, ethylpropyl ether, methylpropyl ether, 1,2-dimethoxyethane, tetrahydrofuran, dihydrofuran, furan, pyran, dihydropyran, tetrahydropyran, methyl acetate, ethyl acetate, propyl acetate, acetaldehyde, methylformate, ethylformate, ethyl propionate, methyl propionate, dichloromethane, chloroform, dimethylformamide, acetamide, dimethylacetamide, N-methylpyrrolidone, acetone, ethylmethyl ketone, diethyl ketone, acetonitrile, propionitrile, and combinations thereof; or
   wherein the at least one non-polar organic solvent is selected from the group consisting of acyclic or cyclic, saturated or unsaturated aliphatic hydrocarbons and aromatic hydrocarbons, each of which is optionally substituted by one or more halogens, and combinations thereof; or wherein the non-polar organic solvent is selected from the group consisting of C5-C10 alkanes, C5-C10 cycloalkanes, C6-C14 aromatic hydrocarbons and C7-C14 perfluoroalkanes, and combinations thereof; or wherein the non-polar organic solvent is selected from the group consisting of pentanes, hexanes, heptanes, octanes, nonanes, decanes, cyclopentane, cyclohexane, cycloheptane, benzene, toluene, xylene, and isomers and mixtures thereof; or wherein the non-polar organic solvent is hexane.

4. The composition according to claim 1, wherein said process further comprises the steps of:
(e) optionally removing, prior to step (c) the polar organic solvent of step (b); and/or
(f) optionally removing, after step (d) the non-polar organic solvent.

5. The composition according to claim 4, wherein said process further comprises the step of size fractionating the fraction obtained in step (b) or step (d); or
wherein either or both of steps (e) and (f) comprise removing the solvent by a means selected from the group consisting of rotary evaporation, application of high vacuum and a combination thereof; or
wherein said process further comprises repeating steps (a) to (b) and/or steps (c) to (d) for a multiplicity of cycles.

6. The composition according to claim 1, wherein the fraction is substantially devoid of terpene compounds which are soluble in said polar organic solvent and insoluble in said non-polar organic solvent.

7. The composition according to claim 1, comprising polymeric myrcene, wherein the polymeric myrcene has a number average molecular weight in the range of at least about 1,000 to about 20,000.

8. The composition according to claim 7, wherein the polymeric myrcene is selected from the group consisting of polymeric β-myrcene, polymeric α-myrcene, myrcene copolymers and combinations thereof; wherein the poly-β-myrcene is selected from the group consisting of cis-1,4-poly-β-myrcene, trans-1,4-poly-β-myrcene, 3,4-poly-β-myrcene, 1,2-poly-β-myrcene and combinations thereof.

9. The composition according to claim 1, comprising from about 0.01 to about 25% (w/w) of the isolated fraction of mastic gum, based on the total weight of the composition.

10. The composition according to claim 1, wherein the carrier is a hydrophobic carrier which is selected from the group consisting of:
a) at least one oil selected from the group consisting of cottonseed oil, almond oil, canola oil, coconut oil, corn oil, grape seed oil, olive oil peanut oil, saffron oil, sesame oil, soybean oil and combinations thereof;
b) at least one wax; and
c) combinations thereof.

11. The composition according to claim 1, which is in a form suitable for cosmetic or dermatologic administration; or
in a form suitable for administration by a route selected from the group consisting of oral, topical, parenteral, intramuscular, subcutaneous, intradermal, vaginal, rectal, intracranial, intranasal, intraocular, auricular, pulmonary intralesional, intraperitoneal, intraarterial, intracerebral, intracerebroventricular, intraosseus and intrathecal; or
in a form selected from the group consisting of a capsule, a tablet, a suppository, a suspension, an ointment, a cream, a lotion, a solution, an emulsion, a film, a cement, a powder, a glue, an aerosol and a spray.

12. The composition according to claim 1, which is:
a) an inclusion complex and the carrier contains at least one cyclodextrin;
b) a nanoemulsion in which droplets have an average particle size of less than 800 nm; or
c) a microemulsion and the carrier contains at least one non-ionic surfactant selected from the group consisting of a polyoxyl castor oil, a polyoxyethylene sorbitan fatty acid ester, a poloxamer, vitamin E, a polyoxyethylene alkyl ether, a polyoxyethylene stearates, a saturated polyglycolyzed glyceride and combinations thereof.

13. A composition consisting of an isolated fraction of mastic gum and an added pharmaceutically acceptable carrier, wherein the fraction is characterized in that it is soluble in at least one polar organic solvent and in at least one non-polar organic solvent, and wherein said fraction is substantially devoid of compounds which are soluble in said polar organic solvent but insoluble in said non-polar organic solvent, wherein said polar organic solvent is an alcohol, wherein the carrier is an oil selected from the group consisting of cottonseed oil, almond oil, canola oil, coconut oil, corn oil, grape seed oil, olive oil peanut oil, saffron oil, sesame oil, soybean oil and combinations thereof.

14. The composition of claim 13, wherein the alcohol is selected from the group consisting of ethanol, methanol, propanol, isopropanol, 1-butanol, 2-butanol, sec-butanol, t-butanol, 1-pentanol, 2-pentanol, 3-pentanol, neopentanol, 3-methyl-1-butanol, 2-methyl-1-butanol, 3-methyl-2-butanol, 2-methyl-2-butanol.

15. The composition of claim 13, wherein the at least one non-polar organic solvent is selected from the group consisting of acyclic or cyclic, saturated or unsaturated aliphatic hydrocarbons and aromatic hydrocarbons, each of which is optionally substituted by one or more halogens, and combinations thereof; or
wherein the non-polar organic solvent is selected from the group consisting of C5-C10 alkanes, C5-C10 cycloalkanes, C6-C14 aromatic hydrocarbons and C7-C14 perfluoroalkanes, and combinations thereof; or
wherein the non-polar organic solvent is selected from the group consisting of pentanes, hexanes, heptanes, octanes, nonanes, decanes, cyclopentane, cyclohexane, cycloheptane, benzene, toluene, xylene, and isomers and mixtures thereof; or wherein the non-polar organic solvent is hexane.

16. The composition according to claim 13, wherein the isolated fraction is obtained by a process comprising the steps of:
(a) contacting plant material with at least one alcohol, wherein the plant material is selected from the group consisting of resin, leaves, twigs, roots, flowers, seeds, buds, bark, nuts, roots and combinations thereof;
(b) isolating a fraction which remains soluble in the at least one alcohol solvent
(c) optionally removing said alcohol solvent;
(d) treating the soluble fraction obtained in step (b) or (c) with at least one non-polar organic solvent;
(e) isolating a fraction soluble in said nonpolar organic solvent; and
(f) optionally removing said nonpolar organic solvent;

wherein steps (a) to (c) and steps (d) to (f) are each independently optionally carried out for a number of cycles; so as to obtain an isolated fraction of mastic gum.

17. The isolated fraction according to claim 16, wherein said process further comprises the step of size fractionating the fraction obtained in step (c) or step (f); or
   wherein either or both of steps (c) and (f) comprise removing the solvent by a means selected from the group consisting of rotary evaporation, application of high vacuum and a combination thereof.

18. The composition according to claim 13, wherein the fraction is substantially devoid of terpene compounds which are soluble in said polar organic solvent and insoluble in said non-polar organic solvent.

19. The composition according to claim 13, wherein the fraction comprises polymeric myrcene, wherein the polymeric myrcene has a number average molecular weight in the range of at least about 1,000 to about 20,000.

20. The composition according to claim 13, comprising from about 0.01 to about 25% (w/w) of the isolated fraction of mastic gum, based on the total weight of the composition.

21. The composition according to claim 13, which is in a form suitable for cosmetic or dermatologic administration; or
   in a form suitable for administration by a route selected from the group consisting of oral, topical, parenteral, intramuscular, subcutaneous, intradermal, vaginal, rectal, intracranial, intranasal, intraocular, auricular, pulmonary intralesional, intraperitoneal, intraarterial, intracerebral, intracerebroventricular, intraosseus and intrathecal; or
   in a form selected from the group consisting of a capsule, a tablet, a suppository, a suspension, an ointment, a cream, a lotion, a solution, an emulsion, a film, a cement, a powder, a glue, an aerosol and a spray.

* * * * *